(12) United States Patent
Gunn et al.

(10) Patent No.: US 11,857,262 B2
(45) Date of Patent: Jan. 2, 2024

(54) INTRAOCULAR PHYSIOLOGICAL SENSOR

(71) Applicant: GLAUKOS CORPORATION, San Clemente, CA (US)

(72) Inventors: Nicholas Gunn, Newport Beach, CA (US); Cesario Pereira Dos Santos, Newport Beach, CA (US); David S. Haffner, Mission Viejo, CA (US)

(73) Assignee: GLAUKOS CORPORATION, San Clemente, CA (US)

( * ) Notice: Subject to any disclaimer, the term of this patent is extended or adjusted under 35 U.S.C. 154(b) by 486 days.

(21) Appl. No.: 16/147,182

(22) Filed: Sep. 28, 2018

(65) Prior Publication Data

US 2019/0104936 A1 Apr. 11, 2019

Related U.S. Application Data

(60) Provisional application No. 62/565,893, filed on Sep. 29, 2017.

(51) Int. Cl.
*A61B 3/16* (2006.01)
*A61B 5/07* (2006.01)
*A61B 3/00* (2006.01)

(52) U.S. Cl.
CPC .............. *A61B 3/16* (2013.01); *A61B 3/0025* (2013.01); *A61B 5/076* (2013.01); *A61B 2560/0257* (2013.01)

(58) Field of Classification Search
CPC .... A61B 2560/0257; A61B 2562/0247; A61B 3/16; A61B 5/0031; A61B 5/03; A61B 5/6821; A61B 5/6867; A61F 9/00781
See application file for complete search history.

(56) References Cited

U.S. PATENT DOCUMENTS

| 5,810,735 A | 9/1998 | Halperin et al. |
| 9,132,034 B2 | 9/2015 | Dos Santos |
| 2003/0078487 A1 | 4/2003 | Jeffries et al. |
| 2010/0036222 A1* | 2/2010 | Goode, Jr. ........... A61B 5/0031 600/365 |

(Continued)

FOREIGN PATENT DOCUMENTS

| JP | 10505529 A | 6/1998 |
| JP | 2016511107 A | 4/2016 |

(Continued)

OTHER PUBLICATIONS

International Search Report and Written Opinion for related International Application No. PCT/US18/53615; action dated Dec. 7, 2019; (20 pages).

(Continued)

*Primary Examiner* — David J. McCrosky
(74) *Attorney, Agent, or Firm* — K&L Gates LLP

(57) ABSTRACT

An intraocular pressure (IOP) sensing system may comprise an intraocular pressure sensing implant to be implanted into the eye of a patient for capturing absolute intraocular pressure measurements and an external device for capturing atmospheric pressure measurements. The intraocular pressure sensing implant may be configured to capture an absolute intraocular pressure measurement at an appointed time, and the external device may be configured to capture a plurality of atmospheric pressure measurements around the appointed time.

29 Claims, 55 Drawing Sheets

(56) References Cited

U.S. PATENT DOCUMENTS

2012/0296258 A1 11/2012 Rickard et al.
2014/0143582 A1 5/2014 Kindred et al.
2014/0275923 A1 9/2014 Haffner et al.
2017/0127941 A1 5/2017 Ostermeier et al.

FOREIGN PATENT DOCUMENTS

WO 2014/022521 A1 2/2014
WO 2014022521 A1 2/2014

OTHER PUBLICATIONS

International Preliminary Report on Patentability for related International Application No. PCT/US2018/053615; action dated Mar. 31, 2020; (11 pages).
Extended European Search Report for related European Application No. 18862190.8; action dated Jun. 2021 (10 pages).
Office Action for related Japanese Application No. 2020-517415; action dated Oct. 7, 2022; (9 pages).

\* cited by examiner

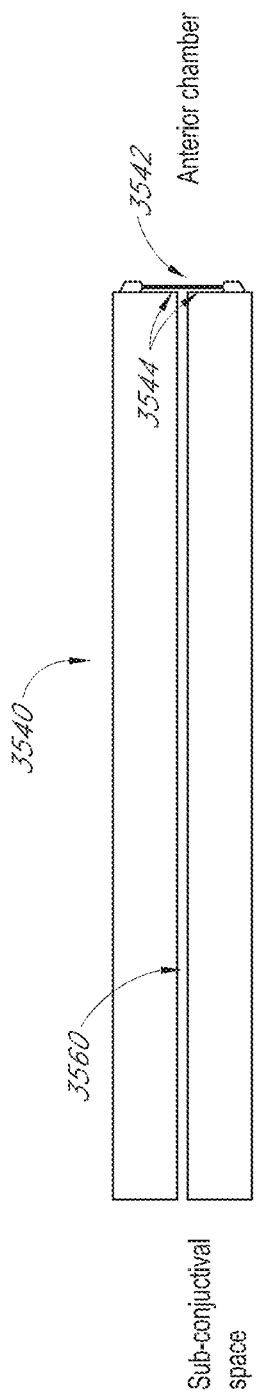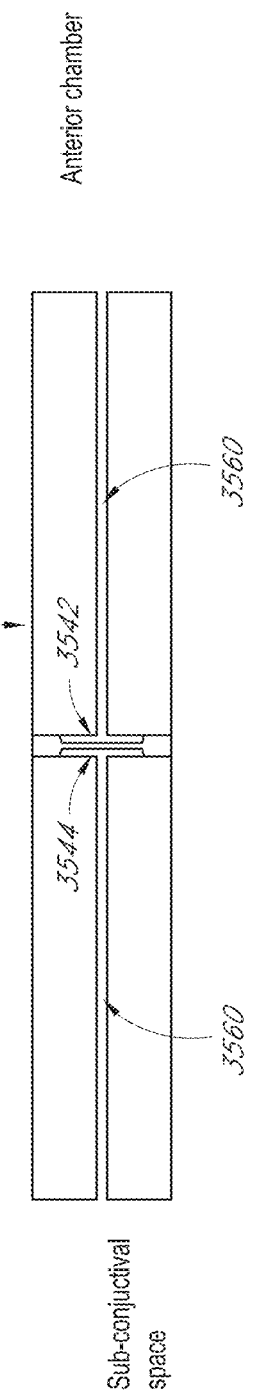

Timer inaccuracy of 0.1%:

Timer inaccuracy of 1%:

- Getting the entirety of the coil closer to the coil of the external device will improve link.

| Device | Description |
|---|---|
| IOP Sensor Implant | The implant records absolute pressure inside the eye |
| Physician diagnostic device | Device used by physician to download data, obtain on-demand IOP readings, re-charge implant, perform system diagnostics, re-program implant, etc. Form factor may be pair of glasses, soft mask, or similar. |
| Atmospheric Pressure Monitor device | Small patient-worn device that records local atmospheric pressure (to use for IOP calculation). Example form factors include wrist band, watch, pendant around the neck, application on smartphone, etc. |
| Daily/semi-daily Patient Device | Has the ability to download data and re-sync timers. Patient holds device to eye for ~1-2 seconds. Device may include screen to provide info to the patient (reminders, battery life, possibly IOP readout, etc.). |
| Daily Patient and Atmospheric Pressure Monitor Device | Combined functionality of above two devices |
| Patient at-home recharge device | Worn by the patient for ~30 min in order to recharge the battery and download data from the implant. Form factor may be pair of glasses, soft mask, or similar. Can also be used during doctor visits, for example while patient sits in waiting room. |
| At-home link-box | Connects to other patient devices, such as those listed above, in order to transfer the data collected by them to central server. Also can recharge the batteries in the devices. |
| Central server | Computer(s) at data processing location that receive patient data and process the data to prevent clean IOP data to the physician (collection of raw data from devices, filter algorithms, noise rejection, data integrity checking, etc.) Can also provide graphical user interface to physician to download or analyze data. |

FIG. 53

INTRAOCULAR PHYSIOLOGICAL SENSOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. Namely, this application claims priority to U.S. Provisional Patent Application 62/565,893, filed Sep. 29, 2017, and entitled "INTRAOCULAR PHYSIOLOGICAL SENSOR," the entirety of which is hereby incorporated by reference herein.

BACKGROUND

Field of the Invention

The field of the invention generally relates to implantable physiological sensors. In particular, embodiments of the invention generally relate to implantable intraocular sensors for measuring physiological characteristics such as intraocular pressure.

Description of the Related Art

Some diseases, including glaucoma, diabetes, and others, can be more effectively treated if they are diagnosed early and/or monitored effectively. Glaucoma, for example, is a leading cause of blindness. This disease damages the optic nerve in the eye due to elevated intraocular pressure, which can lead to complete vision loss if untreated. The risk of blindness can be reduced, however, if the elevated intraocular pressure is detected early and appropriately managed. Thus, there is a need for improved devices for monitoring physiological characteristics such as intraocular pressure.

BRIEF DESCRIPTION OF THE DRAWINGS

Various embodiments and features of devices, systems, and methods will be described with reference to the following drawings. The drawings, associated descriptions, and specific implementation are provided to illustrate embodiments of the invention and not to limit the scope of the disclosure.

FIG. 23 is a replica of FIG. 21 in which the main housing is shown as being see-through;

FIG. 34A illustrates an example embodiment of a capacitive absolute pressure sensor, while FIG. 34B illustrates an example embodiment of a capacitive differential pressure sensor.

FIGS. 35A and 35B illustrate respective first and second embodiments of a differential sensor which can obtain measurements indicative of the gauge pressure within the anterior chamber of the eye.

FIG. 53 is a table which describes several devices and systems which can be used in conjunction with the intraocular implants described herein.

DETAILED DESCRIPTION

There is a need to effectively monitor intraocular pressure within a patient's eye in order to detect, or monitor the progression of, glaucoma. Intraocular pressure can be measured non-invasively using, for example, a tonometer. While tonometers have the advantage of being non-invasive, they have the disadvantages of generally being expensive, non-portable, specialized equipment that requires skilled operation. Accordingly, as a practical matter, it is difficult to use a tonometer to effectively monitor intraocular pressure in a patient's eye with time resolution greater than one measurement every few days or weeks. However, since intraocular pressure can vary significantly over relatively short periods of time, such relatively sparse intraocular pressure measurements may not provide a complete or accurate picture of the patient's risk for glaucoma. It would, therefore, be advantageous to be able to measure intraocular pressure more often or even continuously.

Figure 1A:
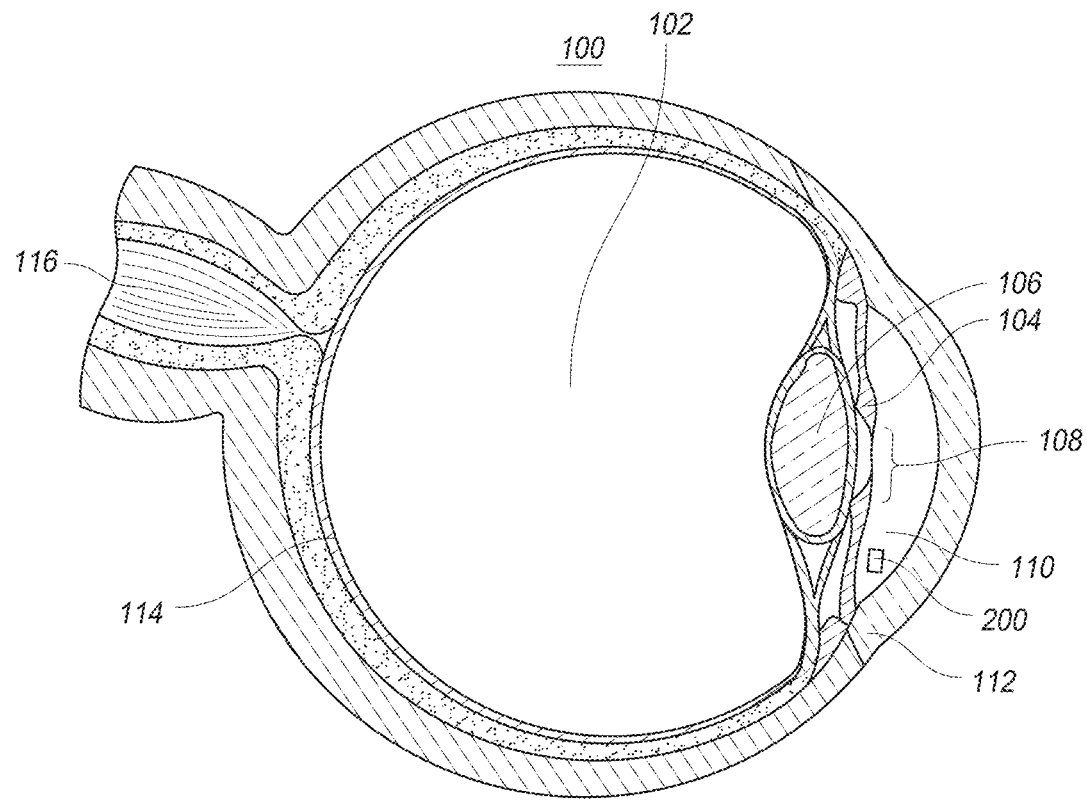
FIG. 1A is a schematic illustration of an implantable intraocular physiological sensor located in a human eye.

FIG. 1A is a schematic illustration of an implantable intraocular physiological sensor 200 located in a human eye 100. For reference, various anatomical features of the eye 100 are labeled in FIG. 1. For example, FIG. 1A shows the vitreous humor 102, the iris 104, the lens 106, the pupil 108, the anterior chamber and aqueous humor 110, the cornea 112, the retina 114, and the optic nerve 116. FIG. 1 also illustrates an intraocular physiological sensor 200 that is located within the anterior chamber of the eye. The intraocular physiological sensor 200 is capable of measuring, for example, intraocular pressure within the eye. The intraocular physiological sensor 200 can also, or alternatively, be designed to measure any of several other physiological characteristics, as discussed herein. It should be understood that the intraocular physiological sensor 200 is not necessarily drawn to scale.

Figure 1B:
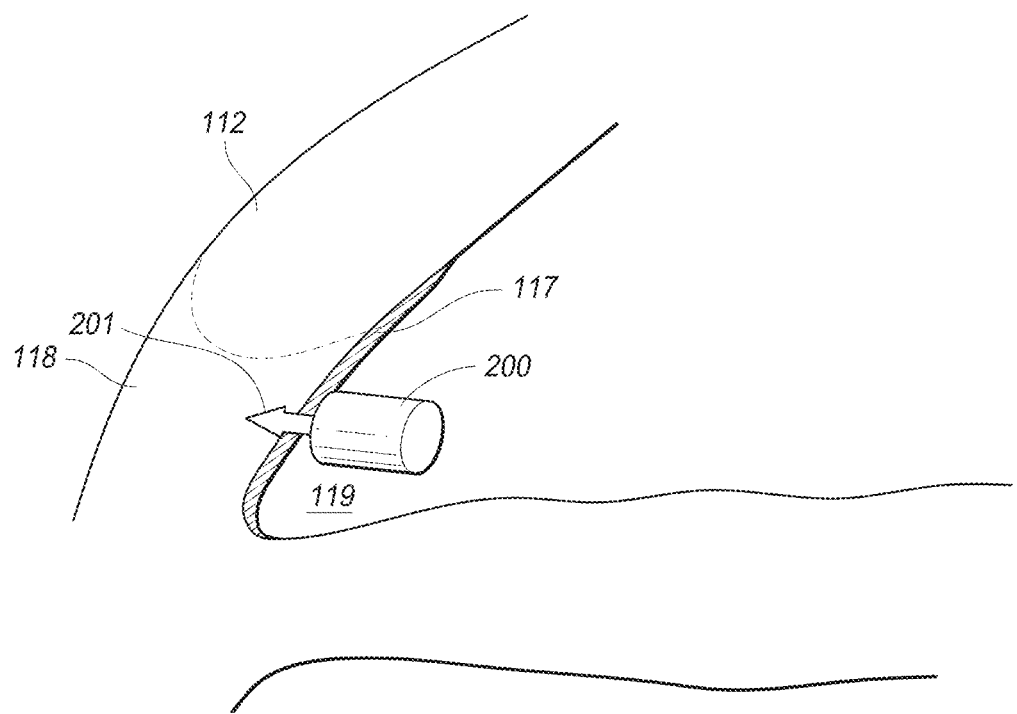
FIG. 1B is a schematic illustration of an implantable intraocular physiological sensor fixed by an anchor through meshwork tissue embedded into scleral tissue in the iridocorneal angle.

In addition, the sensor 200 could be positioned at several different locations within the eye. For example, the intraocular physiological sensor 200 could be fixedly attached or anchored to any suitable anatomical feature of the eye, including but not limited to the sclera or iris, depending upon the particular application. As discussed further below, the intraocular physiological sensor 200 could be fixedly attached or anchored to or within a physiological aqueous humor outflow pathway. The physiological aqueous humor outflow pathways include the "conventional" pathway comprising the trabecular meshwork and Schlemm's canal; and the "uveoscleral" pathway comprising the ciliary body, the sclera, and the supraciliary/suprachoroidal space. FIG. 1B illustrates the location of the sensor 200 fixed by an anchor 201 through meshwork tissue 117 embedded into scleral tissue 118 in the iridocorneal angle 119.

Figure 1C:
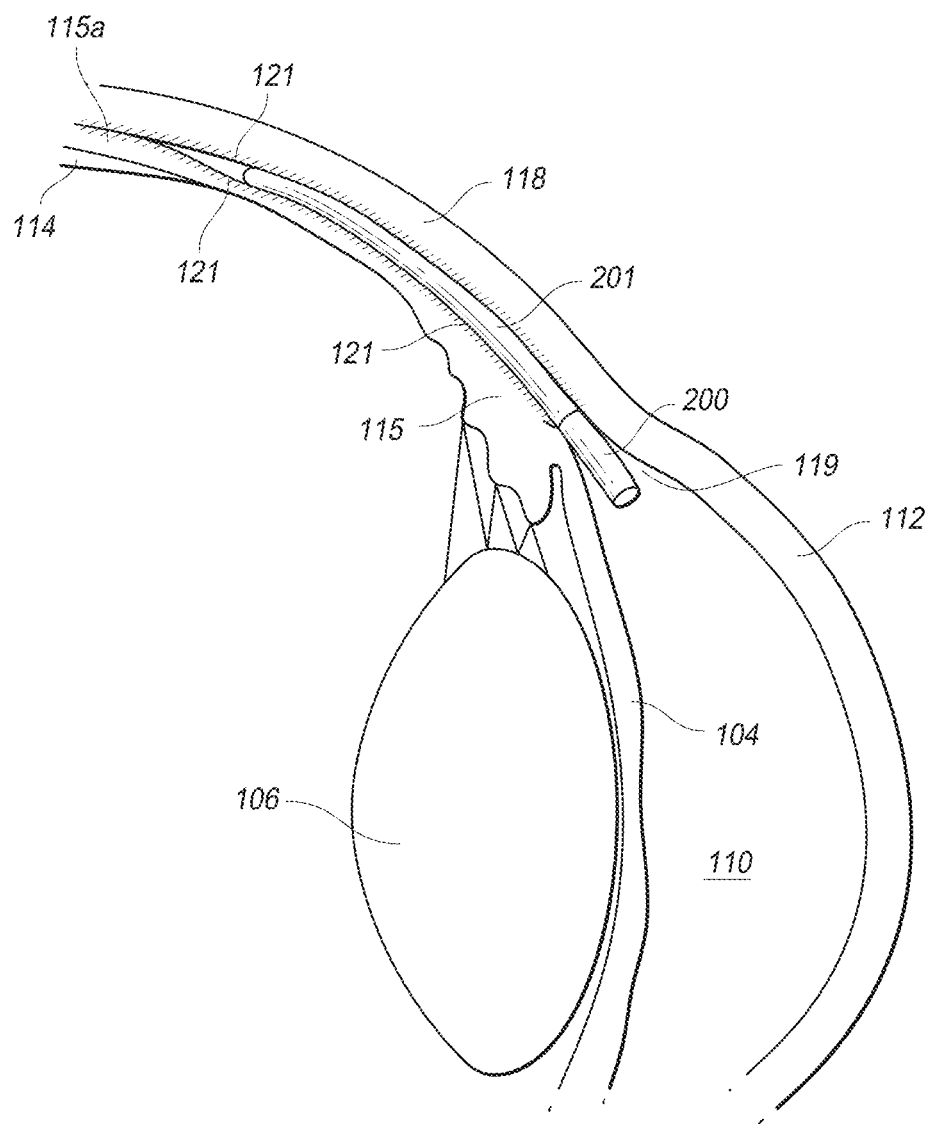
FIG. 1C is a schematic illustration of an implantable intraocular physiological sensor fixed by an anchor within the supraciliary/suprachoroidal space between the ciliary body/choroid and the sclera.

FIG. 1C illustrates the location of the sensor 200 fixed by an anchor 201 within the supraciliary/suprachoroidal space between the ciliary body/choroid and the sclera 118. The ciliary body 115 is contiguous with the choroid 115a. The supraciliary/suprachoroidal space is normally a potential space at the interface between the ciliary body/choroid and sclera. The space may open to accommodate an implant such as the sensor 200 and/or the anchor 201. The supraciliary/suprachoroidal space is thus identified schematically by the hatching 121 in FIG. 1C. FIG. 1C illustrates an example of placement of the intraocular physiological sensor 200 (which may be partially or completely located within the anterior chamber 110; or may be partially or completely located within the supraciliary/suprachoroidal space 121) and the anchor 201. In other embodiments, the physiological sensor that is implanted within the supraciliary/suprachoroidal space could be configured such as the sensor 500 shown in FIG. 5A.

Alternatively, the sensor 200 could be attached to some other ocular implant, such as an intraocular lens. Regardless of location, care should be taken to avoid contact of the sensor with the corneal endothelium.

The intraocular physiological sensor 200 may also, or alternatively, measure glucose concentration in the aqueous humor 110. There is a need to measure glucose concentration within the human body as a means to treat or prevent complications from diabetes. Typically, glucose is measured from the blood or urine. Some implantable glucose sensors have been developed that measure glucose from interstitial fluids. However, the body may have a negative immunological response to such implants, which may degrade the performance of the sensor over time. However, the eye, especially the anterior chamber of the eye, is an immunologically-privileged site within the body. Thus, an implantable sensor for measuring glucose within the eye could have advantages over other implantable sensors that are made to measure glucose in non-immunologically privileged parts of the body. In addition, although the glucose concentration within the aqueous humor may not be identical to blood glucose concentration, the two may be correlated such that a measurement of glucose concentration in the aqueous humor can be predictive of blood glucose concentration.

For some embodiments, such as intraocular pressure sensors, it may be possible to implant the sensor portion completely within the supraciliary/suprachoroidal space. In some embodiments, a modest level of fibrosis may not interfere with satisfactory functioning of the implanted sensor.

As already mentioned, in some embodiments, the intraocular physiological sensor 200 measures both intraocular pressure and glucose concentration in the aqueous humor. This can be advantageous because the glucose concentration measurement can be used to diagnose and/or treat diabetes. Meanwhile, diabetes patients are also at higher risk of developing glaucoma. Thus, there may be a significant overlap of the patient population for whom intraocular pressure and glucose concentration measurements would be valuable.

In some embodiments, the intraocular physiological sensor 200 is wholly or partially powered using a fuel cell that converts a substance found in the human body into, for example, electrical power. For example, in some embodiments, the fuel cell is an electrochemical fuel cell that produces electricity using the glucose dissolved in the aqueous humor. Thus, the glucose itself acts as a renewable fuel for powering the physiological sensor 200.

In contrast, other implantable physiological sensors may be wholly dependent upon batteries or an external source for their power. However, in the case of battery-operated implantable physiological sensors, the capacity of the battery may tend to limit the useful lifetime of such implantable sensors. If the useful lifetime provided by the battery is not adequate for a given application, the implantable sensor may need to be replaced. This is disadvantageous because insertion of an implantable sensor is an invasive process and may require surgery with all of its attendant risks. Alternatively, some implantable physiological sensors rely upon external devices for power (e.g., for real-time operation using the externally-supplied power or to re-charge an internal battery). For example, an implantable physiological sensor may be externally powered via inductive coupling or RF energy from an external device. However, even though such an external power source may remove or reduce the reliance of the implantable physiological sensor's useful lifetime on a battery, external power sources may also introduce other undesirable operating limitations. For example, the time resolution of measurements from such implantable sensors may be limited if measurements can only be performed while the sensor is externally-powered.

Therefore, the fuel cell-operated intraocular physiological sensor 200 is advantageous because it may be expected to have a greater useful lifetime than sensors that are wholly reliant upon a battery or external device for operating power. In addition, such implantable sensors could be used to perform measurements relatively more often, or even continuously.

Figure 2:
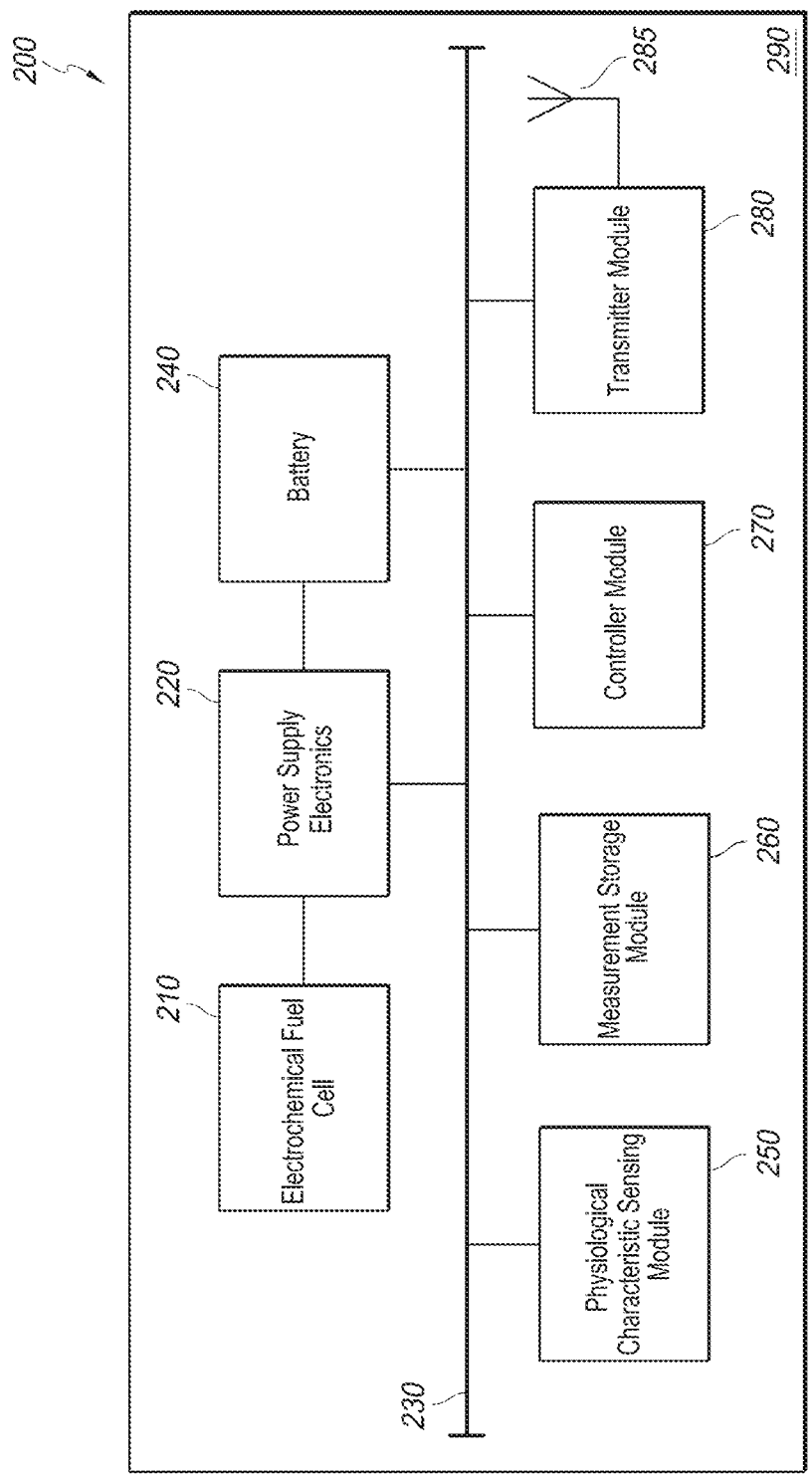
FIG. 2 is a block diagram of an implantable intraocular physiological sensor that includes an electrochemical fuel cell.

FIG. 2 is a block diagram of the implantable intraocular physiological sensor 200. In some embodiments, the implantable intraocular physiological sensor 200 includes an electrochemical fuel cell 210 and power supply electronics 220. The implantable intraocular physiological sensor 200 may also include a battery 240 that is charged by the electrochemical fuel cell 210. In some embodiments, the implantable intraocular physiological sensor 200 includes a physiological characteristic sensing module 250, a measurement storage module 260, a controller module 270, and a transmitter module 280 with an antenna 285. Each of the components of the implantable intraocular physiological sensor 200 may be wholly or partially housed in a biocompatible housing 290. It should be understood that, although the implantable physiological sensor 200 is described primarily herein with respect to intraocular applications, it may also be used in parts of an organism other than an eye.

In embodiments of the physiological sensor without a fuel cell, there may be an on board power supply such as a battery, or a solar cell combined with a battery or storage capacitor. The battery may be a rechargeable battery that can be recharged by an external device (e.g., a device used to download physiological measurements). In other embodiments of the physiological sensor without a fuel cell, power may be provided by inductive or RF means. In still other embodiments of the physiological sensor without a fuel cell, the sensor may comprise a component of a passive resonant circuit which is interrogated by an external instrument, such as described in "Microfabricated Implantable Parylene-Based Wireless Passive Intraocular Pressure Sensors," by P-J Chen et al., in Journal of Microelectromechanical Systems (2008), volume 17, which is incorporated herein by reference in its entirety.

The physiological characteristic sensing module 250 is a component that performs measurements of a physiological characteristic of interest. For example, the physiological characteristic sensing module 250 outputs a signal (e.g., an electrical signal) that is quantitatively representative of the physiological characteristic under measurement. As discussed herein, the physiological characteristic sensing module 250 may be designed to measure intraocular pressure. There are several different tonometric devices for measuring intraocular pressure. Some sensors are described in U.S. Pat. No. 7,678,065, which is incorporated by reference herein in its entirety. The physiological characteristic sensing module 250 can make use any of these, or future-developed devices. Alternatively, the physiological characteristic sensing module 250 can be designed to measure intraocular glucose concentration. In still other embodiments, the physiological characteristic sensing module 250 can be designed to measure any of the biomarker substances in Table 1, which are listed with the corresponding physiological condition of which they may be indicative.

TABLE 1

| Detected Biomarker | Corresponding Condition |
| --- | --- |
| Interleukin-2, interleukin-6, interleukin-10, interleukin-12, interferon-γ, tumor growth factor-β2, tumor necrosis factor-α, macrophage migration inhibitory factor | Uveitis |
| 8-Hydroxy-2'-deoxyguanosine | Age-Related Macular Degeneration (AMD) |
| aB-crystallin, a-enolase, and glial fibrillary acidic protein | AMD |
| Pentosidine, and N-carboxymethyl-lysine | Diabetic Retinopathy |
| Monocyte chemoattractant protein-1 and interleukin-8 | Diabetic Macular Edema (DME) |
| Interphotoreceptor retinoid-binding protein | Blood-Retinal Barrier (BRB) breakdown/inflammation |
| Survivin | Retinoblastoma/ocular tumor |
| VEGF | Ocular ischemia |
| Amyloid-β | Alzheimer's |
| Intercellular adhesion molecule-1 (ICAM1) | DME |
| TNF-α | Glaucoma |
| TGF-beta3 | Glaucoma |
| Transforming growth factor-beta2 | Glaucoma, diabetes |

In some embodiments, the implantable physiological characteristic sensing module 250 may include a temperature sensor for temperature correction of the physiological sensor 200; and/or may include an oxygen sensor for correcting the physiological sensor 200 for the partial pressure of oxygen.

In some embodiments, the intraocular physiological sensor 200 may comprise a fluorescent sensor, such as disclosed in U.S. Pat. No. 7,653,424 and U.S. Patent Application 2007/0030443, which are incorporated herein by reference in their entirety. In these embodiments, the implanted sensor 200 may not require an onboard power supply, and may be interrogated by an external device.

In some embodiments, the implantable intraocular physiological sensor 200 includes multiple instances of the physiological characteristic sensing module 250. Each instance of the sensing module 250 may be used to measure a different physiological characteristic. As discussed herein, in some embodiments, the physiological sensor 200 includes two sensing modules 250 for measuring intraocular pressure and glucose concentration. Again, the physiological characteristic sensing module(s) 250 can use any known or later-developed device for measuring the foregoing substances, or any other physiological characteristic of interest for a particular application.

In some embodiments, the physiological characteristic sensing module 250 is controlled (e.g., by the controller module 270) to perform a measurement at regular intervals. For example, the sensing module 250 may perform a measurement at least hourly, at least every 15 minutes, at least every minute, or at other intervals, depending upon the particular application. In some embodiments, the physiological characteristic sensing module 250 performs measurements substantially continuously. In this way, trend data regarding the physiological characteristic of interest can be collected so as to provide a more useful or complete picture of how the physiological characteristic changes as a function of time. Alternatively, in some embodiments, readings could be taken less frequently throughout the day (e.g., 4-6 times per day vs. continuously or every 15 minutes) in order to conserve energy (e.g., battery life).

The implantable intraocular physiological sensor 200 may also include a transmitter module 280 that is communicatively coupled to an antenna 285 for wirelessly transmitting measurements from the physiological characteristic sensing module 250 to an external device. In some embodiments, the transmitter module 280 may be replaced by a transceiver module which is capable of also receiving communications (e.g., control commands) from the external device. Any type of suitable transmitter or transceiver device that is known or developed in the future can be used.

In some embodiments, the physiological characteristic sensing module 250 may comprise an electrical circuit that develops a resonant frequency as a function of the level of physiological characteristic, wherein the resonant frequency can be determined with an external device. In this kind of embodiment, the module 250 may employ an antenna for wireless communication, but not necessarily a transmitter (see, for example, Microfabricated Implantable Parylene-Based Wireless Passive Intraocular Pressure Sensors, by P-J Chen et al., in Journal of Microelectromechanical Systems (2008), volume 17, which is incorporated herein by reference in its entirety). In some embodiments, the physiological characteristic sensing module 250 and/or transmitter module 280 may comprise an optical (such as infrared) emitter and/or detector for wirelessly transmitting measurements to, and/or receiving instructions from, an external device.

The transmitter module 280 may be controlled (e.g., by the controller module 270) to transmit measurements at, for example, predetermined intervals, continuously, or upon command from the external device to which the data is being transmitted. In some embodiments, the external device to which measurement data are transmitted may be a data logger that is worn by the patient for storing the measurements until they can be downloaded by a clinician. In other embodiments, the external device may be a handheld reader device used by a clinician to periodically download measurement data that is stored internally by, for example, the measurement storage module 260. The reader device can then transmit the downloaded measurements to a computer (e.g., via the Internet or some other communication network) for processing and/or for analysis by a clinician. In some embodiments, the transmitter module 280 transmits glucose concentration measurements to an insulin pump that is worn by the patient. Such measurements can be used by the insulin pump to control the injection of insulin into the patient's body. The reader device can also provide the downloaded measurements to the patient via a user interface. In the case of glucose concentration measurements, for example, the patient case use the measurements to manage his or her diet and/or exercise.

The implantable intraocular physiological sensor 200 may optionally include a measurement storage module 260. The measurement storage module 260 can be used to internally log measurements from the physiological characteristic sensing module 250, for example, until they can be retrieved by an external device that is communicatively coupled to the measurement storage module 260 via the transmitter module 280. The measurement storage module 260 can be, for example, a solid-state electronic memory device. In some embodiments, the physiological sensor 200 is configured to download, for example, a day or other time period's worth of measurements (e.g., IOP measurements) at a time to an external receiver located, for example, at the bedside of the patient. Data could also be downloaded more or less frequently than daily. In some embodiments, the downloading of data is an automated process. Once measurement data is downloaded to an external device, it can be transferred to a remote reading center for preparation of reports for the patient's ophthalmologist or other managing physician. In addition, the intraocular physiological sensor 200 could include a storage module configured to store other data besides, or in addition to, physiological measurements. For example, the storage module could be loaded with the patient's electronic medical record data, or any other private or sensitive data. In some embodiments, an implantable intraocular device may forgo physiological sensing capabilities and be used primarily to provide a storage module for storing data in a secure but easily accessible, immunologically privileged location. For example, the storage module could hold identification information associated with the patient for security purposes. This information could be accessed, for example, using an external reader to interrogate the implanted device, as discussed herein The implantable intraocular physiological sensor 200 also includes a controller module 270. The controller module 270 can be used, for example, to perform control operations for the other components of the physiological sensor 200. In some embodiments, the controller module 270 may provide commands to the physiological characteristic sensing module 250 to perform measurements. The controller module 270 may also control the writing and reading of data to the measurement storage module 260 and the operation of the transmitter module 280. In addition, the controller module 270 may control power settings of the electrochemical fuel cell 210, the power supply electronics 220, and battery 240. As discussed further below, the interconnecting lines shown in FIG. 2 primarily represent power supply connections. It should be understood, however, that signal and/or command lines can be provided between any and all of the components of the sensor 200 (e.g., between the controller module 270, the physiological characteristic sensing module 250, the measurement storage module 260, the transmitter module 280, and/or the power supply electronics 220, etc.) as necessary.

The controller module 270 may also perform other functions. For example, in some embodiments, the controller module 270 can perform data processing tasks on the measurements collected by the physiological characteristic sensing module 250, though in other embodiments any such required data processing can be performed by an external device after downloading the measurements in order to avoid the power demands of such onboard processing. In addition, the controller module 270 may monitor the collected measurements and output alarm signals (e.g., to an external device via the transmitter module 280) if the physiological characteristic that is being monitored reaches some threshold value or if immediate notification is otherwise considered necessary. For example, an alarm signal can be triggered if the sensor detects a potentially dangerous low blood sugar level. The controller module 270 can also perform measurement data compression (to allow for more measurements to be stored on the measurement storage module 260). In addition, the controller module 270 can issue commands to other components of the physiological sensor 200 (e.g., the transmitter module 480, the measurement storage module 460, the physiological characteristic sensing module 450, etc.) to shut down or enter a power-saving state when not in use.

As briefly discussed above, the implantable intraocular physiological sensor 200 may include a fuel cell such as the electrochemical fuel cell 210. In some embodiments, the electrochemical fuel cell 210 uses glucose in the aqueous humor 108 to produce electrical power from a chemical reaction with the glucose. The electrical power produced by the electrochemical fuel cell 210 can be used to satisfy the power demands, whether in whole or in part, of any or all of the other components of the implantable intraocular physiological sensor 200. An electrical bus 230 is illustrated in FIG. 2. The electrical bus 230 is energized by the electrochemical fuel cell 210 (e.g., via power supply electronics 220 and/or a battery 240). Any other components of the implantable intraocular physiological sensor 200 can be connected to the electrical bus 230 (as illustrated by the interconnecting lines in FIG. 2) to receive operating power, as necessary.

The electrochemical fuel cell 210 can be connected to power supply electronics 220. The power supply electronics 220 can include, for example, a voltage regulator, a voltage converter, or any other electrical component that may be desirable for conditioning the electrical power output by the electrochemical fuel cell 210 so that it can be satisfactorily used by other electrical components within the implantable intraocular physiological sensor 200. In some embodiments, the electrochemical fuel cell 210 can be used to charge a battery 240. A battery 240 may be useful, for example, in cases where data transmission from the transmitter module 280 requires a burst of power that is greater than the instantaneous power available from the electrochemical fuel cell 210. The battery 240 may also be useful in providing a steady level of electrical power to other components of the implantable intraocular physiological sensor 200 in circumstances where, for example, the supply of fuel (e.g., glucose) used by the fuel cell 210 is irregular. Although the implantable intraocular physiological sensor 200 includes the electrochemical fuel cell 210 to at least partially satisfy power demands, it should be understood that the presence of the fuel cell 210 does not necessarily preclude the use of other internal or external power sources to provide additional operating power to the physiological sensor 200. Moreover, in some embodiments, the intraocular physiological sensor 200 may include two or more batteries in addition to, or in place of a fuel cell. In such embodiments, one battery can become active after another becomes too discharged for further use, thus extending the useful life of the sensor. The changeover between batteries can be controlled, for example, by software and/or hardware.

According to some estimates, the average power consumption of the physiological sensor 200 may be less than about 10 nW, assuming that a measurement is made by the physiological characteristic sensing module 450 every 15 minutes and that the transmitter module 480 performs data transmission once daily. Thus, in some embodiments, the electrochemical fuel cell 210 has an average power output of at least about 10 nW. However, if, for example, measurements or data transmission are performed more frequently, or if more than one physiological characteristic is monitored, etc., then power demands may be greater. Therefore, in some embodiments, the electrochemical fuel cell 210 produces an average power output of at least about 10 µW, or more.

The implantable intraocular physiological sensor 200 may also include other modules in addition to those that are specifically illustrated. For example, the implantable intraocular physiological sensor 200 could include a Global Positioning System (GPS) module for providing location information about the patient's whereabouts. The GPS module could, for example, store a reading of the patient's location at each time that a physiological measurement is performed. The location information could be downloaded from the physiological sensor 200 along with physiological measurements and used, for example, to access a weather database with barometric pressure information from the patient's location. Such barometric pressure information can then be used to perform any necessary corrections to the intraocular pressure measurements that were detected by the physiological sensor 200.

Figure 3:
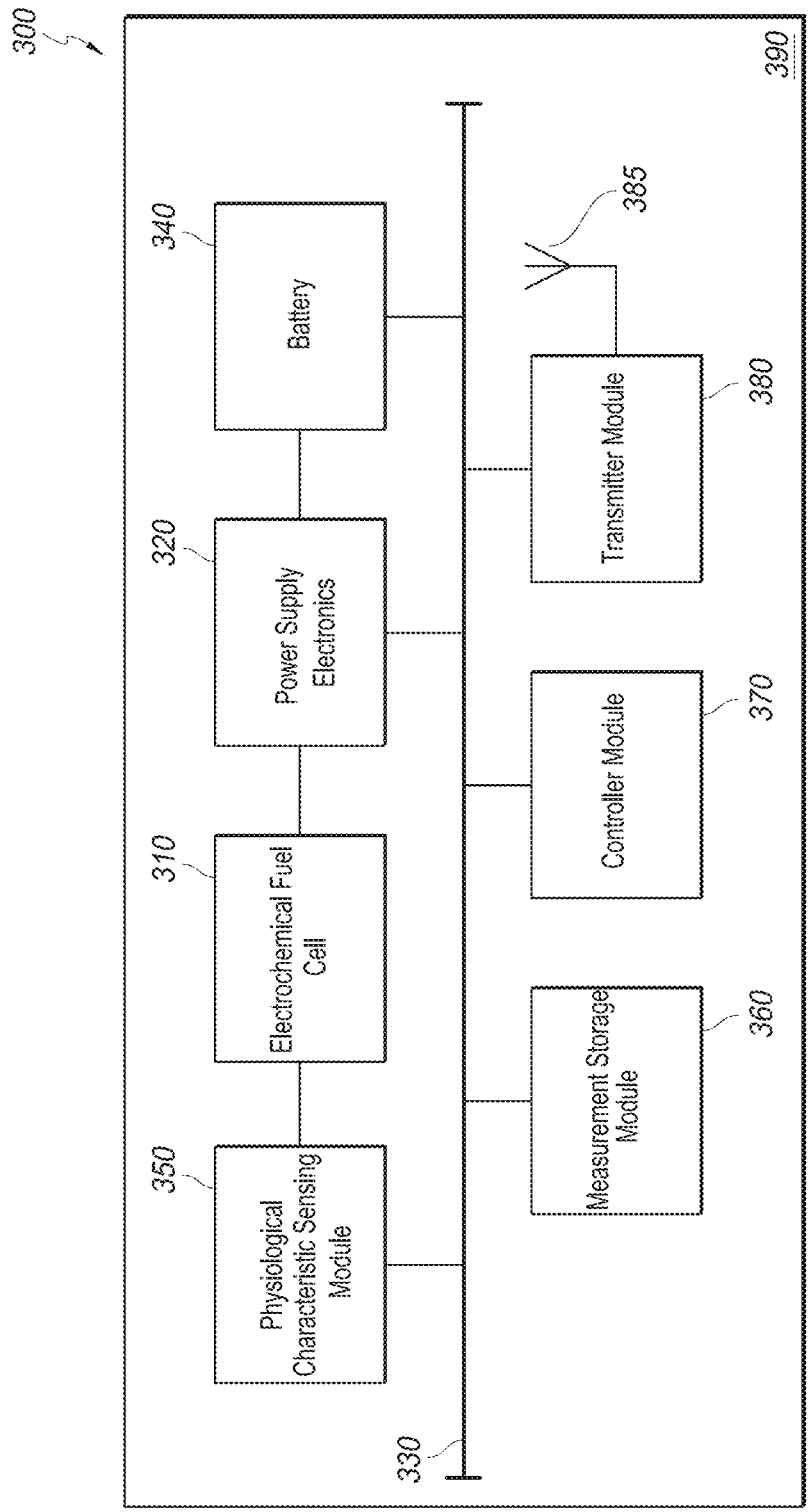
FIG. 3 is a block diagram of an implantable intraocular physiological sensor in which a physiological characteristic is measured based on the output from an electrochemical fuel cell.

FIG. 3 is a block diagram of an implantable intraocular physiological sensor 300 in which a physiological characteristic is measured based on the output from an electrochemical fuel cell 310. The implantable intraocular physiological sensor 300 can include, for example, an electrochemical fuel cell 310, power supply electronics 320, an electrical bus 330, a battery 340, a physiological characteristic sensing module 350, a measurement storage module 360, a controller module 370, a transmitter module 380 coupled to an antenna 385, and a biocompatible housing 390. Each of these components can be similar to the corresponding components described with respect to FIG. 2.

In the implantable intraocular physiological sensor 300, the physiological characteristic sensing module 350 measures the amount of the substance (e.g., in the vicinity of the physiological sensor 300) that is used by the electrochemical fuel cell 310 to generate power. For example, the electrochemical fuel cell 310 may be a glucose fuel cell and the sensing module 350 may be designed to measure glucose concentration in the aqueous humor. In this embodiment, the sensing module 350 is shown with a direct connection to the electrochemical fuel cell 310 to indicate that the sensing module 350 measures glucose concentration based upon the electrical current or voltage that is output by the electrochemical fuel cell 310. For example, when glucose is present in the aqueous humor of the eye in greater concentrations, the electrochemical fuel cell 310 may produce a larger electrical current or voltage, and vice versa for smaller glucose concentrations. The glucose measurement provided by the physiological characteristic sensing module 350 may be, for example, proportional to the electrical current or voltage from the fuel cell 310.

Figure 4:
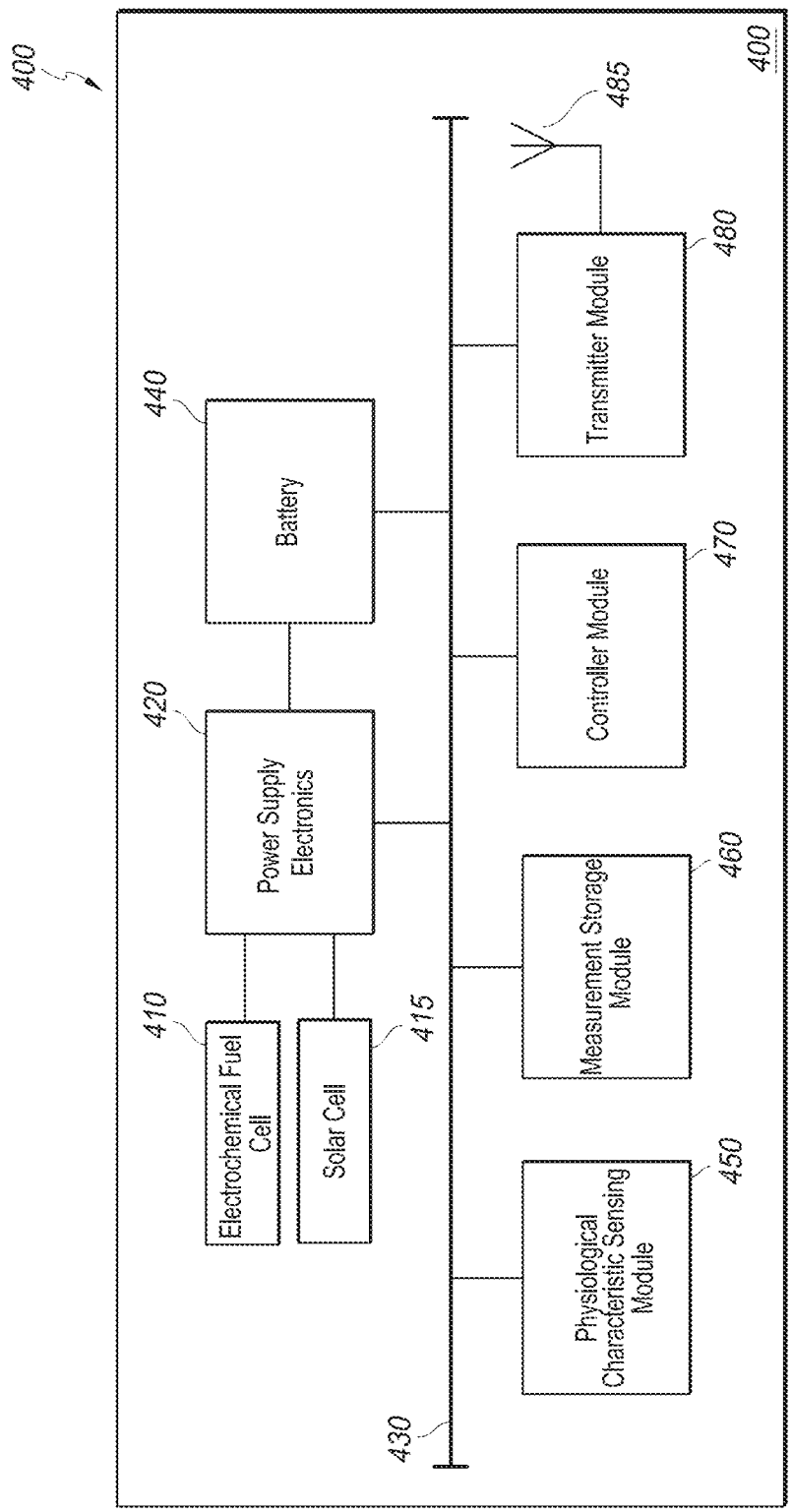
FIG. 4 is a block diagram of an implantable intraocular physiological sensor that includes an electrochemical fuel cell and/or a solar cell.

FIG. 4 is a block diagram of an implantable intraocular physiological sensor 400 that includes an electrochemical fuel cell 410 and/or a solar cell 415. The electrochemical fuel cell 410, power supply electronics 420, electrical bus 430, battery 440, physiological characteristic sensing module 450, measurement storage module 460, controller module 470, transmitter module 480 and antenna 485, and biocompatible housing 490 can be similar to the corresponding components described with respect to FIGS. 2 and 3.

The implantable intraocular physiological sensor 400 can also include a solar cell 415. The solar cell 415 generates power from any light that enters the eye 100. The solar cell 415, which can be of any suitable type currently known or developed in the future, can be used to at least partially satisfy power demands of the various components of the physiological sensor 400. For example, if the electrochemical fuel cell 410 is unable to satisfy the power requirements of the physiological sensor 400, then the solar cell 415 can be used as an additional power source to help satisfy those requirements. In some embodiments, the solar cell 415 is used to energize an electrical bus 430 (e.g., via the power supply electronics 420) to which other components of the physiological sensor 400 are connected. The solar cell 415 can also be used to charge a battery 440 so that the physiological sensor 400 can still operate in dark conditions. The solar cell 415 can be included, for example, in addition to, or in place of, the electrochemical fuel cell 410.

As discussed above, the foregoing embodiments may be used in the diagnosis or treatment of glaucoma. About two percent of people in the United States have glaucoma.

Glaucoma is a group of eye diseases that causes pathological changes in the optic disk and corresponding visual field loss, resulting in blindness if untreated. Intraocular pressure elevation is a major etiologic factor in glaucoma. In certain embodiments, a sensor implant, such as those described herein, may be used and/or delivered together with one or more implants that provide for drug delivery to the eye and/or drainage of aqueous humor from the anterior chamber as a treatment for glaucoma.

In glaucomas associated with an elevation in intraocular pressure ("IOP"), the source of resistance to outflow of aqueous humor is mainly in the trabecular meshwork. The tissue of the trabecular meshwork allows the aqueous humor, or aqueous, to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens. The aqueous humor is continuously secreted by the ciliary body around the lens, so there is an essentially constant flow of aqueous humor from the ciliary body to the eye's anterior chamber. The anterior chamber pressure is determined by a balance between the production of aqueous and its exit through the trabecular meshwork (major route) or uveoscleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Two primary methods of alleviating the imbalance between the production and drainage of aqueous humor are use of pharmaceuticals that reduce IOP and use of ocular implants that enhance drainage of aqueous from the anterior chamber. Implants may provide a route to allow drainage of aqueous from the anterior chamber. The implant may be designed to allow drainage to any suitable location, including the subconjunctival space (including use of a bleb) and a physiologic outflow path such as Schlemm's canal or the uveoscleral outflow pathway (including suprachoroidal space and/or supraciliary space).

Any of a wide variety of ocular implants to enhance aqueous drainage may be used in connection with other implants as disclosed herein. For example, U.S. Pat. Nos. 6,638,239 and 6,736,791 disclose devices and methods of placing a drainage device or shunt ab interno. The stent includes a hollow, elongate tubular element, having an inlet section and an outlet section. The outlet section may optionally include two segments or elements, adapted to be positioned and stabilized inside Schlemm's canal. In one embodiment, the device appears as a "T" shaped device. In another embodiment, the device appears as a "L" shaped device. In still another embodiment, the device appears as a "I" shaped embodiment. The entire contents of each one of these patents are hereby incorporated by reference herein.

Other implants are suitable for use in providing aqueous drainage. For example, one embodiment of a drainage implant has a longitudinal axis and comprises a first portion sized and configured to reside at least partially in the anterior chamber and a second portion sized and configured to reside within Schlemm's canal, the suprachoroidal space, or another physiological outflow pathway of the major or minor route. The first portion also includes an inlet section that communicates with a lumen that runs along the longitudinal implant axis and communicates with one or more exit or outflow ports in the second portion of the device. Another type of device may be in a form that resembles a rivet, wherein there is an inlet portion that resides in the anterior chamber, a distal portion having one or more outlets and is adapted to reside in a physiologic outflow pathway (e.g. Schlemm's canal, uveoscleral outflow pathway, suprachoroidal space, supraciliary space), and an intermediate portion adapted to extend through tissue and provide fluid communication between the inlet and distal portions. The devices may also comprise one or more retention features (e.g. ridges, barbs, protrusions, etc.) to assist in retaining the device in the desired location in the eye. Such devices may also include one or more drugs. These and other suitable implants are disclosed in U.S. Pat. Nos. 7,135,009, 7,857, 782, 7,431,710, and 7,879,001, the disclosures of which are hereby incorporated by reference in their entireties.

Any of the foregoing implants may feature a drug coating in addition to providing drainage, wherein the drug may be any type as disclosed herein, including drugs to treat glaucoma or other eye conditions, and drugs to prevent or reduce scarring, fibrosis, clotting and other deleterious effects that may result from implantation of a device. In other embodiments, the devices may be adapted to deliver one or more drugs over a desired period of time by providing the drug in bulk form, e.g. placed in a recess or lumen in the device, or in the form of a tablet or mass that is affixed to or contained within the body of the device. Bulk drug may also take the form of a tiny pellet or tablet which may be placed in a recess or lumen of a device or affixed to the device. Where the drug is present in bulk form, the device may also include a drainage lumen. In some embodiments, the drainage lumen also includes drug so that drainage of aqueous facilitates drug elution. Devices may also include both bulk drug and a drug coating. Examples of such devices are found in International Patent Application Publication No. WO 2010/135369, the disclosure of which is hereby incorporated by reference in its entirety.

Figure 5A:
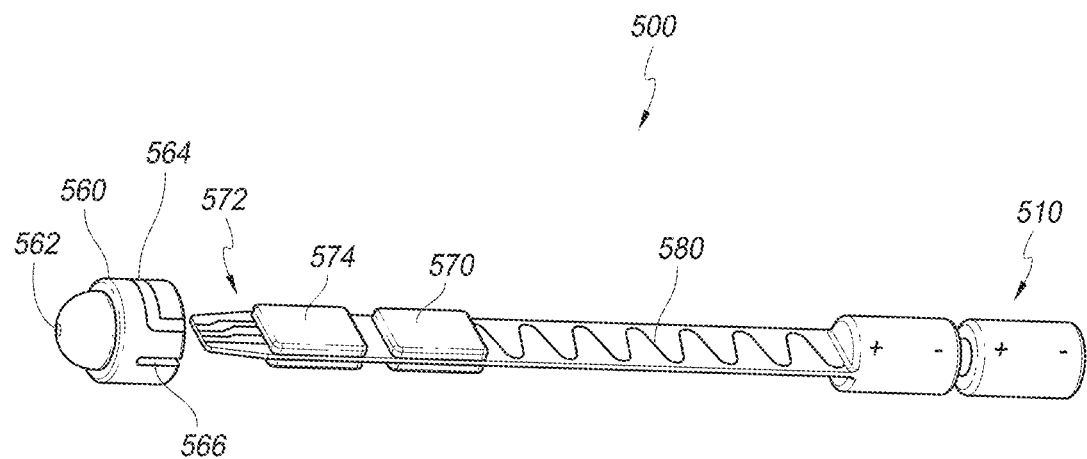
FIG. 5A is a schematic illustration of an implantable intraocular physiological sensor that also enhances drainage of the aqueous humor to help treat glaucoma.
Figure 5B:
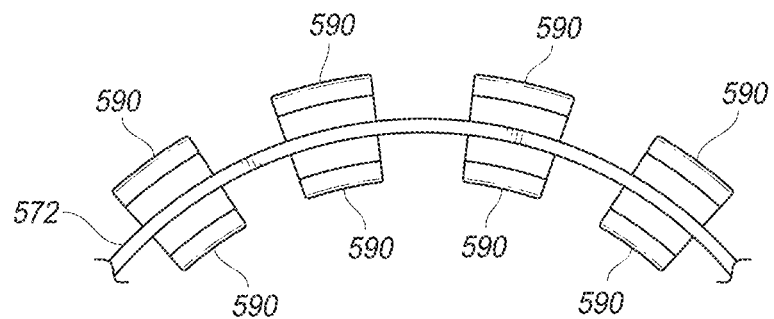
FIG. 5B is a schematic illustration of a circuit carrier member that can be used in the device of FIG. 5A.

FIG. 5A is a schematic illustration of an implantable intraocular physiological sensor 500 that also enhances drainage of the aqueous humor to help treat glaucoma. The physiological sensor 500 includes a physiological characteristic sensing module 560, which could be, for example, electromechanical (such as a capacitive intraocular pressure sensor), electrochemical (such as an amperometric glucose sensor), or optical (such as a fluorescent glucose sensor). The physiological sensor 500 also includes electrochemical fuel cells 510 and various electronic components, such as those described herein. The implantable device can also incorporate onboard memory, logical control (such as microprocessor), software, firmware, digitization, and wireless (radiofrequency or optical) communication. For example, the sensor 500 can include a controller module 570, a signal conditioning and analog-to-digital conversion module 574, a transmitter, etc. The transmitter can include an antenna 580. Some or all of these components can be provided on, or attached to, a carrier member 572. In some embodiments, the carrier member 572 is a circuit board. As discussed further herein, the sensor device 500 may be designed so as to be implantable at or in various anatomical features of the eye. Accordingly, in some embodiments, the carrier member 572 is flexible so as to allow it to satisfactorily conform to a desired anatomical feature. The flexible carrier member 572 can be, for example, a bendable film, such as Kapton™ (polyimide), or comprise a flexible electrical circuit, known as a "flex circuit." FIG. 5B is a schematic illustration of an embodiment of the carrier member 572. As illustrated, the carrier member 572 can be made from a flexible material that allows the carrier member 572 to be deformed into a curvilinear form. Various modules 590 can be mounted on the carrier member 572 at spaced apart intervals on both sides of the carrier member. The modules 590 can also be stacked. The illustrated modules 590 can represent, for example, any of the modules discussed herein (e.g., controller, transmitter, etc.). Signal connection lines such as electrical traces can be formed on the carrier member 572 between the various modules 590. Since the modules 590 are mounted on the carrier member 572 at spaced apart intervals, the combination of the carrier member 572 and the modules 590 can more freely the form to take the shape of the anatomy where it may be implanted.

Although not illustrated, the fuel cells 510 and the carrier member 572, as well as its mounted electronic components, are provided within a fluid channel. The fluid channel can be, for example, a lumen or sheath that is generally cylindrical in shape, though other shapes are possible as well. In some embodiments, the lumen or sheath may have a generally circular, square, or rectangular cross-sectional shape. Square and rectangular cross-sectional shapes may be advantageous in terms of more efficiently being able to fit circuit boards, electronics, etc. within the sheath. Although the sheath may have a generally square or rectangular cross-sectional shape, the corners of the square or rectangular may be rounded in order to ease insertion of the device into, for example, Schlemm's canal or the suprachoroidal space and avoid any damage to the tissue. The fluid channel can have an inlet port that is designed to be in fluid communication with the aqueous humor in the eye when the sensor device is implanted at the intended surgical location. The fluid channel can also have a fluid outlet port that is designed to be in communication with a physiological outflow pathway of the aqueous humor. For example, the outlet port of the fluid channel could be located in the suprachoroidal space or in Schlemm's canal. As the aqueous humor flows through the fluid channel, it can come into contact with the fuel cells 510, thus providing fuel (e.g., glucose dissolved in the aqueous humor) to the fuel cells for the generation of electrical power to operate the sensor device 500. In addition, the sensor device 500 may include a pumping module (not shown) to assist the flow of aqueous through the fluid channel.

In some embodiments, the physiological characteristic sensing module 560 is designed to measure intraocular pressure. Accordingly, in such embodiments, the sensing module 560 may be designed to be located in the anterior chamber of the eye when the device 500 is implanted at the intended destination in the eye. However, as discussed herein, the sensing module 560 may also, or alternatively, be designed to measure other physiological characteristics. As illustrated in FIG. 5A, the sensing module 560 may be a modular component that is detachable from the remainder of the device 500. In the particular illustrated embodiment, the sensing module 560 includes a notched connector 566 that mates with the carrier member 572, which is illustrated as a circuit board. The circuit board also includes electrical lines for communicating signals and power to/from the sensing module 560. The sensing module 560 may also include a connector 564 that mates with the fluid channel, which encloses the carrier member 572, electronic components (e.g., 570, 574, 580) and the fuel cells 510. In particular, the sensing module 560 may be a cap that mounts in one open end of a sheath that serves as the fluid channel. A fluid inlet port 562 can be provided in the sensing module 560 to allow the fluid channel to be in fluid communication with the aqueous humor that surrounds the sensing module.

As discussed herein, the fuel cells 510 can be glucose fuel cells. While two separate fuel cells are illustrated in FIG. 5A, other embodiments may use only one, or some other number, of fuel cells. Glucose-containing aqueous humor can enter the inlet port 562 of the sensing module 560. The aqueous humor can then flow through the fluid channel that is capped by the sensing module, over and around the carrier member 572 and electrical components (e.g., controller module 570, signal conditioning module 574, antenna 580), and then over and around the fuel cells 510 before exiting an outlet port of the fluid channel into a physiological outflow pathway of the aqueous humor.

Based on initial estimates, the glucose fuel cells 510 may be capable of providing approximately 1.5 mW/cm² of surface area. The size and surface area of the fuel cells 510 may vary from application to application depending upon available space. However, an initial estimate for an application where the sensor device 500 is sized to be insertable into the suprachoroidal space is that each of the fuel cells may have a surface area of about $2.9 \times 10^{-3}$ cm². Based on these estimates, each of the fuel cells 510 may produce about $4.3 \times 10^{-3}$ mW. Thus, the combination of the two fuel cells would provide approximately 8 µW. According to initial estimates, the glucose fuel cells 510 would require approximately $4.8 \times 10^{-8}$ moles of glucose per minute in order to generate the 8 µW of power. Based on typical aqueous humor production rates and glucose concentrations in the aqueous, the glucose required by the fuel cells may be a small percentage of the available glucose in the eye (e.g., 0.4%).

In some embodiments, the sensor device 500 is estimated to consume on the order of the few microwatts while performing a measurement and a few picowatts while in a standby low-power mode between measurements. Transmission of the measurements to an external device may require more power, however; perhaps on the order of milliwatts for a short period of time. The precise power demands of the sensor device 500 will depend on numerous factors, including the frequency of measurements, the frequency and required range of data transmission to an external device, etc. However, additional, or fewer, fuel cells can be used depending upon the power requirements of the sensor device 500.

Figure 6:
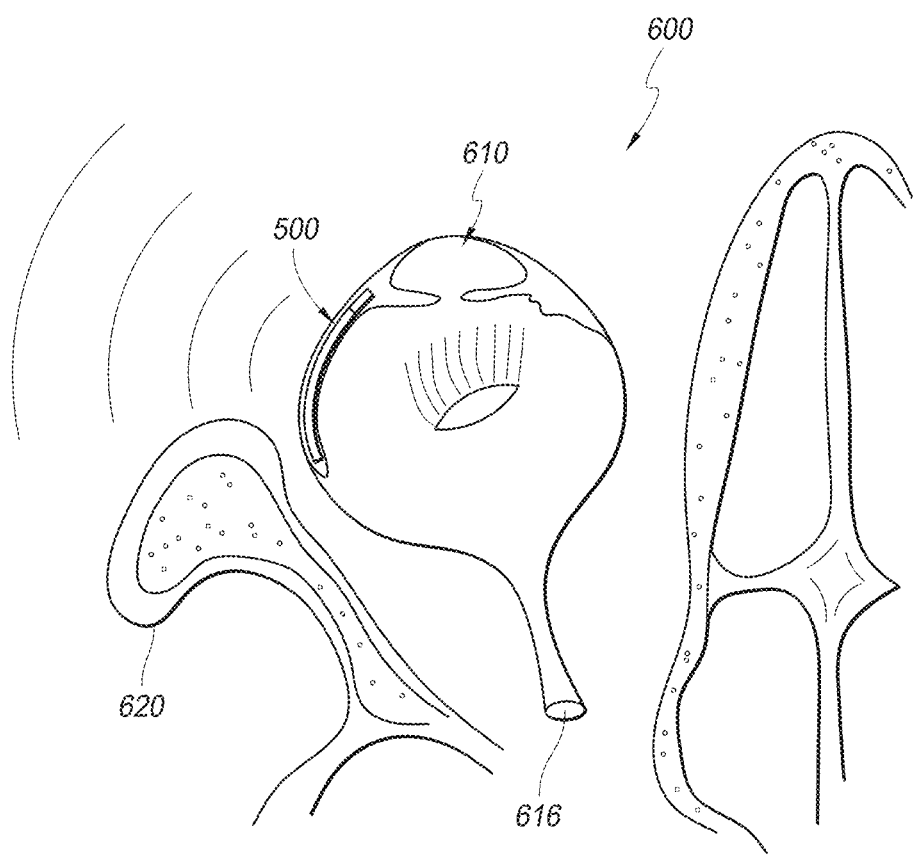
FIG. 6 is a schematic illustration showing the device of FIG. 5A implanted in the eye.

FIG. 6 is a schematic illustration showing the device 500 of FIG. 5A implanted in the eye 600. In particular, FIG. 6 is a superior view of the placement of the sensor device 500, which also shows transmission of electromagnetic waves from the antenna 580. FIG. 6 shows the eye 600, with the anterior chamber 610, the optic nerve 616, and various other anatomical features. The cheekbone 620 is also shown.

In some embodiments, the sensor device 500 is designed to be implanted and/or anchored at least partially in the suprachoroidal space of the eye, as illustrated. In such embodiments, the sensor device 500 may be designed with a generally elongate, cylindrical shape having an outer diameter or dimension of about 0.6 mm or less. In some embodiments, the generally elongate, cylindrical sensor device 500 measures about 3-14 mm in length. In some embodiments, the generally elongate, cylindrical sensor device 500 is about 4 mm in length, has an outer diameter or dimension of about 360 µm and inner diameter or dimension of about 160 µm. The body of the sensor device 500 can be made of various materials, including polyethersulfone (PES). In addition, in some embodiments, the sensor device can be inserted into the anterior chamber via a self-sealing incision at or near the limbus, although it could also be inserted through other openings such as the incision made for cataract surgery, trabeculectomy or other ophthalmic surgical procedures. As already discussed, the sensor device 500 may be inserted such that the sensing module 560 remains in the anterior chamber 610 and in fluid communication with the aqueous humor, while the remaining portion of the device 500 is at least partially located in the suprachoroidal space and/or other portion of the uveoscleral outflow pathway. This placement allows the sensing module 560 to measure intraocular pressure within the anterior chamber 610, while also providing for aqueous drainage through the fluid channel to the suprachoroidal space. In some embodiments, certain components of the sensor device 500, including but not limited to a pressure sensor module and solar cell, could be designed to be insertable into the anterior chamber through a tiny incision as part of a device which would anchor in the suprachoroidal space and subsequently unfurl or enlarge once in position or during positioning. In embodiments with this unfurling or enlarging action, rigid componentry could be mounted to a flexible backer. Other intraocular placements for the sensor device 500 may also be used. For example, the sensor device 500 may be designed to be at least partially inserted into Schlemm's canal. In such embodiments, the sensor device 500 may have, for example, a generally elongate, cylindrical shape with a diameter or dimension of about 150 µm or less. As already discussed, in some embodiments (such as intraocular pressure sensors), the sensor device 500 may be implanted completely within the suprachoroidal space of the eye.

The sensor device 500 may be configured for placement in the supraciliary or suprachoroidal space by making it elongated in one dimension, and narrow or thin in a second and/or third dimension. The elongated dimension may be in the range of 2-25 mm, or more specifically 3-14 mm, while the narrow dimension(s) may be less than 1 mm, and preferably less than 0.6 mm in order to (a) facilitate insertion into the eye through a small gauge insertion needle or cannula; and/or (b) make the device flexible enough to conform to curvature of the anatomy (for example, the curvature of the sclera).

At least one possible advantage of the placement illustrated in FIG. 6 is that the antenna 580 may be largely unobscured by bone, such as the orbital bone or cheekbone 620. Thus, the antenna 580 may only be required to transmit through soft tissue. This can ease the power demands of the transmitter and/or increase the transmission range of the device.

Another advantage of placement of the sensor device 500 in the anterior chamber is that this body location is immunologically privileged, as discussed herein. In other body locations, collagen ("fibrous") encapsulation may occur as a reaction to the presence of a foreign body. Fibrous encapsulation is an obstacle that may reduce the useful life of implanted biomedical sensors. The anterior chamber, in contrast, is one of a very few sites in the body demonstrating "immune privilege" such that a foreign body may be introduced without eliciting an inflammatory immune response. Therefore, a foreign body such as a glucose (or other) biosensor, implanted with minimum trauma and located at least in part within the anterior chamber, may well experience less fibrous encapsulation and a longer useful life than the same biosensor implanted elsewhere in the body.

As discussed herein, the sensor device 500 can be used as part of a system whereby intraocular pressure values measured and temporarily stored by the implanted sensor are read automatically by a monitor, such as a device at a patient's bedside that interrogates the implanted sensor during sleep. In some embodiments, the bedside monitor would interface to, for example, the internet, and automatically send data to a doctor's office for evaluation. This system could include time stamping and temporary storage in memory of intraocular pressure measurements made by the implanted sensor. The sensor measurements could be continuous or intermittent, and the device could be switchable, between active and quiescent states.

Figure 7:
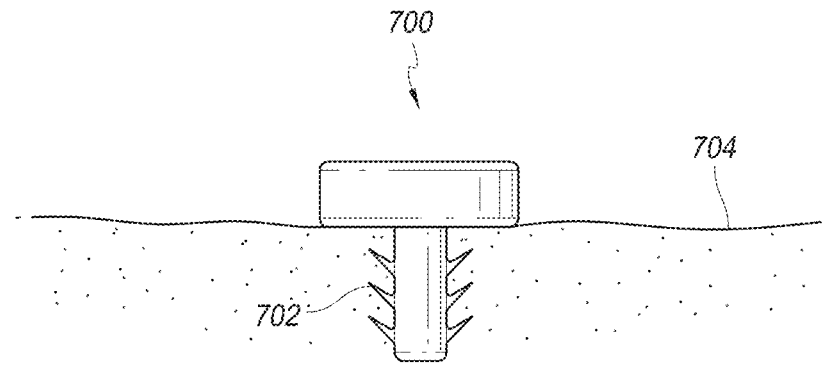
FIG. 7 is a schematic illustration of an implantable intraocular physiological sensor with an anchoring member.

FIG. 7 is a schematic illustration of an implantable intraocular physiological sensor 700 with an anchoring member 702. The anchoring member 702 can be used to fixedly attach the sensor 700 to eye tissue 704, such as eye tissue comprising a physiological outflow pathway for aqueous humor. The anchoring member 702 is illustrated with barbed retention features, but it can include any of many different types of retention features. In addition, the physiological sensors 700 can include any of the features discussed herein with respect to any other sensor device.

Figure 8:
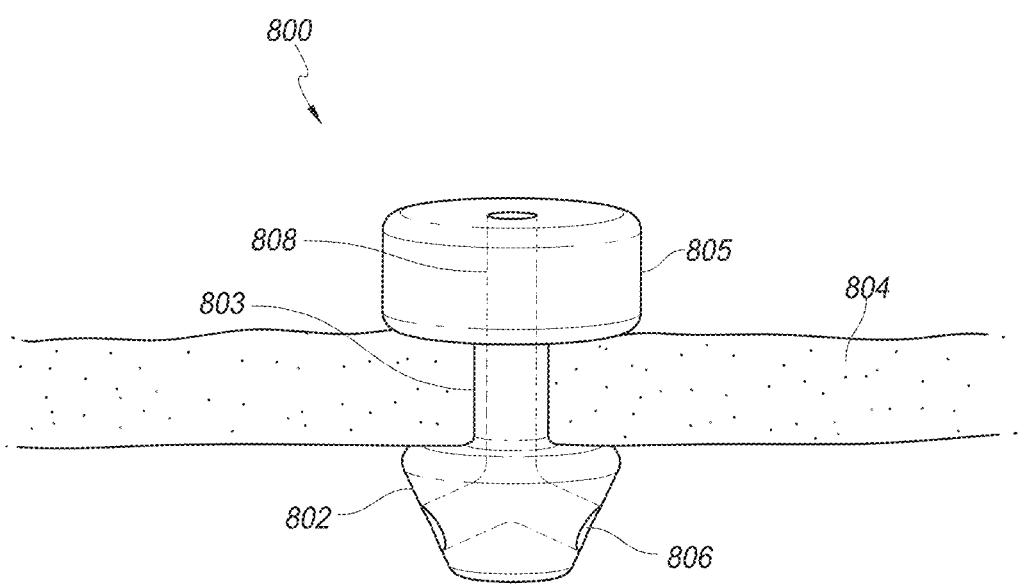
FIG. 8 is a schematic illustration of an implantable intraocular physiological sensor with an anchoring member and a fluid channel.

FIG. 8 is a schematic illustration of an implantable intraocular physiological sensor 800 with an anchoring member 802 and a fluid channel. Thus, the physiological sensor 800 advantageously combines aqueous drainage features with physiological characteristic sensing features. The sensor 800 includes a head portion 805 in which a sensing module, a controller module, a transmitter, a fuel cell, etc. can be included, as discussed herein. The head portion 805 can be attached to the anchoring member 802 by a stem portion 803. In some embodiments, the anchoring member 802 is a tapered bulbous portion that allows penetration into the eye tissue 804, and retention in such eye tissue. In some embodiments, the length of the stem portion 803 corresponds to the thickness of the eye tissue 804 where the sensor device 800 is designed to be located.

The sensor device 800 can also include a fluid channel 808, which is illustrated by dotted lines to indicate that it is an interior feature. In some embodiments, the fluid channel 808 has an inlet port at the head portion 805 of the sensor device 800. The fluid channel 808 can extend from the head portion, which is designed to be in fluid communication with the aqueous humor when the sensor device 800 is implanted, through the stem portion 803, to the anchoring member 802. In some embodiments, the sensor device 800 may include external fluid channels and outlet features, such as grooves. The anchoring member 802 can include one or more fluid outlet ports 806. In some embodiments, the physiological sensor 800 is sized and shaped to be inserted into the anterior chamber of the eye and anchored into eye tissue 804. In one embodiment, the implant is anchored to the trabecular meshwork, thus allowing enhanced drainage of the aqueous humor into Schlemm's canal.

Figure 9:
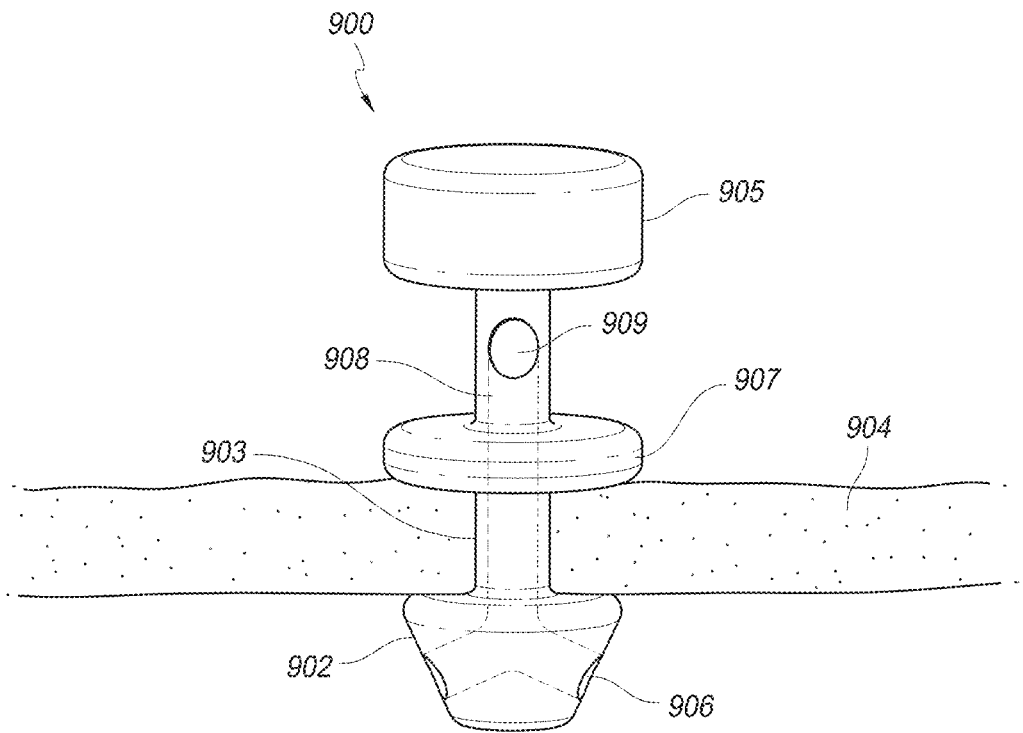
FIG. 9 is a schematic illustration of an implantable intraocular physiological sensor with an anchoring member and a fluid channel that does not pass through an electronics housing portion of the physiological sensor.

FIG. 9 is a schematic illustration of an implantable intraocular physiological sensor 900 with an anchoring member 902 and a fluid channel 908 that does not pass through an electronics housing portion of the physiological sensor. The physiological sensor 900 includes a head portion 905, which in this embodiment, serves as a housing for various electronic components of the sensor (e.g., sensing module, controller module, transmitter, fuel cell, etc.). The head portion 905 is connected to an anchoring member 902 via a stem portion 903.

The stem portion 903 includes one or more fluid inlet ports 909 and a fluid channel 908. The fluid channel 908 extends into the anchoring member 902, which includes one or more fluid outlet ports 906. The stem portion 903 also includes a flange 907 along its length between the head portion 905 and the anchoring member 902. The flange 907, in conjunction with the anchoring member 902, allows the sensor device 900 to be mounted to eye tissue 904 such that the head portion 905 is raised above the tissue 904. The inlet ports 909 of the fluid channel 908 are located in the stem portion 903 between the head portion 905 and the flange 907. Accordingly, the fluid channel 908 need not necessarily pass through the housing (e.g., head portion 905) where electronic components are located. This can be advantageous because locating the fluid channel through the electronics housing may complicate layout of the electronic components within the housing. In the embodiment illustrated in FIG. 9, however, the electronics housing and the fluid channel can be designed substantially independently.

The illustrations in FIGS. 7-10 are schematic in nature. Accordingly, the shape, location, and design of the implants and features of the implants may be different from what is illustrated. For example, the shape and relative sizes of features including but not limited to the head portion, anchoring portion, and flanges can be as illustrated or they may have different shapes. In other embodiments, the cross-sectional shape of the head portion may be circular or polygonal, and the top may be generally flat or curved and it may be larger or smaller in size as compared to the other features of the implant. In other embodiments, an anchor, anchoring portion and/or flange(s) may be of different sizes and shapes, including those disclosed in U.S. Pat. No. 7,857,782, which is hereby incorporated by reference in its entirety. Implants may have more or fewer inlet and/or outlet ports, the inlet and/or outlet ports may be different sizes and/or shapes and at different locations than those illustrated. As stated previously, the sensor device may be configured for placement in the supraciliary or suprachoroidal space by making it elongated in one dimension, and narrow or thin in a second and/or third dimension. The elongated dimension may be in the range of 2-25 mm, while the narrow dimension(s) may be less than 1 mm, and preferably less than 0.5 mm in order to (a) facilitate insertion into the eye through a small gauge insertion needle or cannula; and/or (b) make the device flexible enough to conform to curvature of the anatomy (for example, the curvature of the sclera).

Implants as described herein may include one or more drugs to be delivered to the eye. Devices having drug delivery capabilities allow for a drug to be delivered directly to the eye, and may also allow for targeted delivery to a structure within the eye, such as, for example, the macula, the retina, the ciliary body, the optic nerve, or the vascular supply to certain regions of the eye. Use of a drug eluting implant could also provide the opportunity to administer a controlled amount of drug for a desired amount of time, depending on the pathology. For instance, some pathologies may require drugs to be released at a constant rate for just a few days, others may require drug release at a constant rate for up to several months, still others may need periodic or varied release rates over time, and even others may require periods of no release. Further, implants may serve additional functions once the delivery of the drug is complete. Implants may maintain the patency of a fluid flow passageway within an ocular cavity, they may function as a reservoir for future administration of the same or a different therapeutic agent, or may also function to maintain the patency of a fluid flow pathway or passageway from a first location to a second location, e.g. function as a stent. Conversely, should a drug be required only acutely, an implant may also be made completely biodegradable.

As used herein, "drug" refers generally to one or more drugs that may be administered alone, in combination and/or compounded with one or more pharmaceutically acceptable excipients (e.g. binders, disintegrants, fillers, diluents, lubricants, drug release control polymers or other agents, etc.), auxiliary agents or compounds as may be housed within the implants as described herein. The term "drug" is a broad term that may be used interchangeably with terms such as "therapeutic agent" and "pharmaceutical" or "pharmacological agent" and includes not only so-called small molecule drugs, but also macromolecular drugs, and biologics, including but not limited to proteins, nucleic acids, antibodies and the like, regardless of whether such drug is natural, synthetic, or recombinant. "Drug" may refer to the drug alone or in combination with the excipients described above. "Drug" may also refer to an active drug itself or a prodrug or salt of an active drug.

Following implantation at the desired site within the eye, drug is released from the implant in a targeted and controlled fashion, based on the design of the various aspects of the implant, preferably for an extended period of time. The implant and associated methods disclosed herein may be used in the treatment of pathologies requiring drug administration to the posterior chamber of the eye, the anterior chamber of the eye, or to specific tissues within the eye.

In some embodiments functioning as a drug delivery device alone, the implant is configured to deliver one or more drugs to anterior region of the eye in a controlled fashion while in other embodiments the implant is configured to deliver one or more drugs to the posterior region of the eye in a controlled fashion. In still other embodiments, the implant is configured to simultaneously deliver drugs to both the anterior and posterior region of the eye in a controlled fashion. In yet other embodiments, the configuration of the implant is such that drug is released in a targeted fashion to a particular intraocular tissue, for example, the macula, ciliary body, ciliary processes, ciliary muscles, Schlemm's canal, trabecular meshwork, episcleral veins, lens cortex, lens epithelium, lens capsule, choroid, optic nerve, and/or retina.

In certain embodiments the drug delivery implant may contain one or more drugs which may or may not be compounded with a bioerodible polymer or a bioerodible polymer and at least one additional agent. In still other embodiments, the drug delivery implant is used to sequentially deliver multiple drugs. Additionally, certain embodiments are constructed using different outer shell materials, and/or materials of varied permeability to generate a tailored drug elution profile. Certain embodiments are constructed using different numbers, dimensions and/or locations of orifices in the implant shell to generate a tailored drug elution profile. Certain embodiments are constructed using different polymer coatings and different coating locations on the implant to generate a tailored drug elution profile. Embodiments may elute drug at a constant rate, with a zero-order release profile, or variable elution profile. Some embodiments are designed to stop elution completely or nearly completely for a predetermined period of time (e.g., a "drug holiday") and later resume elution at the same or a different elution rate or concentration. Some such embodiments elute the same therapeutic agent before and after the drug holiday while other embodiments elute different therapeutic agents before and after the drug holiday.

The therapeutic agents utilized with embodiments having drug delivery capabilities, including separate drug delivery implants used in conjunction with a sensor, as well as any implant having a coating comprising a drug may include one or more drugs provided below, either alone or in combination. The drugs utilized may also be the equivalent of, derivatives of, or analogs of one or more of the drugs provided below. The drugs may include but are not limited to pharmaceutical agents including anti-glaucoma medications, ocular agents, antimicrobial agents (e.g., antibiotic, antiviral, antiparasitic, antifungal agents), anti-inflammatory agents (including steroids or non-steroidal anti-inflammatory), biological agents including hormones, enzymes or enzyme-related components, antibodies or antibody-related components, oligonucleotides (including DNA, RNA, short-interfering RNA, antisense oligonucleotides, and the like), DNA/RNA vectors, viruses (either wild type or genetically modified) or viral vectors, peptides, proteins, enzymes, extracellular matrix components, and live cells configured to produce one or more biological components. The use of any particular drug is not limited to its primary effect or regulatory body-approved treatment indication or manner of use. Drugs also include compounds or other materials that reduce or treat one or more side effects of another drug or therapeutic agent. As many drugs have more than a single mode of action, the listing of any particular drug within any one therapeutic class below is only representative of one possible use of the drug and is not intended to limit the scope of its use with the ophthalmic implant system.

As discussed above, the therapeutic agents may be combined with any number of excipients as is known in the art. In addition to the biodegradable polymeric excipients discussed above, other excipients may be used, including, but not limited to, benzyl alcohol, ethylcellulose, methylcellulose, hydroxymethylcellulose, cetyl alcohol, croscarmellose sodium, dextrans, dextrose, fructose, gelatin, glycerin, monoglycerides, diglycerides, kaolin, calcium chloride, lactose, lactose monohydrate, maltodextrins, polysorbates, pregelatinized starch, calcium stearate, magnesium stearate, silicon dioxide, cornstarch, talc, and the like. The one or more excipients may be included in total amounts as low as about 1%, 5%, or 10% and in other embodiments may be included in total amounts as high as 50%, 70%, 90% or more. High amounts of excipient are desirable when the drug is in the form of a microscopic pellet or tablet. Additional disclosure on such tablets may be found in International Patent Application Publication No. WO 2010/135369, the disclosure of which is hereby incorporated by reference in its entirety.

Examples of drugs may include various anti-secretory agents; antimitotics and other anti-proliferative agents, including among others, anti-angiogenesis agents such as angiostatin, anecortave acetate, thrombospondin, VEGF receptor tyrosine kinase inhibitors and anti-vascular endothelial growth factor (anti-VEGF) drugs such as ranibizumab (LUCENTIS®) and bevacizumab (AVASTIN®), pegaptanib (MACUGEN®), sunitinib and sorafenib and any of a variety of small-molecule and transcription inhibitors having anti-angiogenesis effect; classes of known ophthalmic drugs, including: glaucoma agents, such as adrenergic antagonists, including for example, beta-blocker agents such as atenolol propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluroometholone, loteprednol, medrysone, fluocinolone acetonide, triamcinolone acetonide, triamcinolone, triamcinolone acetonide, beclomethasone, budesonide, flunisolide, fluorometholone, fluticasone, hydrocortisone, hydrocortisone acetate, loteprednol, rimexolone and non-steroidal anti-inflammatory agents including, for example, diclofenac, flurbiprofen, ibuprofen, bromfenac, nepafenac, and ketorolac, salicylate, indomethacin, ibuprofen, naxopren, piroxicam and nabumetone; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B and miconazole; antivirals such as idoxuridine trifluorothymidine, acyclovir, gancyclovir, interferon; antimicotics; immune-modulating agents such as antiallergenics, including, for example, sodium chromoglycate, antazoline, methapyriline, chlorpheniramine, cetrizine, pyrilamine, prophenpyridamine; anti-histamine agents such as azelastine, emedastine and levocabastine; immunological drugs (such as vaccines and immune stimulants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor or antagonists thereof (such as those disclosed in U.S. Pat. No. 7,759,472 or U.S. patent application Ser. No. 12/465,051, 12/564,863, or 12/641,270, each of which is incorporated in its entirety by reference herein), transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers such as dorzolamide or betaxolol; compounds that promote blood oxygenation such as erythropoeitin; sodium channels blockers; calcium channel blockers such as nilvadipine or lomerizine; glutamate inhibitors such as memantine nitromemantine, riluzole, dextromethorphan or agmatine; acetylcholinsterase inhibitors such as galantamine; hydroxylamines or derivatives thereof, such as the water soluble hydroxylamine derivative OT-440; synaptic modulators such as hydrogen sulfide compounds containing flavonoid glycosides and/or terpenoids, such as *Ginkgo biloba*; neurotrophic factors such as glial cell-line derived neutrophic factor, brain derived neurotrophic factor; cytokines of the IL-6 family of proteins such as ciliary neurotrophic factor or leukemia inhibitory factor; compounds or factors that affect nitric oxide levels, such as nitric oxide, nitroglycerin, or nitric oxide synthase inhibitors; cannabinoid receptor agonsists such as WIN55-212-2; free radical scavengers such as methoxypolyethylene glycol thioester (MPDTE) or methoxypolyethlene glycol thiol coupled with EDTA methyl triester (MPSEDE); anti-oxidants such as astaxathin, dithiolethione, vitamin E, or metallocorroles (e.g., iron, manganese or gallium corroles); compounds or factors involved in oxygen homeostasis such as neuroglobin or cytoglobin; inhibitors or factors that impact mitochondrial division or fission, such as Mdivi-1 (a selective inhibitor of dynamin related protein 1 (Drp1)); kinase inhibitors or modulators such as the Rho-kinase inhibitor H-1152 or the tyrosine kinase inhibitor AG1478; compounds or factors that affect integrin function, such as the Beta 1-integrin activating antibody HUTS-21; N-acyl-ethanaolamines and their precursors, N-acyl-ethanolamine phospholipids; stimulators of glucagon-like peptide 1 receptors (e.g., glucagon-like peptide 1); polyphenol containing compounds such as resveratrol; chelating compounds; apoptosis-related protease inhibitors; compounds that reduce new protein synthesis; radiotherapeutic agents; photodynamic therapy agents; gene therapy agents; genetic modulators; auto-immune modulators that prevent damage to nerves or portions of nerves (e.g., demyelination) such as glatimir; myelin inhibitors such as anti-NgR Blocking Protein, NgR (310)ecto-Fc; other immune modulators such as FK506 binding proteins (e.g., FKBP51); and dry eye medications such as cyclosporine A, delmulcents, and sodium hyaluronate.

Other therapeutic agents that may be used include: other beta-blocker agents such as acebutolol, atenolol, bisoprolol, carvedilol, asmolol, labetalol, nadolol, penbutolol, and pindolol; other corticosteroidal and non-steroidal anti-inflammatory agents such aspirin, betamethasone, cortisone, diflunisal, etodolac, fenoprofen, fludrocortisone, flurbiprofen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and. Valdecoxib; other immune-modulating agents such as aldesleukin, adalimumab (HUMIRA®), azathioprine, basiliximab, daclizumab, etanercept (ENBREL®), hydroxychloroquine, infliximab (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; anti-fungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-*mycobacterium* agents such as ethambutol, isoniazid, pyrazinamide, rifampin and rifabutin; anti-parasitic agents such as albendazole, mebendazole, thiobendazole, metronidazole, pyrantel, atovaquone, iodoquinaol, ivermectin, paromycin, praziquantel, and trimatrexate; other anti-viral agents, including anti-CMV or anti-herpetic agents such as acyclovir, cidofovir, famciclovir, gangciclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other anti-viral agents such as interferons, ribavirin and trifluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other antibacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprus side, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anti-coagulant agents such as hirudin, aprotinin, argatroban, bivalirudin, desirudin, lepirudin, warfarin and ximelagatran; anti-platelet agents such as abciximab, clopidogrel, dipyridamole, optifibatide, ticlopidine and tirofiban; prostaglandin PDE-5 inhibitors and other prostaglandin agents such as alprostadil, carboprost, sildenafil, tadalafil and vardenafil; thrombin inhibitors; antithrombogenic agents; anti-platelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-fluorouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

Figure 10:
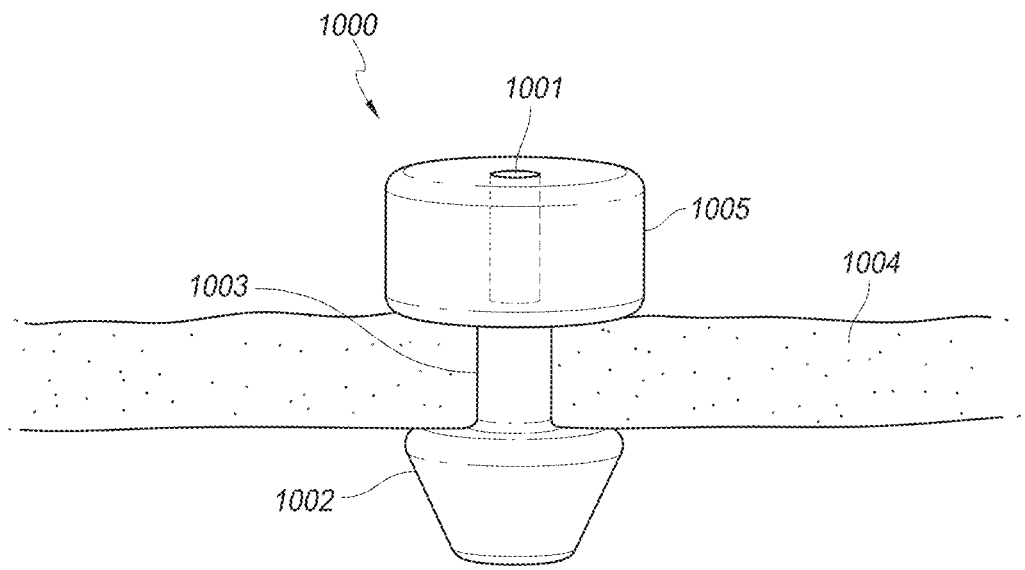
FIG. 10 is a schematic illustration of an implantable intraocular physiological sensor with an anchoring member and a drug repository.

FIG. 10 is a schematic illustration of an implantable intraocular physiological sensor 1000 with an anchoring member 1002 and a drug repository or drug delivery device 1001. The physiological sensor 1000 can include a head portion 1005, which may house various components described herein, such as a sensing module, a controller module, a transmitter, a fuel cell, etc. The head portion 1005 is attached to the anchoring member 1002 by a stem portion 1003. The anchoring member 1002 can be used to mount to the device 1000 in eye tissue, as described herein. The physiological sensor 1000 also includes a drug repository 1001. Although the drug repository or drug delivery device 1001 is illustrated as an opening in the head portion 1005 of the sensor 1000, it can be located at various positions on the device 1000. The drug repository or drug delivery device 1001 can be provided with any of the drugs described herein. In some embodiments, the drug repository or drug delivery device 1001 can either continuously release a drug or release controlled amounts of a drug upon command.

In some embodiments, the physiological sensors described herein can be used to provide a closed monitoring and control system for treating a physiological condition. For example, a target value for a physiological characteristic can be stored in the physiological sensor. The sensor, once implanted in the eye, can then be used to obtain a measured value for the physiological characteristic. The sensor can compare the measured value of the physiological characteristic to the target value of the physiological characteristic and then control an action to reduce the difference between the measured value of the physiological characteristic and the target value of the physiological characteristic. As discussed herein, in some embodiments, the action can be releasing a drug to treat intraocular pressure or regulating the outflow of aqueous humor from the eye.

In some embodiments, the physiological sensor 1000 may be used as a closed continuous IOP monitoring and control system to give a clinician who is managing a glaucoma patient the ability to design and implement an individualized pharmacotherapy regimen that is controlled by the physiological sensor 1000 based on predetermined IOP targets set by the clinician. Generally, a physician managing a glaucoma patient can establish a target level of intraocular pressure which he or she feels is suited to the patient to reduce the risk of disease progression. In selecting the target pressure, the physician may take into account a number of factors, including but not limited to, current/baseline IOP, family history, optic nerve head status, retinal nerve fiber layer evaluation, and visual field effects. Although numerous studies have found that lower pressures reduce the risk of progression, the clinician tends to select a target pressure that strikes an appropriate balance between risk of progression and the side effects and morbidity associated with the interventions required to reach and maintain the target pressure.

With a closed continuous IOP monitoring system, the physician or other user could select a target pressure and program the system to instruct a drug delivery device to administer a pre-defined dose of, for example, a hypotensive medication in response to specific IOP measurement criteria. Additionally, or alternatively, the system could instruct the patient to administer a specific topical medication in response to specific outputs. This allows the system to administer only the amount of drug necessary to consistently maintain IOP at or below the target pressure.

For example, the physician could select a target pressure of 16 mm Hg for a patient. The patient can be implanted (e.g., at the trabecular meshwork) with a device such as intraocular physiological sensor 1000 that continuously administers a therapeutic level of a drug, such as a prostaglandin analogue. The patient can also be implanted with a device in the suprachoroidal space that contains a drug such as an alpha agonist. However, this second drug may only be delivered in the event that the patient's average IOP, as measured by the implanted device, exceeds 18 mm Hg for a set period of time. In another example, a physician may select a target pressure, such as 18 mm Hg. The patient can be implanted with a device in the trabecular meshwork that continuously administers a therapeutic level of a drug, such as a prostaglandin analogue. The implanted monitoring device may communicate to the patient (e.g., via an external device worn by the patient) to administer a topical dose of a drug such as timolol in the event that the patient's average IOP exceeds, for example, 21 mm Hg for a period of time, such as six hours. In another example, a physician may select a target pressure of, for example, 18 mm Hg. The patient can be implanted with a device in the trabecular meshwork that administers a dose of a drug, such as prostaglandin analogue, only when the patient's IOP exceeds the target value for some set period of time.

In addition to the closed continuous IOP monitoring and control system that provides for controlled management of IOP with drugs, a similar closed continuous IOP monitoring and control system could be provided using a stent to manage IOP by regulating the outflow of aqueous humor. In such embodiments, the outflow of the stent and/or the release of a drug can be controlled based upon, for example, intraocular pressure measurements from the physiological sensor in conjunction with a target intraocular pressure value that may be programmed into the sensor by a clinician.

A similar closed continuous monitoring and control system could also be implemented with glucose concentration measurements. For example, a clinician or the patient could set a target glucose level. The implanted intraocular physiological sensor could then monitor glucose concentration levels and control an insulin pump (e.g., with a wireless command interface) to administer insulin based on a comparison between the measured glucose value and the target value. Alternatively, and/or additionally, the physiological sensor could communicate to the patient (e.g., via an external device worn by the patient) a notification to eat or to exercise based on the comparison between the measured glucose value and the target value.

Various embodiments of implants disclosed herein may be implanted by an ab interno procedure or an ab externo procedure. The "ab interno" procedure is herein intended to mean any procedure that creates an opening from the anterior chamber into eye tissue within or forming a boundary of the anterior chamber, usually in a backward direction. This ab interno procedure may be initiated through the scleral wall or cornea wall into the anterior chamber as a first step. The term "ab externo" procedure is herein intended to mean any procedure that creates an opening on the scleral wall and proceeds inwardly toward the anterior chamber. For example, in some "ab externo" procedures, an instrument is passed through or contacts Schlemm's canal before entering trabecular meshwork and approaching the anterior chamber. In some embodiments, ab externo procedures may pass through some or all of the thickness of the scleral wall in order to position a sensor device inside the eye or within the scleral wall. A less-invasive ab externo procedure can be accomplished by tunneling through scleral tissue with a needle or cannula such that the tip of the needle or cannula accesses the anterior chamber or the suprachoroidal space. A sensor device may then be advanced through the needle or cannula to be at least partially located within the anterior chamber, or at least partially located within the suprachoroidal space. After delivery of the sensor device within the eye, the needle or cannula is withdrawn, leaving a self-sealing track through the sclera. Implantation by this method may result in some or all of the sensor device residing within scleral tissue, or between the sclera and the conjunctiva.

Implants may be placed in the eye using an applicator, such as a pusher, guidewire, forceps or other suitable device. The applicator may also be a delivery instrument including but not limited to that disclosed in U.S. Application Publication No. 2002/0133168 or that disclosed in U.S. Pat. No. 7,331,984 which has energy stored in the instrument for delivering one or more implants. The contents of these two documents are hereby incorporated by reference herein in their entireties.

Some embodiments of applicator have trephining capability, wherein a cutting or tissue penetration feature or mechanism forms part of the applicator for purposes of making a hole or opening in eye tissue to allow for implanting and/or securing an implant within the eye. In some embodiments, an implant may be self-trephining such that it makes its own opening.

One embodiment of delivery apparatus includes a handpiece, an elongate body, a holder and a delivery mechanism. In some embodiments, the delivery mechanism is an actuator. The handpiece has a distal end and a proximal end. The elongate body is connected to the distal end of the handpiece. At least the distal portion of the elongate body is sized and configured to be placed through a incision in the sclera or cornea, including at or near the limbus, and into an anterior chamber of the eye. The holder is attached to the distal portion of the elongate tip and is configured to hold and release the implant. The deployment mechanism or actuator is on the handpiece and serves to release the implant from the holder.

In some embodiments, the holder comprises a clamp. The clamp may comprise a plurality of claws configured to exert a clamping force onto at least a portion, usually the proximal portion, of the implant. The holder may also comprise one or more flanges, bumps or other raised regions which utilize friction to hold the device or which engage a corresponding feature on the implant. The holder may also comprise a recessed area or groove at or near the end of the elongate body for retaining an implant or a portion thereof.

In some embodiments, the apparatus further comprises a spring within the handpiece that is configured to be loaded when the one or more implants are being held by the holder, the spring being at least partially unloaded upon actuating the actuator, allowing for release of an implant from the holder.

The deployment mechanism of the delivery apparatus may include a push-pull type plunger, push button or trigger that is operated to cause delivery of an implant, such as by releasing at least some tension from a spring in an actuator mechanism or by causing at least one portion of the delivery device to move relative to another portion of the delivery device and/or an implant. In some embodiments, an actuator may be used to operate a trocar or cutting device to allow for consistent and predictable formation of an opening in eye tissue.

The elongate portion of the device may be flexible or made of a flexible material, such as a flexible wire. The distal portion can have a deflection range, preferably of about 45 degrees from the long axis of the handpiece. The elongate portion of the device may be curved to aid in reaching the anterior angle on the opposite side of the eye from where the opening is made into the anterior chamber. The delivery apparatus can further comprise an irrigation port in the elongate tip.

In some embodiments, the delivery device is adapted to deliver more than one implant into the eye without having to remove the device from the eye between implantations. The implants delivered may be any combination of sensor, drainage device, micropump, drug delivery device and any combination of the foregoing, including devices that may include one or more of the foregoing functions. For example, a delivery device may deliver a sensor-type implant and a combination drainage/drug delivery implant, an IOP sensor and two drainage implants, a IOP sensor and a drug delivery implant, and the like. A device for delivering multiple implants may include an elongate body sized to be introduced into an eye through an incision in the eye and a plurality of implants positioned on or in the elongate body. The elongate body may further comprise an actuator that serially dispenses the implants from the elongate body for implanting in eye tissue.

A method of implanting one or more implants includes inserting an instrument into an eye through an incision, and utilizing the instrument to deliver a first implant into or onto eye tissue at a first location. Other embodiments include utilizing the instrument to deliver a second implant into or onto eye tissue at a second location, without removing the instrument from the eye between the deliveries of the implants.

The incision may be made into the sclera or cornea, including at or near the limbus. In some embodiments, the incision is small so as to be self-sealing. In other embodiments, one or two stitches may be needed to close the opening once the implantation procedure is completed and the delivery device removed from the eye. In some embodiments, the incision is about 1 mm in length. The placement and implantation of the implant(s) may then be performed using a gonioscope or other imaging equipment used in eye surgery, as known in the art.

During implantation, the delivery instrument may be advanced through an insertion site or incision and advanced to desired eye tissue. In some embodiments, the advancement is either transocularly or posteriorly into the anterior chamber angle. Using the anterior chamber angle as a reference point, the delivery instrument can be advanced further in a generally posterior direction to drive the implant into the iris, inward of the anterior chamber angle. The delivery device may be used to implant one or more implants at any location in the eye, including the trabecular meshwork, Schlemm's canal, supraciliary space, suprachoroidal space, and the like.

Optionally, based on the implant structure, the implant may be laid within the anterior chamber angle, taking on a curved shape to match the annular shape of the anterior chamber angle. It is preferred, however, that an implant be secured to tissue, such as by using an anchor, adhesive, friction or other force, or at least not be free to move within the anterior chamber so as to minimize damage to delicate eye tissue such as the corneal endothelium.

Once the delivery device and implant are at the desired location in the eye, an opening may be made in ocular tissue. This may be done, for example, using the distal end of the elongate portion of the delivery device or with a self-trephining implant. The implant is then delivered to the tissue. Delivery may be done by using a deployment mechanism. For example, a pusher tube may be advanced axially toward the distal end of the delivery instrument, such that as the pusher tube is advanced, the implant is also advanced. When the implant is in the desired position, the delivery instrument may be retracted, leaving the implant in the eye tissue. Another implant may then be implanted at another location in the eye, or the delivery device may be removed from the eye.

In other embodiments, the delivery instrument is used to force the implant into a desired position by application of a continual implantation force, by tapping the implant into place using a distal portion of the delivery instrument, or by a combination of these methods. Once the implant is in the desired position, it may be further seated by tapping using a distal portion of the delivery instrument. Alternatively, the device may be implanted by using the actuator to drive an implant into tissue using stored energy, such as from a spring or other energy storage means.

In one embodiment, the implant is affixed to intraocular tissue. In one embodiment, this additional affixation may be performed with a biocompatible adhesive. In other embodiments, one or more sutures may be used or one or more tissue anchors may be used. In another embodiment, the implant is held substantially in place via the interaction of the implant body's outer surface and the surrounding tissue of the anterior chamber angle. A device may also use some combination of the foregoing affixation methods.

Various intraocular physiological sensors are described herein. As further described herein, in some embodiments, such sensors include fluid channels, or other types of shunts. As discussed herein, in some embodiments, the sensor/shunt is inserted from a site transocularly situated from the implantation site. The delivery instrument can be sufficiently long to advance the sensor/shunt transocularly from the insertion site across the anterior chamber to the implantation site. At least a portion of the instrument can be flexible. Alternatively, the instrument can be rigid. The instrument can comprise a plurality of members longitudinally moveable relative to each other. In some embodiments, at least a portion of the delivery instrument is curved or angled. In some embodiments, a portion of the delivery instrument is rigid and another portion of the instrument is flexible.

In some embodiments, the delivery instrument has a distal curvature. The distal curvature of the delivery instrument may be characterized as a radius of approximately 10 to 30 mm, and preferably about 20 mm.

In some embodiments, the delivery instrument has a distal angle. The distal angle may be characterized as approximately 90 to 170 degrees relative to an axis of the proximal segment of the delivery instrument, and preferably about 145 degrees. The angle can incorporate a small radius of curvature at the "elbow" so as to make a smooth transition from the proximal segment of the delivery instrument to the distal segment. The length of the distal segment may be approximately 0.5 to 7 mm, and preferably about 2 to 3 mm.

In some embodiments, the instruments have a sharpened forward end and are self-trephinating, i.e., self-penetrating, so as to pass through tissue without pre-forming an incision, hole or aperture. Alternatively, a trocar, scalpel, or similar instrument can be used to pre-form an incision in the eye tissue before passing the sensor/shunt into such tissue.

For delivery of some embodiments of the ocular sensor/shunt, the instrument can have a sufficiently small cross section such that the insertion site self seals without suturing upon withdrawal of the instrument from the eye. An outer diameter of the delivery instrument preferably is no greater than about 18 gauge and is not smaller than about 32 gauge. For clarification and avoidance of doubt, all delivery devices disclosed herein may be used to deliver any implant disclosed herein, including, but not limited to, a sensor, a shunt or drainage device, and combinations thereof, to any portion of the eye, and preferably those that may be accessed from the anterior chamber. Delivery devices may also deliver more than one device, preferably without having to remove the delivery device from the eye between implantations.

For delivery of some embodiments of the ocular sensor/shunt, the incision in the corneal tissue is preferably made with a hollow needle through which the sensor/shunt is passed. The needle has a small diameter size (e.g., 18 or 19 or 20 or 21 or 22 or 23 or 24 or 25 or 26 or 27 or 28 or 29 or 30 or 31 or 32 gauge) so that the incision is self sealing and the implantation occurs in a closed chamber with or without viscoelastic. A self-sealing incision also can be formed using a conventional "tunneling" procedure in which a spatula-shaped scalpel is used to create a generally inverted V-shaped incision through the cornea. In a preferred mode, the instrument used to form the incision through the cornea remains in place (that is, extends through the corneal incision) during the procedure and is not removed until after implantation. Such incision-forming instrument either can be used to carry the ocular sensor/shunt or can cooperate with a delivery instrument to allow implantation through the same incision without withdrawing the incision-forming instrument. Of course, in other modes, various surgical instruments can be passed through one or more corneal incisions multiple times.

Once into the anterior chamber, a delivery instrument can be advanced from the insertion site transocularly into the anterior chamber angle and positioned at a location near the scleral spur. Using the scleral spur as a reference point, the delivery instrument can be advanced further in a generally posterior direction to drive the sensor/shunt into eye tissue at a location just inward of the scleral spur toward the iris. The placement and implantation of the sensor/shunt can be performed using a gonioscope or other conventional imaging equipment. The delivery instrument preferably is used to force the sensor/shunt into a desired position by application of a continual implantation force, by tapping the sensor/shunt into place using a distal portion of the delivery instrument, or by a combination of these methods. Once the sensor/shunt is in the desired position, it may be further seated by tapping using a distal portion of the delivery instrument.

The delivery instrument can include an open distal end with a lumen extending therethrough. Positioned within the lumen is preferably a pusher tube that is axially movable within the lumen. The pusher tube can be any device suitable for pushing or manipulating the sensor/shunt in relation to the delivery instrument, such as, for example, but without limitation a screw, a rod, a stored energy device such as a spring. A wall of the delivery instrument preferably extends beyond pusher tube to accommodate placement within the lumen of a sensor/shunt. The sensor/shunt can be secured in position. For example, the sensor/shunt can be secured by viscoelastic or mechanical interlock with the pusher tube or wall. When the sensor/shunt is brought into position adjacent the tissue in the anterior chamber angle, the pusher tube is advanced axially toward the open distal end of the delivery instrument. As the pusher tube is advanced, the sensor/shunt is also advanced. When the sensor/shunt is advanced through the tissue and such that it is no longer in the lumen of the delivery instrument, the delivery instrument is retracted, leaving the sensor/shunt in the eye tissue.

Some embodiments can include a spring-loaded or stored-energy pusher system. The spring-loaded pusher preferably includes a button operably connected to a hinged rod device. The rod of the hinged rod device engages a depression in the surface of the pusher, keeping the spring of the pusher in a compressed conformation. When the user pushes the button, the rod is disengaged from the depression, thereby allowing the spring to decompress, thereby advancing the pusher forward.

In some embodiments, an over-the wire system is used to deliver the sensor/shunt. The sensor/shunt can be delivered over a wire. Preferably, the wire is self-trephinating. The wire can function as a trocar. The wire can be superelastic, flexible, or relatively inflexible with respect to the sensor/shunt. The wire can be pre-formed to have a certain shape. The wire can be curved. The wire can have shape memory, or be elastic. In some embodiments, the wire is a pull wire. The wire can be a steerable catheter.

In some embodiments, the wire is positioned within a lumen in the sensor/shunt. The wire can be axially movable within the lumen. The lumen may or may not include valves or other flow regulatory devices.

In some embodiments, the delivery instrument comprises a trocar. The trocar may be angled or curved. The trocar can be rigid, semi-rigid or flexible. In embodiments where the trocar is stiff, the sensor/shunt can be, but need not be relatively flexible. The diameter of the trocar can be about 0.001 inches to about 0.01 inches. In some embodiments, the diameter of the trocar is 0.001, 0.002, 0.004, 0.005, 0.006, 0.007, 0.008, 0.009, or 0.01 inches.

In some embodiments, delivery of the sensor/shunt is achieved by applying a driving force at or near the distal end of the sensor/shunt. The driving force can be a pulling or a pushing applied generally to the end of the sensor/shunt.

The instrument can include a seal to prevent aqueous humor from passing through the delivery instrument and/or between the members of the instrument when the instrument is in the eye. The seal can also aid in preventing backflow of aqueous humor through the instrument and out the eye. Suitable seals for inhibiting leakage include, for example, an o-ring, a coating, a hydrophilic agent, a hydrophobic agent, and combinations thereof. The coating can be, for example, a silicone coat such as MDX™ silicone fluid. In some embodiments, the instrument is coated with the coating and a hydrophilic or hydrophobic agent. In some embodiments, one region of the instrument is coated with the coating plus the hydrophilic agent, and another region of the instrument is coated with the coating plus the hydrophobic agent. The delivery instrument can additionally comprise a seal between various members comprising the instrument. The seal can comprise a hydrophobic or hydrophilic coating between slip-fit surfaces of the members of the instrument. The seal can be disposed proximate of the drainage sensor/shunt when carried by the delivery instrument. Preferably, the seal is present on at least a section of each of two devices that are machined to fit closely with one another.

In some embodiments, the delivery instrument can include a distal end having a beveled shape. The delivery instrument can include a distal end having a spatula shape. The beveled or spatula shape can have a sharpened edge. The beveled or spatula shape can include a recess to contain the sensor/shunt. The recess can include a pusher or other suitable means to push out or eject the sensor/shunt.

The delivery instrument further can be configured to deliver multiple shunts. In some embodiments, when multiple shunts are delivered, the shunts can be arranged in tandem, as described in greater detail below.

For delivery of some embodiments of the ocular sensor/shunt, the implantation occurs in a closed chamber with or without viscoelastic. The shunts may be placed using an applicator, such as a pusher, or they may be placed using a delivery instrument having energy stored in the instrument, such as disclosed in U.S. Patent Publication 2004/0050392, filed Aug. 28, 2002, the entirety of which is incorporated herein by reference and made a part of this specification and disclosure. In some embodiments, fluid may be infused through the delivery instrument or another instrument used in the procedure to create an elevated fluid pressure at the distal end of the sensor/shunt to ease implantation.

In some embodiments, the sensor/shunt is implanted through the fibrous attachment of the ciliary muscle to the sclera. This fibrous attachment zone extends about 0.5 mm posteriorly from the scleral spur, as shown between the two arrows (1020) in FIG. 11.

In some embodiments it is desirable to deliver the sensor/shunt ab interno across the eye, through a small incision at or near the limbus. The overall geometry of the system makes it advantageous that the delivery instrument incorporates a distal curvature, or a distal angle. In the former case, the sensor/shunt can be flexible to facilitate delivery along the curvature or can be more loosely held to move easily along an accurate path. In the latter case, the sensor/shunt can be relatively rigid. The delivery instrument can incorporate a sensor/shunt advancement element (e.g. pusher) that is flexible enough to pass through the distal angle.

In some embodiments, during clinical use, the sensor/shunt and delivery instrument can be advanced together through the anterior chamber 32 from an incision at or near the limbus, across the iris, and through the ciliary muscle attachment until the sensor/shunt outlet portion is located in the uveoscleral outflow pathway (e.g. exposed to the suprachoroidal space 34 defined between the sclera 38 and the choroid 40). The operator can then simultaneously push on a pusher device while pulling back on the delivery instrument, such that the sensor/shunt outlet portion maintains its location in the uveoscleral outflow pathway. The sensor/shunt is released from the delivery instrument, and the delivery instrument is retracted proximally. The delivery instrument then can be withdrawn from the anterior chamber through the incision.

In some embodiments, a viscoelastic can be injected into the suprachoroidal space to create a chamber or pocket between the choroid and sclera which can be accessed by a sensor/shunt. Such a pocket could expose more of the choroidal and scleral tissue area, and increase uveoscleral outflow, causing a lower IOP. In some embodiments, the viscoelastic material can be injected with a 25 or 27 G cannula, for example, through an incision in the ciliary muscle attachment or through the sclera (e.g. from outside the eye). The viscoelastic material can also be injected through the sensor/shunt itself either before, during or after implantation is completed.

In some embodiments, a hyperosmotic agent can be injected into the suprachoroidal space. Such an injection can delay IOP reduction. Thus, hypotony can be avoided in the acute postoperative period by temporarily reducing choroidal absorption. The hyperosmotic agent can be, for example glucose, albumin, HYPAQUE™ medium, glycerol, or poly (ethylene glycol). The hyperosmotic agent can breakdown or wash out as the patient heals, resulting in a stable, acceptably low IOP, and avoiding transient hypotony.

Figure 11:
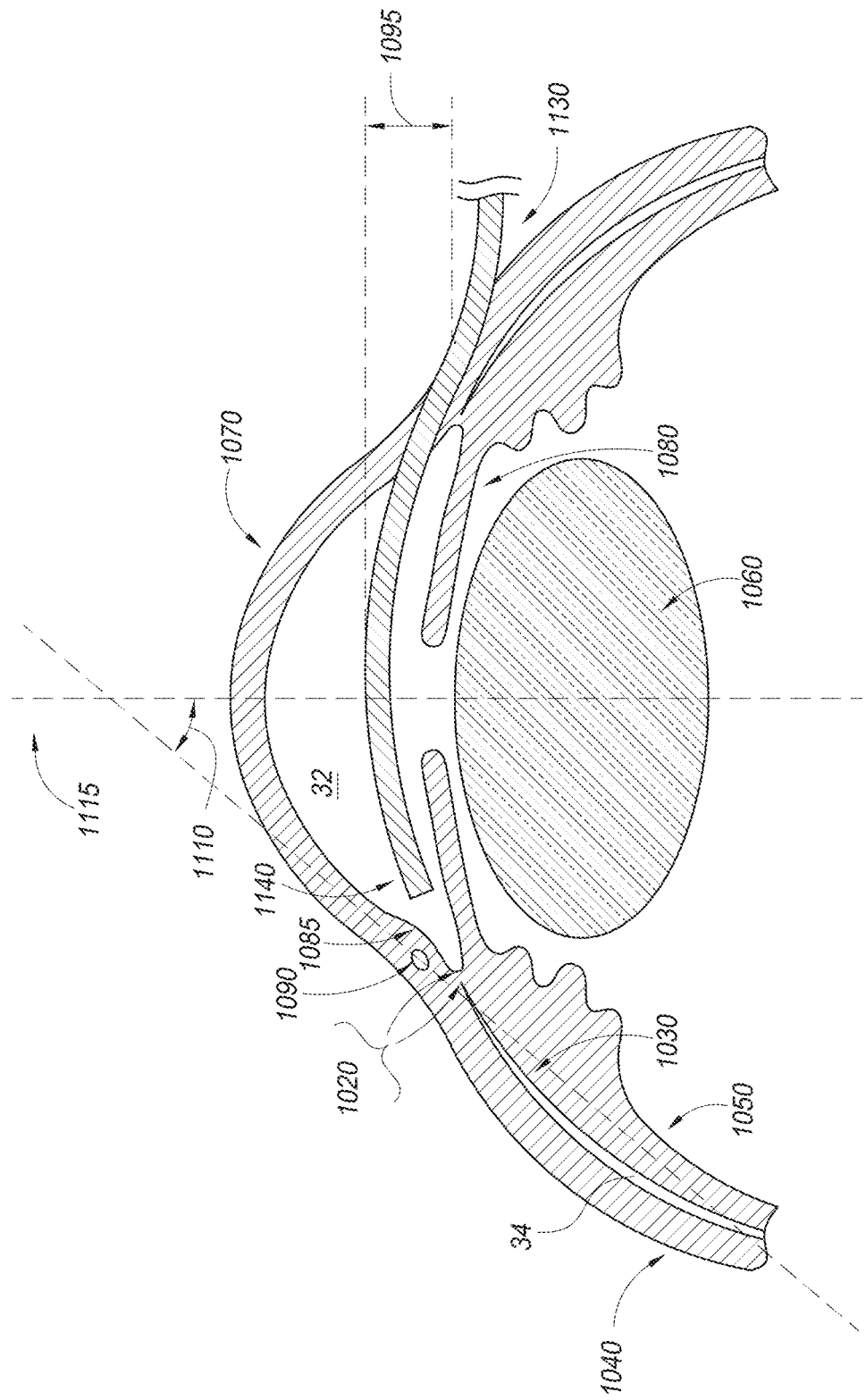
FIG. 11 illustrates a schematic cross-sectional view of an eye with a delivery device being advanced across the anterior chamber.

FIG. 11 shows a meridional section of the anterior segment of the human eye and schematically illustrates another embodiment of a delivery instrument 1130 that can be used with embodiments of shunts described herein. In FIG. 11, arrows 1020 show the fibrous attachment zone of the ciliary muscle 1030 to the sclera 1040. The ciliary muscle is part of the choroid 1050. The suprachoroidal space 34 is the interface between the choroid and the sclera. Other structures in the eye include the lens 1060, the cornea 1070, the anterior chamber 32, the iris 1080, and Schlemm's canal 1090.

In some embodiments, it is desirable to implant a sensor/shunt through the fibrous attachment zone, thus connecting the anterior chamber to the uveoscleral outflow pathway, in order to reduce the intraocular pressure in glaucomatous patients. In some embodiments, it is desirable to deliver the sensor/shunt with a device that traverses the eye internally (ab interno), through a small incision in the limbus.

The delivery instrument/sensor/shunt assembly may be passed between the iris and the cornea to reach the iridocorneal angle. Therefore, the height of the delivery instrument/sensor/shunt assembly (dimension 1095 in FIG. 11) preferably is less than about 3 mm, and more preferably less than 2 mm.

The suprachoroidal space between the choroid and the sclera generally forms an angle 1110 of about 55 degrees with the optical axis 1115 of the eye. This angle, in addition to the height requirement described in the preceding paragraph, are features to consider in the geometrical design of the delivery instrument/sensor/shunt assembly.

Figure 12:
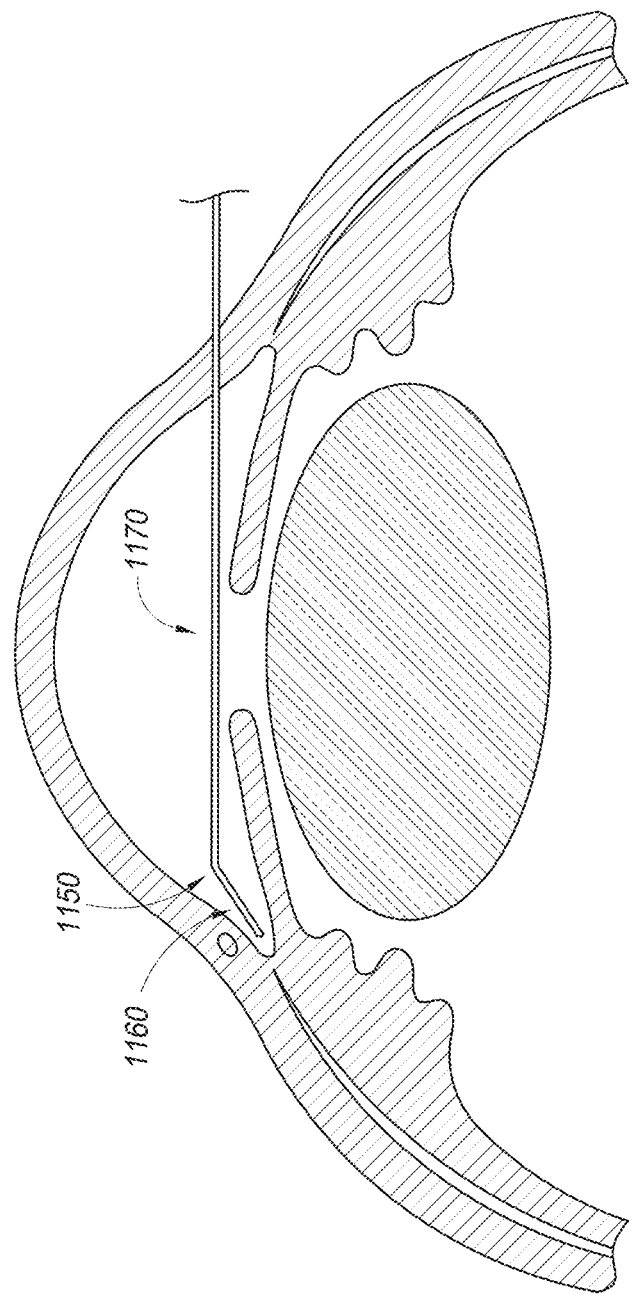
FIG. 12 illustrates a schematic cross-sectional view of an eye with a delivery device being advanced across the anterior chamber.

The overall geometry of the system makes it advantageous that the delivery instrument 1130 incorporates a distal curvature 1140, as shown in FIG. 11, or a distal angle 1150, as shown in FIG. 12. The distal curvature (FIG. 11) is expected to pass more smoothly through the corneal or scleral incision at the limbus. However, the sensor/shunt preferably is curved or flexible in this case. Alternatively, in the design of FIG. 12, the sensor/shunt may be mounted on the straight segment of the delivery instrument, distal of the "elbow" or angle 1150. In this case, the sensor/shunt may be straight and relatively inflexible, and the delivery instrument can incorporate a delivery mechanism that is flexible enough to advance through the angle. In some embodiments, the sensor/shunt is a rigid tube, provided that the sensor/shunt is no longer than the length of the distal segment 1160.

The distal curvature 1140 of delivery instrument 1130 may be characterized as a radius of approximately 10 to 30 mm, and preferably about 20 mm. The distal angle of the delivery instrument depicted in FIG. 12 may be characterized as approximately 90 to 170 degrees relative to an axis of the proximal segment 1170 of the delivery instrument, and preferably about 145 degrees. The angle incorporates a small radius of curvature at the "elbow" so as to make a smooth transition from the proximal segment 1170 of the delivery instrument to the distal segment 1160. The length of the distal segment 1160 may be approximately 0.5 to 7 mm, and preferably about 2 to 3 mm.

Figure 13:
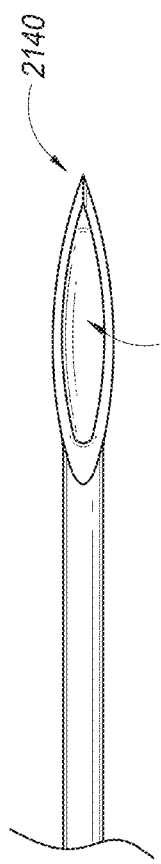
FIG. 13 illustrates a delivery device in accordance with embodiments disclosed herein.
Figure 14A:
FIGS. 14A-B illustrate side views of the delivery device of FIG. 13.
Figure 14B:

FIGS. 13, 14A and 14B show an example of a delivery instrument for a sensor/shunt. In some embodiments, the sensor/shunt is delivered through a needle with a cutting tip 2140. The sensor/shunt can be loaded inside of the shaft of the needle for delivery through the eye. The needle can be curved on the side of the needle opposite to the beveled opening 2150, as illustrated in FIG. 14A. This allows the curved part of the needle to take a "downward" direction without appreciably affecting the effective height of the device. This geometry can be advantageous for passage through the anterior chamber between the iris and the cornea. At the same time, the curve permits the sharp tip of the needle to follow the angle of the ciliary muscle/sclera interface (angle 1110 shown in FIG. 11). Further, the design of the curved tip as shown in FIG. 14A can limit the depth of the dissection of the ciliary muscle from the sclera to the minimum depth necessary to cut through the fibrous attachment tissue. This depth is estimated to be less than about 0.5 mm. In addition, the curvature of the tip act as a baffle to redirect the sensor/shunt as it is pushed distally outward through the needle. In other embodiments, the needle cutting tip is straight, as illustrated in FIG. 14B.

Figure 15:
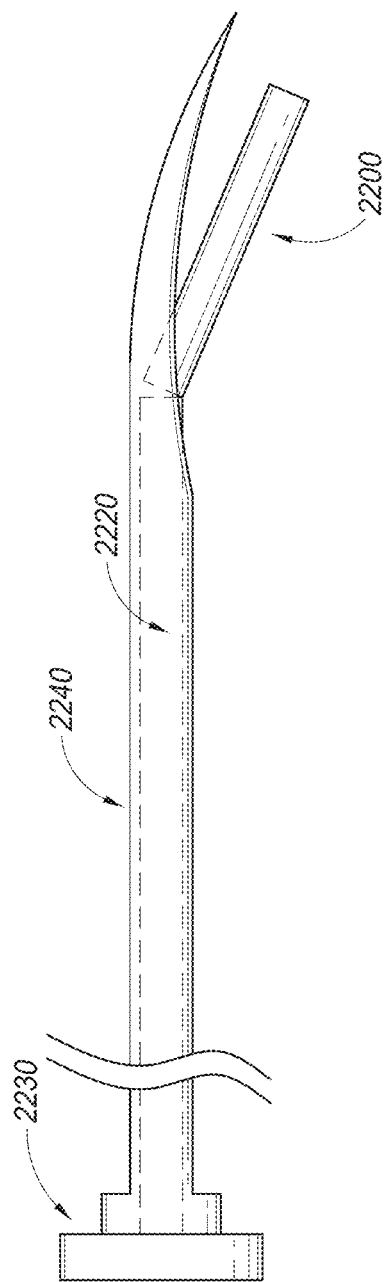
FIG. 15 illustrates a delivery device in accordance with embodiments disclosed herein.

FIG. 15 shows another embodiment of a system that can be used to perform a variety of methods or procedures. The sensor/shunt 2200 is deflected "downward" at an angle that parallels the suprachoroidal space. The depth of insertion can be determined by the length of the pushrod 2220, whose travel can be limited by the stop 2230. It is preferred that the pushrod ends at the proximal edge of the opening of the needle 2240. In this way, the sensor/shunt will not be pushed below the anterior surface of the ciliary muscle.

Figure 16:
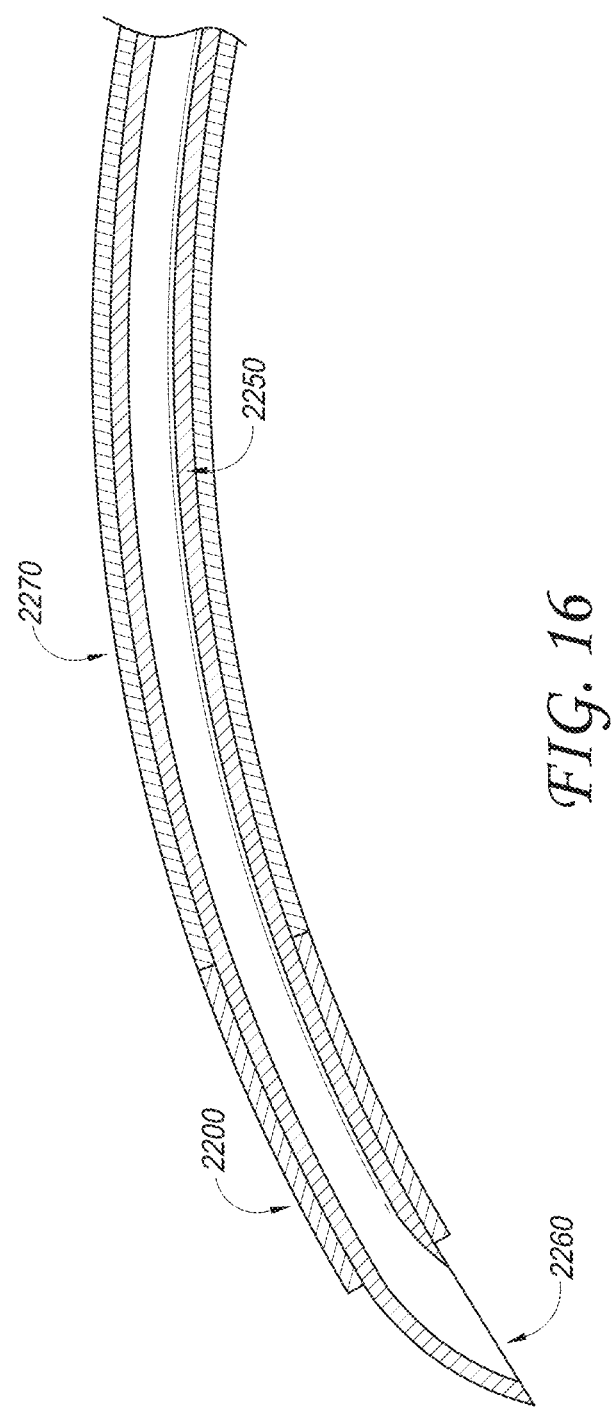
FIG. 16 illustrates a cross-sectional view of an embodiment of a delivery device.

FIG. 16 shows another embodiment of a system that can be used to perform a variety of methods or procedures. In the illustrated embodiment, the sensor/shunt 2200 is mounted on a curved or angled shaft 2250. In some embodiments, both the sensor and the shunt are mounted on the shaft. In other embodiments, while the sensor may be connected to the shunt, only the shunt is mounted on the shaft (e.g., the sensor may be tethered to the shunt, which is mounted on the shaft). The shaft 2250 can be tubular (as shown), or solid and the distal end 2260 can be sharpened. The sensor/shunt 2200 can be curved with approximately the same radius as the delivery device, so that the sensor/shunt can be relatively stiff and still slide along the shaft. In some embodiments, a pusher tube 2270 causes the sensor/shunt to slide distally along the shaft and be released. In operation in some embodiments, the sharpened end 2260 makes an incision in the fibrous tissue attaching the ciliary muscle and the sclera. In some embodiments, the distance between the sharpened tip 2260 and the distal end of the sensor/shunt determines how deeply the tissue may be incised. After making the cut, the operator can advance the pusher tube 2270 while holding the mounting shaft 2250 fixed. This action causes the sensor/shunt 2200 to be advanced into the incision. The distance of sensor/shunt advance can be determined by the length of the pusher tube 2270, whose travel can be limited by a stop, as depicted in FIG. 15.

Further embodiments of the invention incorporate injection of viscoelastic through the sensor/shunt or through the shaft 2250 in order to accomplish posterior dissection of the suprachoroidal tissue, thereby creating a volumetric chamber or reservoir for aqueous humor. In addition or in the alternative, therapeutic agents (e.g., a hyperosmatic agent) can be delivered into the suprachoroidal space through the sensor/shunt 2220 or through the shaft 2250.

Figure 17:
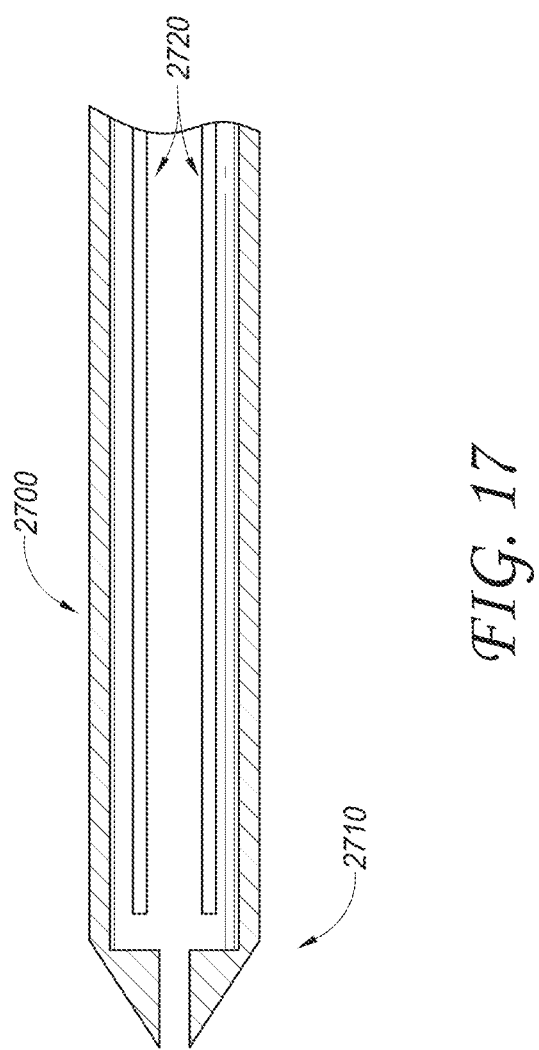
FIG. 17 illustrates a cross-sectional view of an embodiment of a delivery device.

FIG. 17 shows another embodiment of a system that can be used to perform a variety of methods or procedures. Delivery of the sensor/shunt 2700 is achieved by applying a driving force at or near the distal end 2710 of the sensor/shunt 2700 using, for example, a pusher 2720. The driving force can be a pushing force applied to the distal end 2710 of the sensor/shunt 2700. The delivery device alternatively can extend through or around the sensor/shunt to supply a pulling force to draw the sensor/shunt through tissue.

Figure 18:
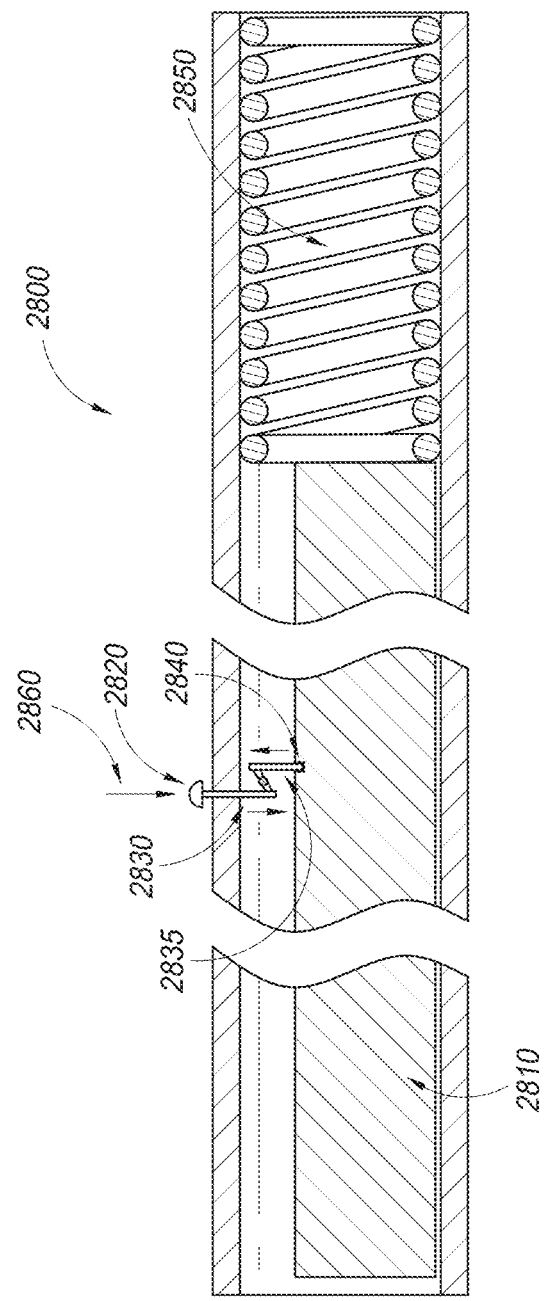
FIG. 18 illustrates a cross-sectional view of an embodiment of a delivery device.

FIG. 18 shows another embodiment of a system 2800 that can be used to perform a variety of methods or procedures. A spring-loaded pusher system 2800 can be used for delivery of a sensor/shunt. The spring-loaded pusher 2810 preferably includes a button 2820 operably connected to a hinged rod device 2830. The distal portion 2835 of the hinged rod device 2830 engages a depression 2840 in the surface of the pusher 2810, keeping the spring 2850 of the pusher 2810 in a compressed conformation. When the user pushes downwards 2860 on the button 2820, the distal portion 2835 of the hinged rod device 2830 is disengaged from the depression 2840, thereby allowing the spring 2850 to decompress, thereby advancing the pusher 2810 forward.

Figure 19:
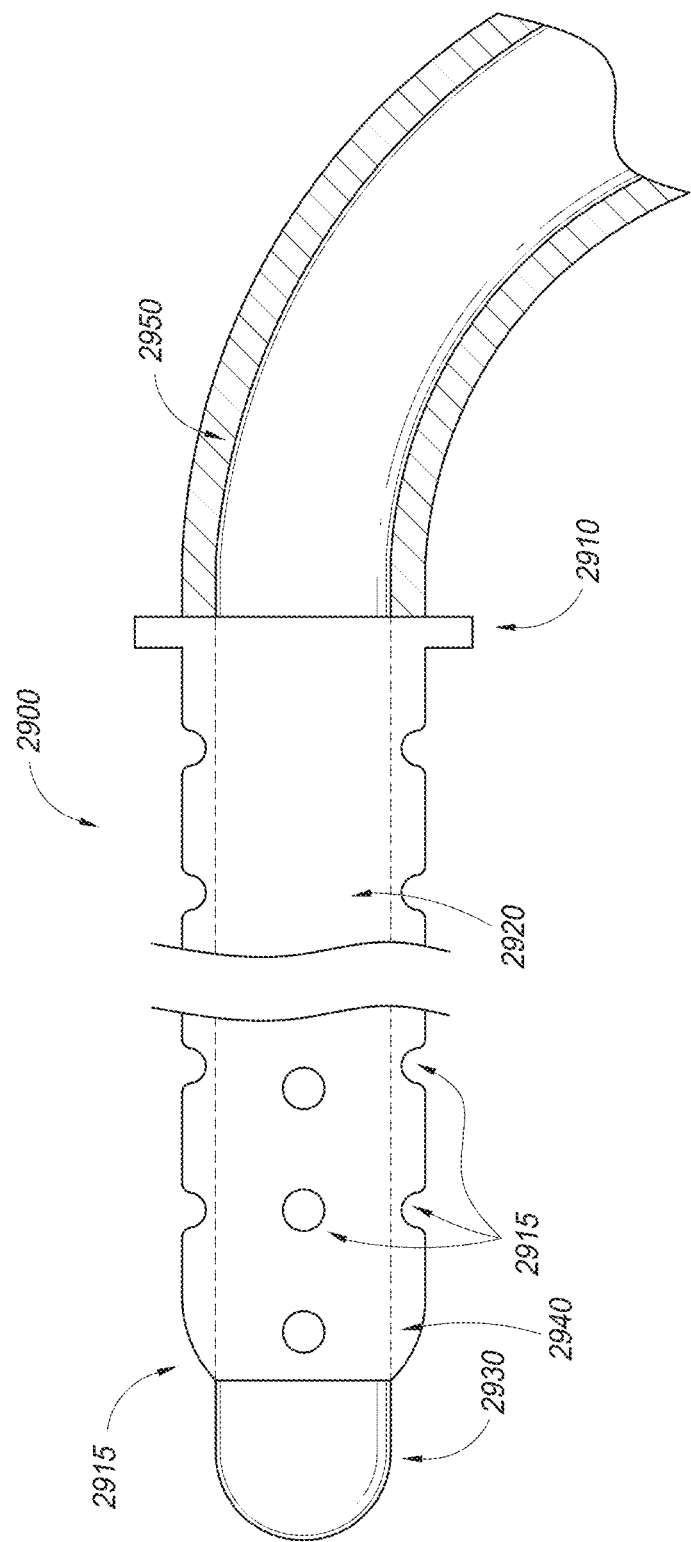
FIG. 19 illustrates a cross-sectional view of an embodiment of a delivery device and an associated sensor/shunt.

FIG. 19 shows another embodiment of a system that can be used to perform a variety of methods or procedures. In the illustrated embodiment, an over-the-wire system 2920 is used to deliver the sensor/shunt 2900. In some embodiments, both the sensor and the shunt are mounted on the wire. In other embodiments, while the sensor may be tethered or otherwise connected to the shunt, only the shunt portion is mounted on the wire. Such embodiments may be advantageous because the sensor portion may not need to have a passage through which the wire can be threaded, and this may simplify design of the sensor and layouts of electronic components. The sensor/shunt 2900 can have a generally rounded distal portion 2915 at the distal end. The radius of the distal portion can be about 70 to about 500 microns. The distal portion 2915 can gradually increase in cross-sectional size towards the proximal direction, preferably at a generally constant taper or radius or in a parabolic manner as shown.

In some embodiments, the implant comprises one or more openings 2905 communicating with an interior chamber, or lumen, within the implant. Preferably, the edges of the openings are rounded as shown. In addition or in the alternative, the implant can include other exterior surface irregularities (e.g., annular grooves) to anchor the implant, as described above.

In some embodiments the sensor/shunt can have a flange 2910 at a proximal portion of the implant. Preferably, the flange has sharp edges and corners as shown. The sharp edges and corners tend to inhibit cell proliferation near the influent end of the implant.

The wire or similar elongated structure 2920 can function as a trocar. Preferably, the wire 2920 is self-trephinating. The radius of the tip of the distal portion 2930 of the wire 2920 can be about 10 to about 500 microns. In some embodiments, the radius of the tip of the distal portion 2930 of the wire 2920 can be about 70 to about 200 microns. The distal portion 2930 of wire 2920 can increase in cross-sectional size towards the proximal direction. In some embodiments, the increase can be in a parabolic manner. In the depicted embodiment, the wire 2920 has a distal portion 2930 having a gradual increase in cross-sectional size in a parabolic manner towards the proximal direction. The wire 2920 can have a rounded distal tip of the distal portion 2930. In other embodiments, the distal portion can be tapered. The wire can be superelastic, flexible, or relatively inflexible with respect to the sensor/shunt. The wire can be pre-formed to have a certain shape. The wire can be curved. The wire can have shape memory, or be elastic. In some embodiments, the wire is a pull wire. The wire can be a steerable catheter.

In some embodiments, a pusher 2950 can be used in conjunction with the wire 2920 to aid in delivery of the sensor/shunt 2900. The pusher 2950 can be used to hold the sensor/shunt 2900 in place as the wire 2920 is withdrawn proximally after the sensor/shunt 2900 has been delivered to a desired location.

The pusher 2950, trocar 2920 and implant 2900 preferably are sized to fit and move (e.g., slide) within an outer sheath or needle. The needle preferably includes a sharpened distal end to penetrate tissue (e.g., corneal tissue) when accessing the anterior chamber of the eye.

Figure 20:
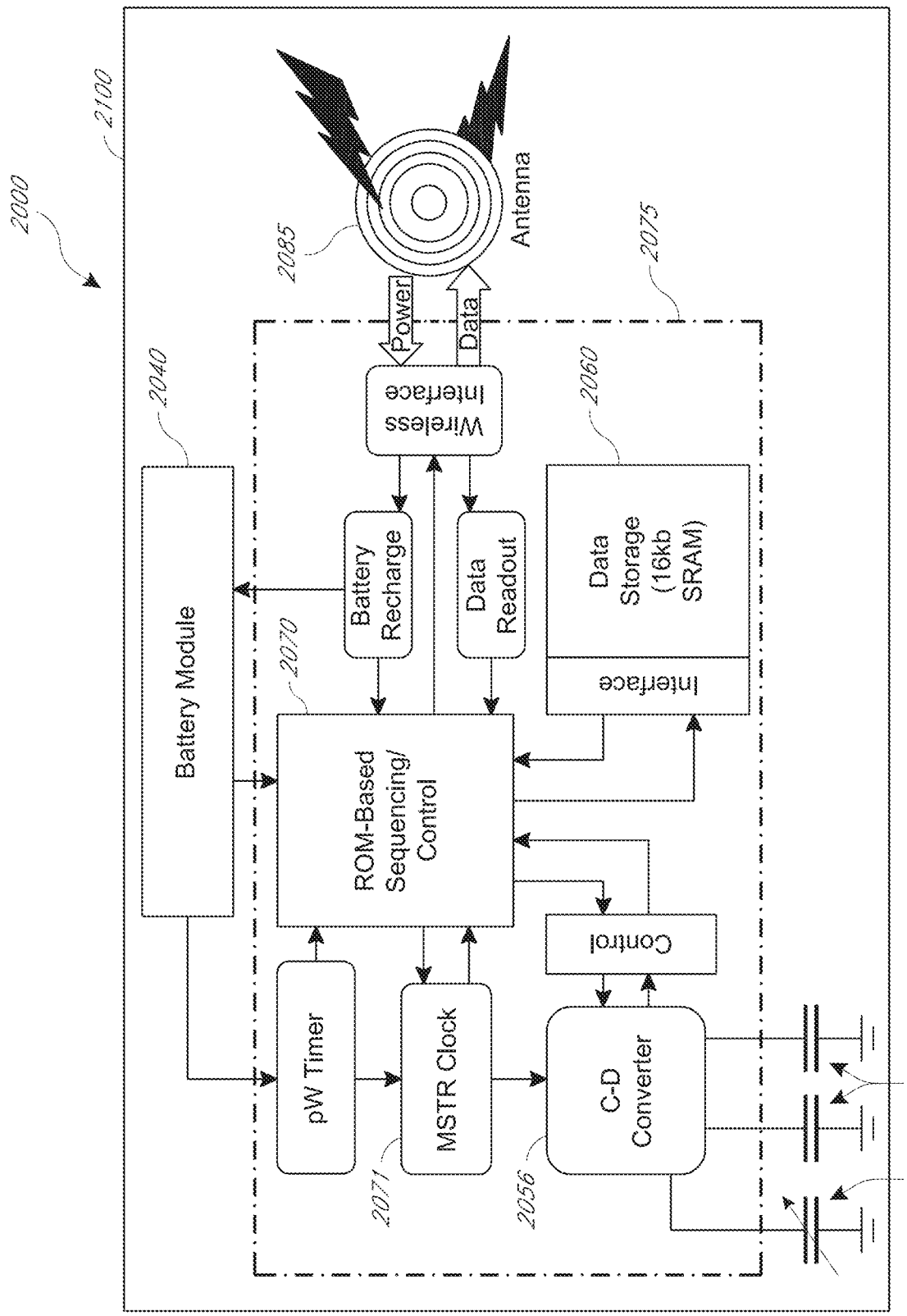
FIG. 20 is a block diagram of an example embodiment of an intraocular pressure sensor.

FIG. 20 is a block diagram of an example embodiment of an intraocular pressure sensor 2000. The intraocular pressure sensor 2000 can include any of the components or features described herein with respect to any other physiological sensor. However, no component or feature should necessarily be understood as being required in the intraocular pressure sensor 2000 unless explicitly stated otherwise. In addition, any of the implantation techniques and tools described herein can be used for implanting the intraocular pressure sensor 2000 at the desired location within the eye, and any sensing, control, and/or treatment method disclosed herein with respect to any other sensor can be used with the intraocular pressure sensor 2000.

In some embodiments, the intraocular pressure sensor 2000 includes a housing assembly 2100 (described herein with respect to FIGS. 21-29), a pressure sensing module 2050, a wireless transmitter/antenna 2085, a controller module 2070, a measurement storage module 2060, and a battery 2040. Each of these components is not necessarily required in every embodiment of the intraocular pressure sensor 2000, however. Further, the intraocular pressure sensor 2000 can also include other components. In some embodiments, some or all of the components of the intraocular pressure sensor 2000 are provided as part of an integrated circuit 2075 (illustrated as the dashed box in FIG. 20) on a chip, though some components can also be provided as discrete components with, for example, electrical connections to the integrated circuit 2075.

In some embodiments, the pressure sensing module 2050 includes a capacitor whose capacitance varies in response to the pressure of the medium where the module is located. In some embodiments, the pressure sensing module 2050 includes a microelectromechanical system (MEMS). For example, as discussed further herein, the pressure sensing module 2050 can include a fixed capacitor plate in proximity to a movable membrane or diaphragm. The distance, and/or contact, between the movable membrane and the fixed capacitor plate varies in response to the pressure applied by, for example, the aqueous humor when the intraocular pressure sensor 2000 is implanted within the eye. This is detected as a change in capacitance of the MEMS device. In some embodiments, the pressure sensing module 2050 is a contact-mode sensor that is capable of measuring intraocular pressure from about 3 mmHg to about 50 mmHg with about ±0.5 mmHg resolution. In some embodiments, the cavity underneath the movable membrane or diaphragm is sealed under vacuum, and the pressure sensing module responds over the range of approximately 600 to 900 mmHg absolute pressure. In such embodiments, ambient pressure can be measured independently outside the body and subtracted from the absolute sensor pressure to yield the intraocular pressure. In some embodiments, the signal (capacitance) varies in an approximately linear fashion relative to the intraocular pressure. In one example, the capacitance may increase from approximately 5 picofarads (pF) to approximately 20 pF over the approximately linear range of pressure.

In some embodiments, the pressure sensing module 2050 is electrically connected to a capacitance-to-digital converter 2056 that outputs a value which is indicative of the capacitance of the pressure sensing module 2050, and, therefore, the detected pressure. This value can be provided to the control module 2070. In some embodiments, the intraocular pressure sensor also includes one or more reference capacitors 2052. The reference capacitor 2052 can also be connected to the capacitance-to-digital converter 2056, and can be used to provide a reference value for calibration and/or temperature compensation.

Pressure measurements from the pressure sensing module 2050 can be stored in the measurement storage module 2060. In some embodiments, the measurement storage module 2060 is a solid-state memory that is provided on an integrated circuit 2075 and is communicatively coupled to, for example, the controller module 2070 and/or the pressure sensing module 2050. For example, the measurement storage module 2060 can be a 16 kB static random-access memory (SRAM), though other types of memory and/or capacities can also be used. In some embodiments, the controller module 2070 performs data compression on the pressure measurements before storing them in the measurement storage module 2060. By performing data compression, the measurement storage module 2060 can hold more measurements. This can allow for more frequent measurements and/or less frequent data downloading events. In some embodiments it may be advantageous to use a relatively simple compression technique so as to preserve computational resources. One example data compression algorithm could be to store the difference between sequential measurements rather than the measurements themselves. This technique could allow for fewer bits per measurement to be used by the measurement storage module 2060.

As shown in FIG. 20, the intraocular pressure sensor 2000 can also include a controller module 2070. The controller module 2070 can perform any of the functions described with respect to, for example, other controller modules disclosed herein. For example, in some embodiments, the controller module 2070 can be programmed to cause the pressure sensing module 2050 to perform measurements at predetermined times and/or regular intervals determined by, for example, the MSTR clock 2071. For example, in some embodiments the controller module 2070 is programmed to obtain a measurement every hour. Each recorded/reported measurement can, however, be calculated from multiple measurements by the pressure sensing module 2050. For example, the controller module 2070 can be programmed to obtain multiple measurements (e.g., three measurements) at relatively short intervals (e.g., 30 seconds). These can then be averaged and recorded/reported as a single measurement at the measurement storage module 2060. This process can then be repeated at longer intervals (e.g., hourly).

The intraocular pressure sensor 2000 illustrated in FIG. 20 includes a battery module 2040 to power components such as the controller module 2070 and the transmitter module/antenna 2085. In some embodiments, the physical dimensions of the battery are approximately 0.3 mm×4.5 mm, or smaller. The battery can have a power rating of approximately 0.8 µAh, or greater. Such a power rating is estimated to provide sufficient power for at least approximately 180 days between recharges. In some embodiments, the sleep power consumption of the intraocular pressure sensor 2000 is on the order of picowatts while the active power consumption is on the order of nanowatts. It should be understood, however, that the size and power rating of the battery module 2040 could be different than the figures listed above, as could the power consumption of the intraocular pressure sensor 2000. The foregoing specifications are merely examples. For instance, in some embodiments, the battery module 2040 is capable of powering the intraocular pressure sensor 2000 for at least approximately 90 days.

In some embodiments, the battery module 2040 is rechargeable by an external device, as discussed further herein. For example, the battery module 2040 can be recharged wirelessly via inductive coupling or RF energy from an external device. The battery module 2040 can also be charged by solar power or by an infrared laser (in which case, the intraocular pressure sensor 2000 can include an appropriate photovoltaic cell to convert the solar or infrared laser light to electrical power).

The intraocular pressure sensor 2000 can also include a transmitter/antenna 2085. The transmitter/antenna 2085 can be used to wirelessly transmit pressure measurements stored in the measurement storage module 2060 to an external reader device. The external reader device can be integrated into a pair of eyeglasses that are worn by the patient to download pressure measurements from the sensor 2000. The transmitter/antenna 2085 can also serve a dual purpose of receiving power wirelessly in order to charge the battery module 2040 (e.g., while the stored measurements are being downloaded). For example, the transmitter/antenna 2085 can receive power wirelessly by inductive coupling. A wireless charging device can be integrated in the same eyeglasses that include the external reader device for downloading data from the intraocular pressure sensor 2000. The transmitter/antenna 2085 can transmit measurement data and receive power for recharging the battery module 2040 either simultaneously, or one at a time (in either order).

In some embodiments, the antenna 2085 is made of a conductor such as silver, gold, platinum, tungsten, and/or alloys of the same and the like. In some embodiments, the antenna 2085 is made of an alloy of about 92% platinum and about 8% tungsten. As discussed further herein, the antenna 2085 can have a spiral shape with a diameter that is somewhat smaller than the inner diameter of the main housing 2102 so as to allow the antenna to both fit within the housing and encompass other components provided therein.

Figure 21:
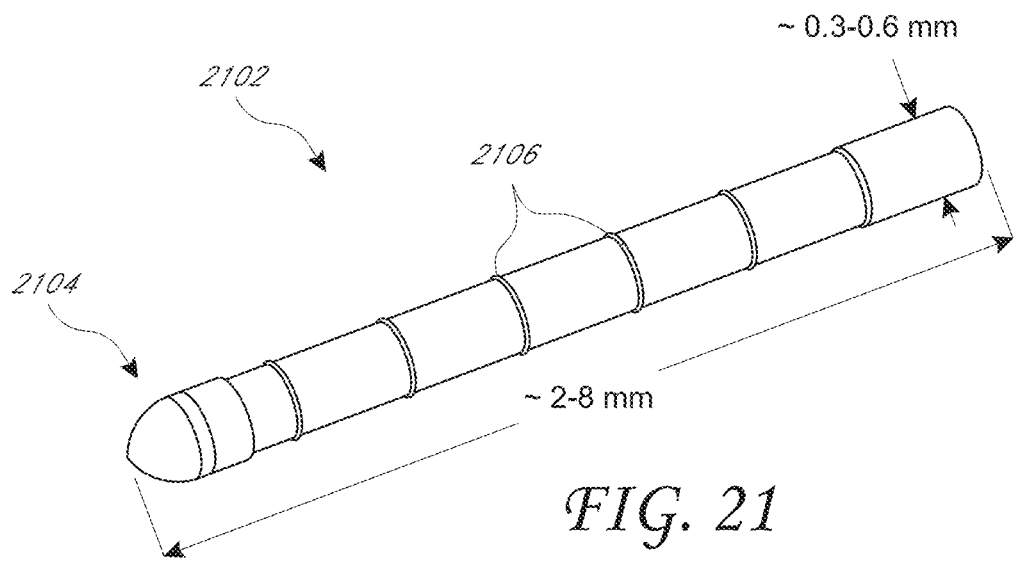
FIG. 21 is a perspective view of an example embodiment of the main housing portion of the housing assembly for the intraocular pressure sensor.

FIG. 21 is a perspective view of an example embodiment of the main housing 2102 portion of the housing assembly 2100 for the intraocular pressure sensor 2000. In some embodiments, the main housing 2102 is a generally cylindrical tube. The main housing 2102 can be made of, for example, ceramic. Ceramic offers the benefit of providing a moisture barrier that is more effective than plastic but without shielding signals to/from the transmitter/antenna 2085 like metal would. The ceramic can be, for example, at least about 90% alumina. One possible ceramic material is ~99.99% alumina, while another possible ceramic material is ~90% alumina and ~10% zirconia. In other embodiments, the main housing 2102 can be made of a high barrier plastic, such as HDPE or the like. In such embodiments, the plastic could be coated with ceramic in order to improve the moisture barrier characteristics. Such embodiments would be useful for making more complex main housing shapes (e.g., main housing shapes that include a bend or curvature). In addition, in some embodiments, components inside of the main housing 2102 (e.g., electronic components) can be coated with a hydrophobic material to further reduce the chance of damage if liquid were to infiltrate the main housing 2102. Components inside of the main housing 2102, including the integrated circuit 2075, the antenna 2085, etc., can also (or alternatively) be coated with electrically insulative coatings (e.g., a Parylene coating) in order to help prevent electrical short circuits.

The main housing 2102 can be designed to mate with a separate tip cap 2104 and/or a separate sensor cap 2108 (illustrated in FIGS. 27-29), both of which can, in some embodiments, be removable. The tip cap 2104 can have a generally rounded end, as illustrated in FIG. 21. The rounded end can ease insertion of the sensor 2000 within certain intraocular anatomical structures, such as, for example, the supraciliary/suprachoroidal space. The tip cap 2104 can be designed to press into one end of the main housing 2102. The fit between the tip cap 2104 and the main housing 2102 can be liquid-tight. For example, the tip cap 2104 can include one or more seals (e.g., O-rings, a solder ring, a eutectic ring, a compression bond, such as a gold-gold compression bond, etc.) to prevent liquid from entering the main housing 2102 at the interior junction between the tip cap 2104 and the main housing. The sensor cap 2108 can be designed to press into the other end of the main housing 2102 opposite from the tip cap 2108. It, too, can be designed to form a moisture barrier seal with the main housing 2102 using, for example, one or more seals (e.g., O-rings, a solder ring, a eutectic ring, a compression bond, such as a gold-gold compression bond, etc.), as discussed herein. The press in fit of the tip cap 2104 and the sensor cap 2108, with certain types of moisture barrier seals (e.g., O-rings), can be advantageous because the housing assembly 2100 (including the main housing 2102, the tip cap 2104, and the sensor cap 2108) can be assembled and sealed without necessarily requiring bonding, heat curing, vacuum deposition/other coatings, electrical impulse, etc.

The main housing 2102 can also include one or more anchoring members, such as a barbs 2106, for anchoring the sensor 2000 within, or at, a desired intraocular anatomical structure. In some embodiments, the anchoring members are raised ridges or barbs 2016 that rise from the outer surface of the main housing 2102 and encircle all, or a portion of, the circumference of the main housing at each anchoring location.

The main housing 2102 can be sized and shaped to fit any desired intraocular anatomy. In some embodiments, however, the intraocular pressure sensor 2000 is designed to be implanted within the supraciliary/suprachoroidal space of the eye. In such embodiments, the housing assembly 2100 may have a length of about 2-8 mm and/or a diameter of about 0.3-0.6 mm. In some embodiments, the length of the housing assembly 2100 is about 5.4 mm and the diameter is about 0.48 mm.

Figure 22:
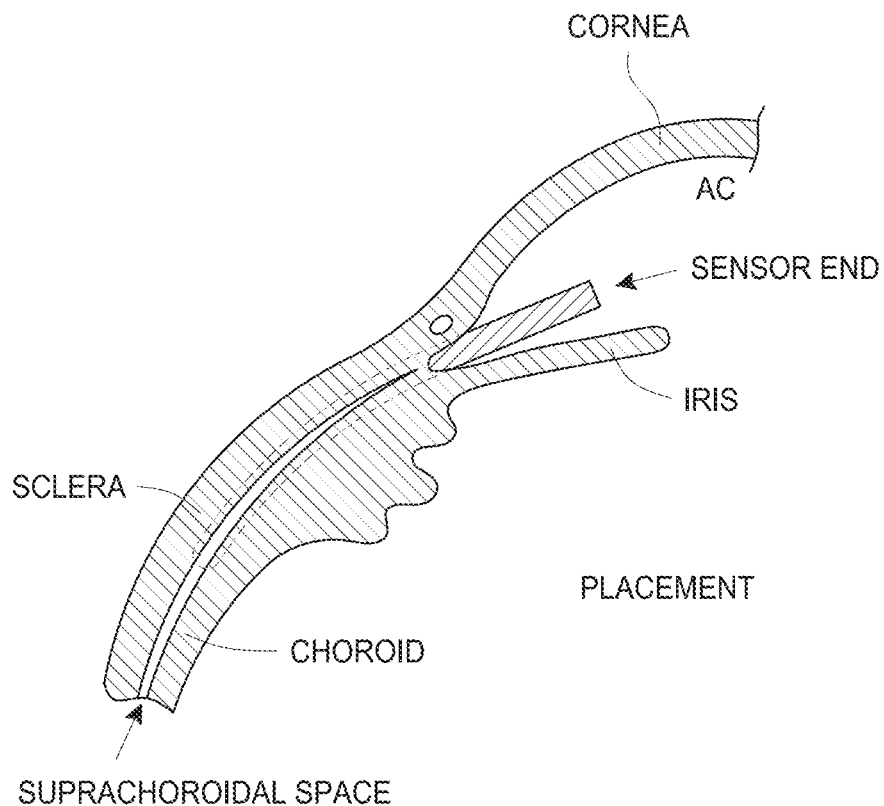
FIG. 22 illustrates the location of the intraocular pressure sensor within the supraciliary/suprachoroidal space between the ciliary body/choroid and the sclera.

FIG. 22 illustrates the location of the intraocular pressure sensor 2000 within the supraciliary/suprachoroidal space between the ciliary body/choroid and the sclera. As discussed herein, the intraocular pressure sensor 2000 can be fixed in this location by one or more anchoring members 2106. The ciliary body is contiguous with the choroid. The supraciliary/suprachoroidal space is normally a potential space at the interface between the ciliary body/choroid and sclera. The space may open to accommodate an implant such as the intraocular pressure sensor 2000. FIG. 22 illustrates an example of placement of the intraocular physiological sensor 2000 (which may be partially or completely located within the anterior chamber of the eye; or may be partially or completely located within the supraciliary/suprachoroidal space). In some embodiments, at least the sensor cap end of the intraocular pressure sensor 2000 extends into the anterior chamber so as to provide ready access to the aqueous humor in order to take pressure measurements thereof. Though not illustrated, in other embodiments, the intraocular pressure sensor 2000 can be sized and shaped to be implanted in or at other intraocular anatomical features, including but not limited to the sclera, the iris, the ciliary body, the trabecular meshwork, or Schlemm's canal.

Figure 23:
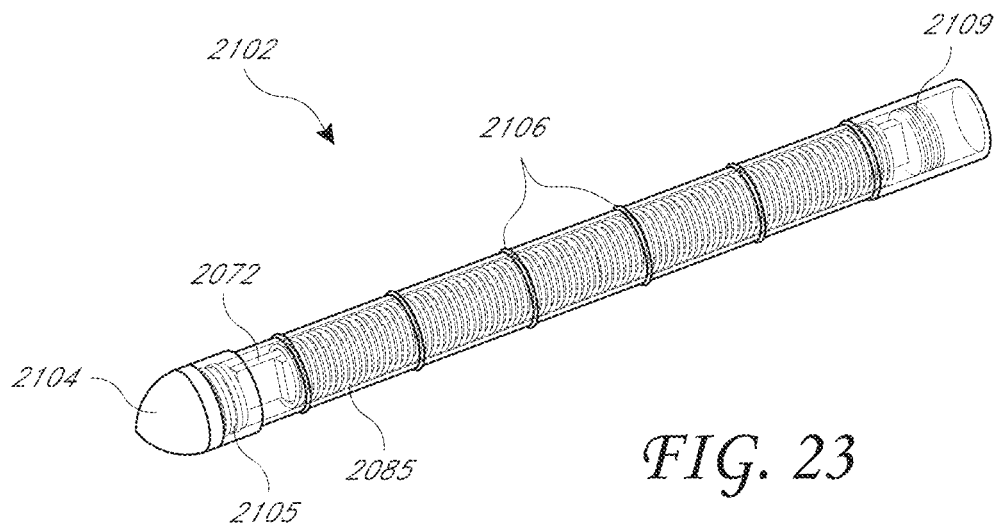

FIG. 23 is a replica of FIG. 21 in which the main housing 2102 is shown as being see-through. The tip cap 2104 and the barbs 2106 are still visible. Also visible through the see-through main housing 2102 are the antenna 2085 the O-ring seals 2105 of the tip cap 2104, and a portion of the sensor cap 2108, including its O-ring seals 2109. FIG. 23 also shows a carrier member 2072 upon which various components can be mounted. For example, the battery module 2040 and the integrated circuit 2075 can be mounted upon the carrier member 2072. The carrier member 2072 can include electrical contacts, connections, signal traces, etc. formed on its surface, or embedded within its volume in order to provide electrical connections between various components mounted on, or connected to, the carrier member 2072. In some embodiments, the carrier member 2072 is a glass backbone (e.g., borosilicate glass).

As discussed further herein, the carrier member 2072 can be designed to physically mate with the tip cap 2104 and/or the sensor cap 2108 in order to provide further structural integrity to the sensor 2000 and to fix the carrier member-mounted components within the main housing 2102. In order to allow for this physical mating, the carrier member 2072, the tip cap 2104, and/or the sensor cap 2108 can each include one or more connectors, cutouts, projections, etc. that are designed to mate, attach, join, etc. with a complementary structure on the adjacent portion of the housing assembly 2100.

As illustrated in FIG. 23, in some embodiments, the antenna 2085 is a conductor that spirals around the carrier member 2072 about the interior circumference of the main housing 2102. The antenna 2085 can be connected to the carrier member 2072 by, for example, solder so as to provide an electrical connection to the integrated circuit 2075 mounted on the carrier member 2072.

Figure 24:
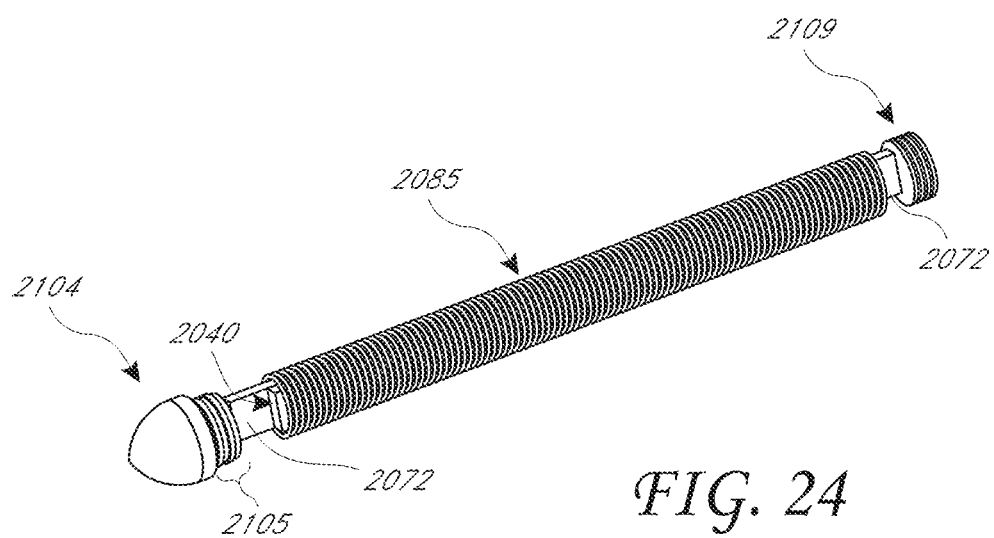
FIG. 24 is a replica of FIG. 21 but with the main housing removed.

FIG. 24 is a replica of FIG. 21 but with the main housing 2102 removed. Once again visible are the antenna 2085, the glass backbone carrier member 2072, the tip cap 2104 and its O-ring seals 2105, and a portion of the sensor cap, including its O-ring seals 2109. FIG. 24 also shows the battery module 2040 mounted on the carrier member 2072. As discussed further herein, the glass backbone carrier member 2072 is configured to physically mate with the tip cap 2104 and/or the sensor cap 2108. For example, the glass backbone carrier member 2072 is illustrated as having a generally rectangular cross-section. Each of the tip cap 2104 and the sensor cap 2108 can include a correspondingly-shaped inner cutout into which the ends of the carrier member 2072 can be inserted. As discussed further herein, the cutout and the carrier member 2072 can each include electrical contacts, or other connections, that are designed to come into contact with each other with the carrier member is mated with the sensor cap 2108.

Figure 25:
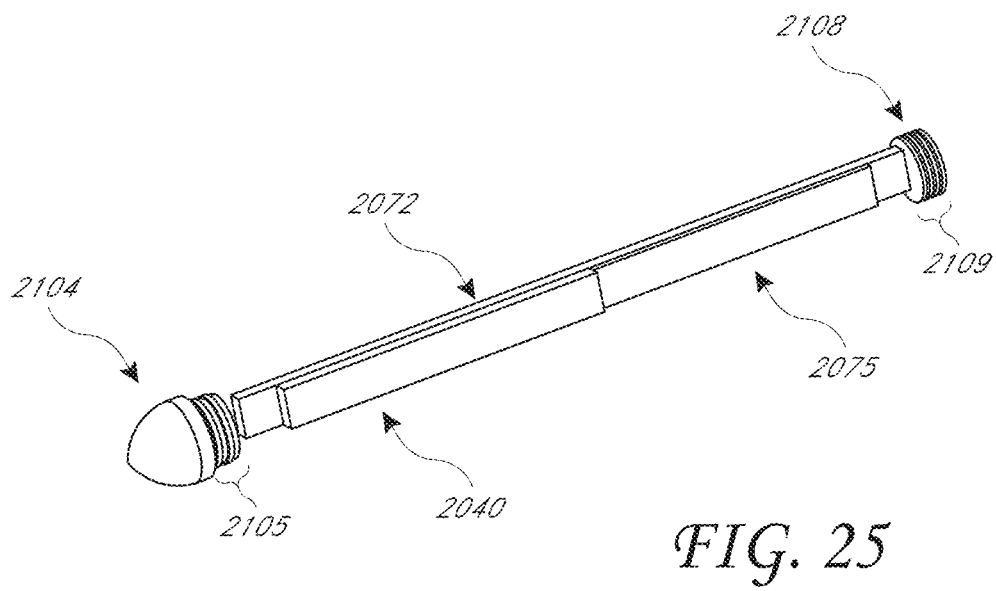
FIG. 25 is a replica of FIG. 24 but with the antenna removed.

FIG. 25 is a replica of FIG. 24 but with the antenna 2085 removed. As before, the glass backbone carrier member 2072, the tip cap 2104 and its O-ring seals, a portion of the sensor cap 2108, including its O-ring seals 2105, and the battery module 2040 are visible. With the antenna 2085 now removed, FIG. 25 also shows the integrated circuit 2075 mounted on the glass backbone carrier member 2072. As discussed herein, the integrated circuit can include, for example, the controller module 2070, the measurement storage module 2060, etc.

Figure 26:
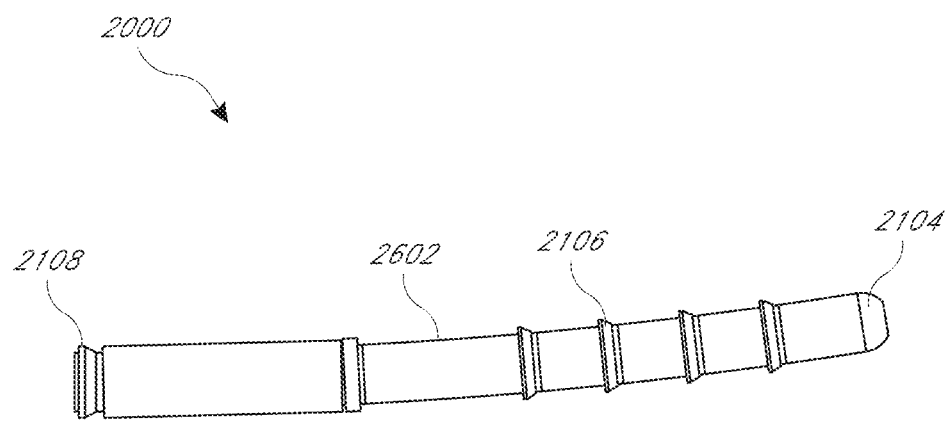
FIG. 26 illustrates another example embodiment of the intraocular pressure sensor with a curved housing.

FIG. 26 illustrates another example embodiment of the intraocular pressure sensor 2000 with a curved housing 2602. In contrast to FIGS. 21-25, which illustrate an embodiment where the intraocular pressure sensor 2000 has a generally straight main housing 2102, FIG. 26 shows a tubular main housing 2602 having a curved profile. The main housing 2602 is somewhat curved along its longitudinal dimension in order to more closely match the shape of the anatomy (e.g., the supraciliary/suprachoroidal space) where it is to be implanted. It should be understood, however, that different curvatures can also be used. Moreover, the shape and/or dimensions of the intraocular pressure sensor 2000 can be adapted to be implanted in or at other intraocular anatomical features, as well. FIG. 26 also shows the tip cap 2104, the sensor cap 2108, and anchoring barbs 2602. These features are as described elsewhere herein.

Figure 27:
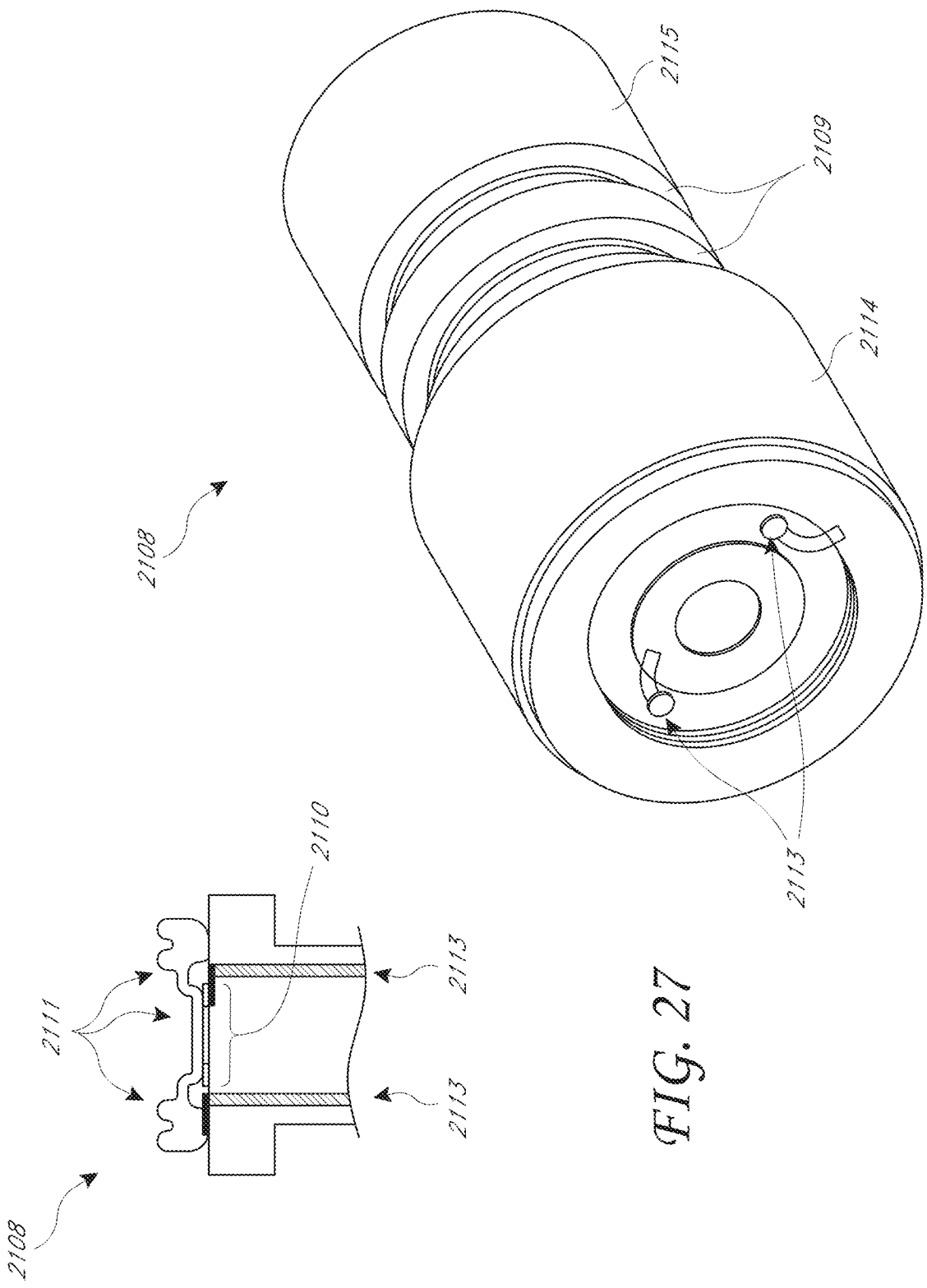
FIG. 27 illustrates a top perspective view and a cross-sectional view of a non-recessed sensor cap that is designed to be at least partially inserted into the main body of the housing.

FIG. 27 illustrates a top perspective view and a cross-sectional view of a non-recessed sensor cap 2108 that is designed to be at least partially inserted into the main body 2102 of the housing. In some embodiments, the sensor cap 2108 is made of glass (e.g., borosilicate glass), though other materials may also be possible. The non-recessed sensor cap 2108 includes a plug portion 2115 and a head portion 2114. The plug portion 2115 can be sized so as to be snugly insertable into the main body 2102 of the housing assembly 2100. For example, the diameter of the plug portion 2115 can be equal to, or just smaller, than the inner diameter of the main body 2102. The plug portion 2115 also includes one or more O-ring seals 2109. The O-ring seals include grooves that are formed into the plug portion 2115 around its circumference. The grooves are sized to fit one or more O-rings formed of an elastomeric, resilient material, such as rubber. When the plug portion 2115 is pressed into the main body 2102, the O-ring seals 2109 form a moisture barrier to prevent aqueous humor from entering the main body 2102 at the junction of the sensor cap 2108 and the main body 2102.

Although the plug portion 2115 is illustrated with O-ring seals, other types of seals can also be used at the interior junction between the sensor cap 2108 and the main body 2102. For example, a solder ring or a eutectic ring can be provided around the plug portion 2115 of the sensor cap 2108. When the plug portion 2115 is inserted into the main body 2102, the solder or eutectic ring can deform. The solder or eutectic ring can be made to reflow upon heating, thus forming a moisture barrier and/or a hermetic seal. Another type of seal that can be used in some embodiments is a compression bond. For example, the plug portion 2115 and/or the main body 2102 can be provided with a ring structure made of gold, or some other malleable material. The ring structure(s) can be located so as to be engaged when the plug portion 2115 is inserted into the main body 2102. The ring structure(s) can be deformed upon application of this insertion force, thus creating a moisture barrier and/or a hermetic seal. It may be possible to create this type of compression seal without needing to apply heat after the sensor cap 2108 is inserted into the main body 2102. It should be understood that any type of seal described herein can be used alone, or in conjunction with any other type of seal described herein. Further, other types of seals besides those described herein can also be used.

The non-recessed sensor cap 2108 also includes a head portion 2114. The head portion 2114 has a larger diameter than the plug portion 2115 and the inner diameter of the main body 2102. Thus, the head portion 2114 abuts against the end of the main body 2102 when the sensor cap is inserted. In some embodiments, the diameter of the head portion can be the same as, or similar to, the outer diameter of the main housing 2102.

A pressure sensing module 2050 is built into the head portion 2114 of the sensor cap 2108. As discussed herein, in some embodiments, the pressure sensing module 2050 is a capacitive MEMS pressure sensor. The capacitive MEMS pressure sensor includes a fixed capacitor plate 2110 and a movable diaphragm 2111. The movable diaphragm 2111 is exposed to the aqueous humor when the intraocular pressure sensor 2000 is implanted into the eye. Accordingly, the movable diaphragm 2111 deflects in response to the pressure exerted against it by the aqueous humor. As a result, the distance and/or contact between the movable diaphragm 2111 and the fixed plate 2110 of the capacitor changes in response to the pressure exerted by the aqueous humor. This results in a detectable change in capacitance. In some embodiments, the fixed capacitor plate 2110 and/or the movable diaphragm 2111 are formed of silicon, though other materials are also possible.

The capacitive MEMS pressure sensor 2050 is connected to the carrier member 2072 and/or the integrated circuit 2075 by feedthrough conductors 2113. Specifically, FIG. 27 illustrates two feedthrough conductors 2113. One of the feedthrough conductors 2113 is an electrical contact with the movable diaphragm 2111, while the other feedthrough conductor 2113 is in electrical contact with the fixed capacitor plate 2110. As illustrated in FIG. 27, the feedthrough conductors 2113 are formed longitudinally through the body of the sensor cap 2108. As will be discussed further herein, the feedthrough conductors 2113 extend from the pressure sensor 2050 to a junction between the sensor cap 2108 and the carrier member 2072. In some embodiments, the feedthrough conductors 2113 are formed of silicon, though they could also be formed of other conductive materials.

Figure 28:
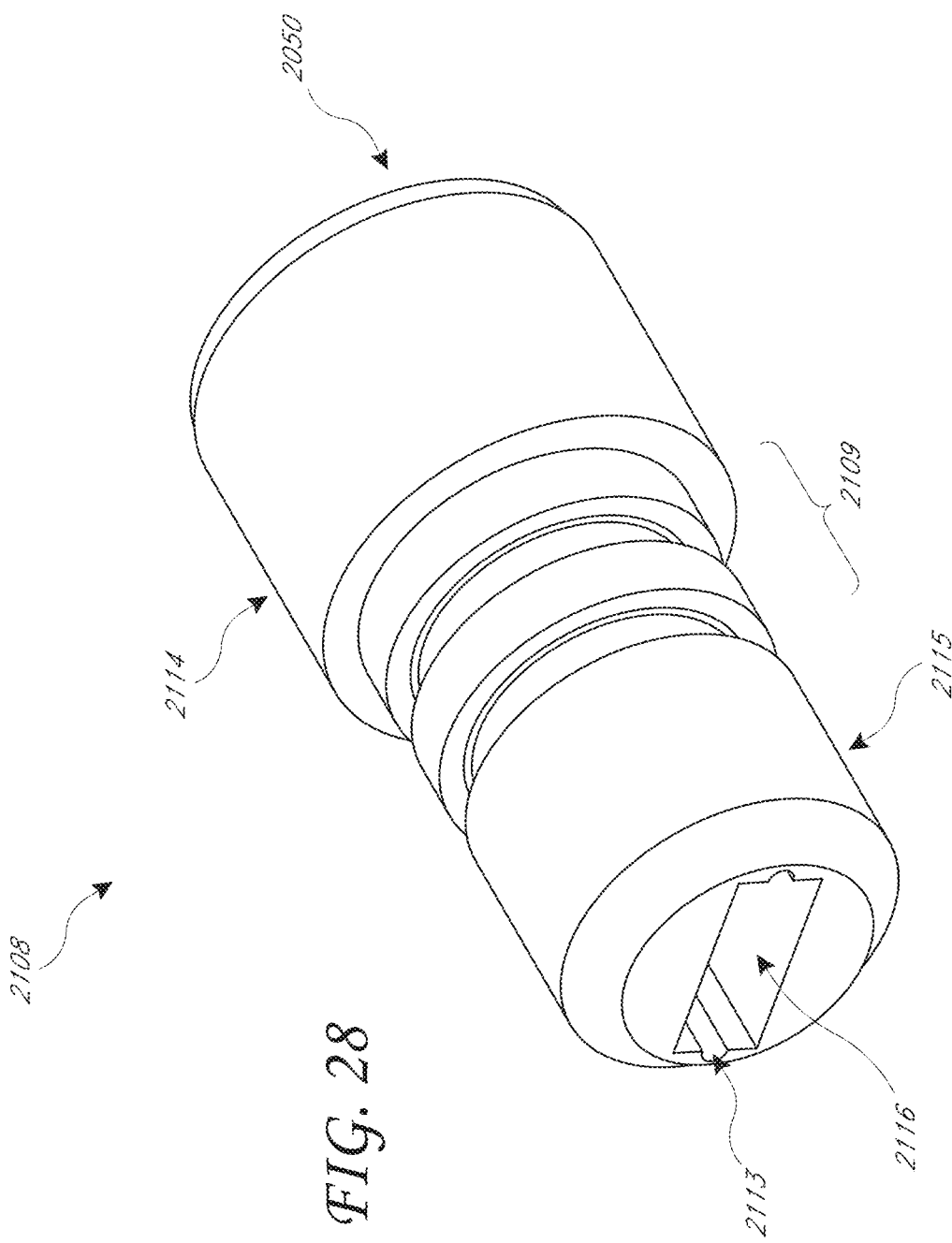
FIG. 28 illustrates a bottom perspective view of the non-recessed sensor cap.

FIG. 28 illustrates a bottom perspective view of the non-recessed sensor cap 2108. FIG. 28 shows the plug portion 2115, the head portion 2114, the pressure sensing module 2050, and the O-ring seals 2109, as discussed herein. FIG. 28 also shows the locations of the feedthrough conductors 2113 that are formed within the body of the sensor cap 2108. In addition, FIG. 28 shows a cutout 2116 that is formed in the bottom of the plug portion 2115. The cutout 2116 is shaped and sized so as to receive the carrier member 2072 when the sensor cap 2108 is inserted into the main body 2102. The carrier member 2072 can include electrical contacts that electrically connect to the feedthrough conductors 2113 when the carrier member 2072 is plugged into the cutout formed in the plug portion 2115 of the sensor cap 2108. The electrical connection between the carrier member 2072 and the sensor cap 2108 can be accomplished by mechanical contact between electrical contacts located on the respect parts and/or by soldering. In this way, electrical signals can be conducted from the flexible diaphragm 2111 and the fixed conductor plate 2110 of the pressure sensing module 2050 to the carrier member 2072 and then to the integrated circuit 2075.

Figure 29:
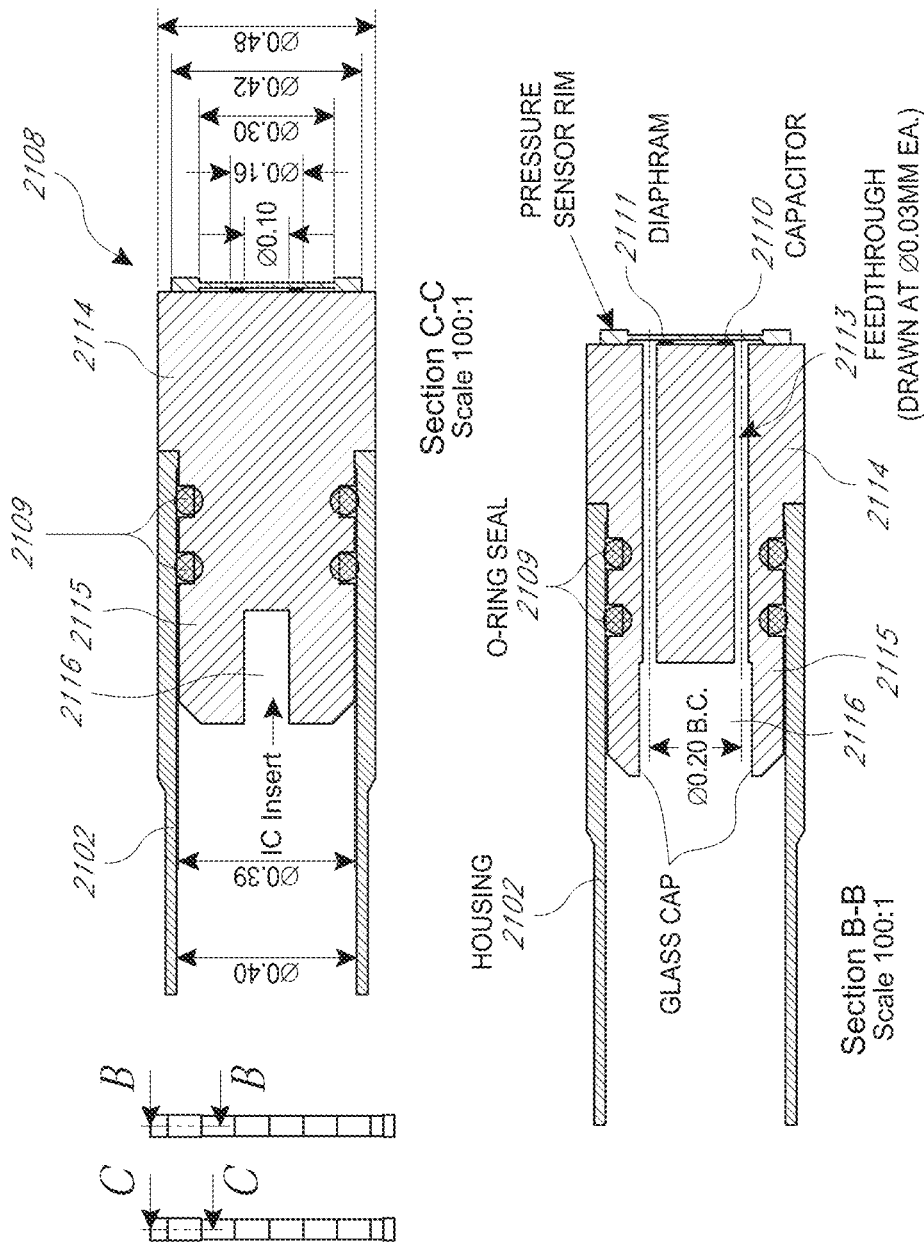
FIG. 29 illustrates two cross-sectional views of the non-recessed sensor cap, as inserted into the main housing of the intraocular pressure sensor.

FIG. 29 illustrates two cross-sectional views of the non-recessed sensor cap 2108, as inserted into the main housing 2102 of the intraocular pressure sensor 2000. The top cross-sectional view is taken along section C-C, and the bottom cross-sectional view is taken along section B-B, which is orthogonal to section C-C. The top and bottom cross-sectional views are illustrative of the plug portion 2115, the head portion 2114, the O-ring seals 2109, and the movable diaphragm 2111 and fixed capacitor plate 2110 of the pressure sensing module 2050, which are described herein. The top and bottom cross-sectional views also show the cutout 2116 which is formed in the plug portion 2115 of the sensor cap 2108. The cutout 2116 is shaped and sized to receive the carrier member 2072. The top cross-sectional view in FIG. 29 shows the thickness dimension of the cutout 2116, while the bottom cross-sectional view shows the width dimension of the cutout 2116. Each dimension of the cutout 2116 can be shaped and sized according to the corresponding dimensions of the carrier member 2072, so as to snugly receive the carrier member. Also, as illustrated in the bottom cross-sectional view, the feedthrough conductors 2113 pass through the sensor cap 2108 from the MEMS capacitor to the cutout 2116, which, in some embodiments, is the junction of the sensor cap with the carrier member 2072.

Figure 30:
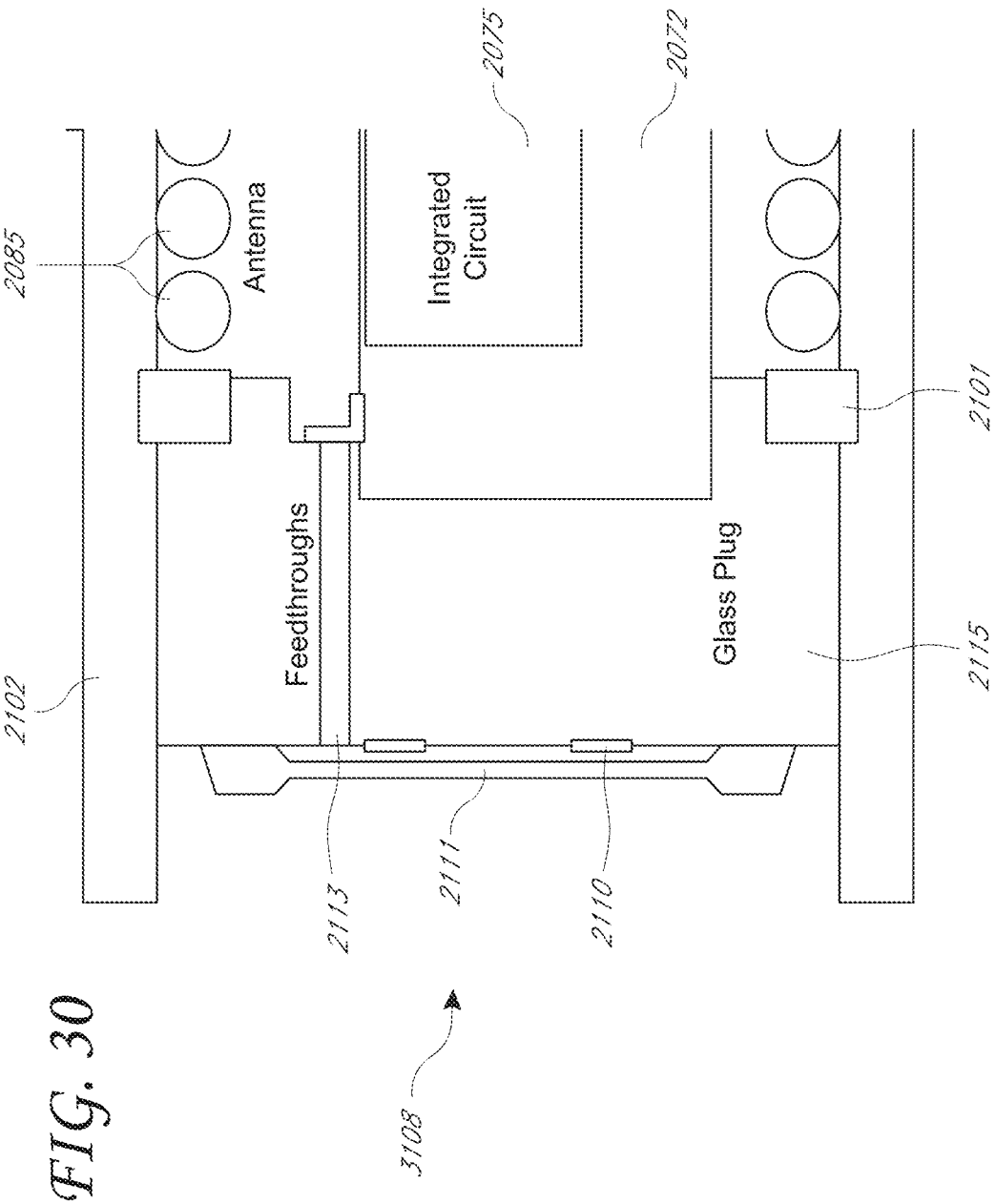
FIG. 30 illustrates a cross-sectional view of an example embodiment of a recessed sensor cap, as inserted into the main housing of the intraocular pressure sensor.

FIG. 30 illustrates a cross-sectional view of an example embodiment of a recessed sensor cap 3108, as inserted into the main housing 2102 of the intraocular pressure sensor 2000. Unlike the non-recessed sensor cap 2108 illustrated in FIGS. 27-29, the recessed sensor cap 3108 includes the plug portion 2115 but not the head portion 2114. Thus, the recessed sensor cap 3108 can be inserted entirely into the main housing 2102 of the intraocular pressure sensor 2000. The main housing 2102 can include integrated plug stops 2101 to prevent the recessed sensor cap 3108 from being inserted past the desired point within the main housing 2102.

The sensor cap 3108 also includes a cutout 2116 for mating with the carrier member 2072, as discussed herein. In the embodiment illustrated in FIG. 30 the, capacitive MEMS pressure sensor, including the fixed capacitor plate 2110 and the movable diaphragm 2111 are integrated into the top of the plug portion 2115 rather than a head portion (e.g., 2114). One or more feedthrough conductors 2113 can be formed longitudinally through the sensor cap 3108 to extend from the pressure sensor (e.g., the fixed capacitor plate 2110 and the movable diaphragm 2111) to the junction of the sensor cap 3108 with the carrier member 2072 and/or the integrated circuit 2075 in order to electrically connect the pressure sensor to the integrated circuit.

Figure 31A:
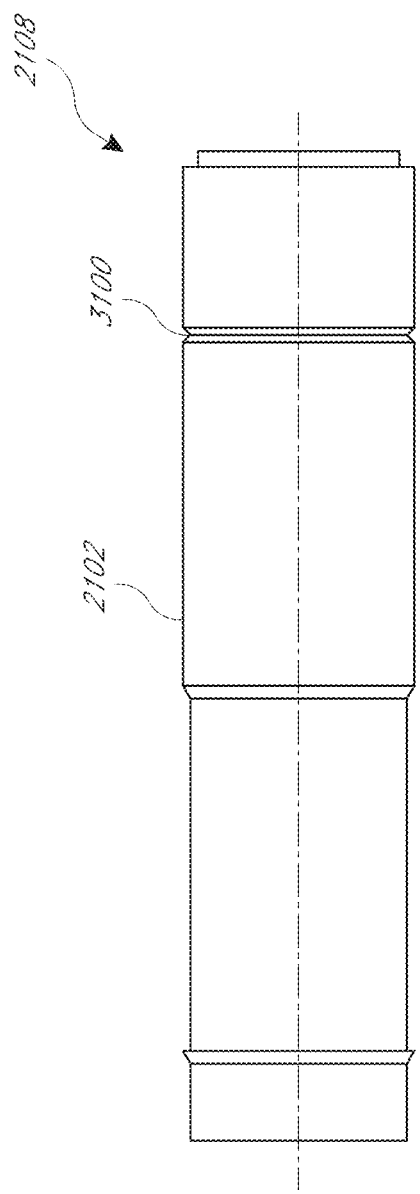
FIG. 31 illustrates an embodiment of the exterior junction between the main body of the housing and the sensor cap before (FIG. 31A) and after (FIG. 31B) forming a seal at the junction.
Figure 31B:
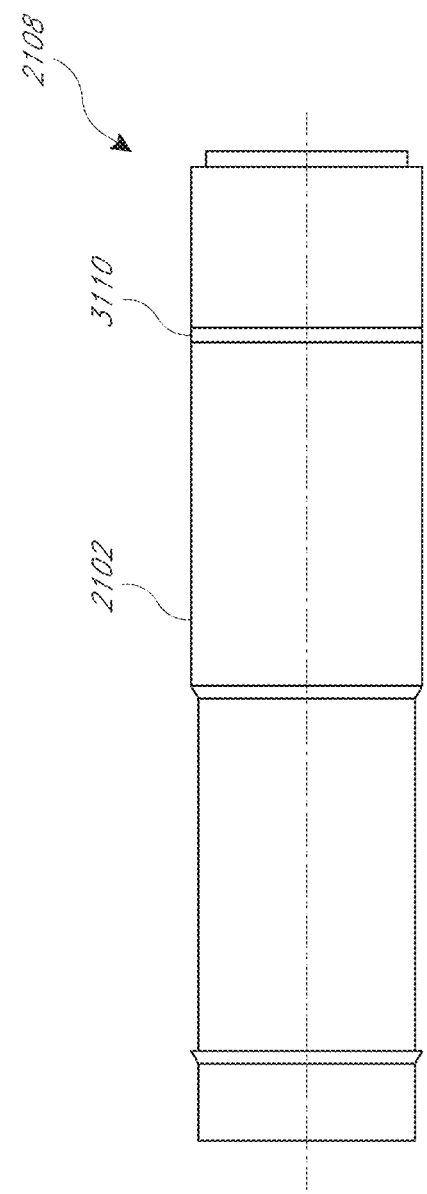

FIG. 31 illustrates an embodiment of the exterior junction 3100 between the main body 2102 of the housing and the sensor cap 2108 before (FIG. 31A) and after (FIG. 31B) forming a seal 3110 at the junction 3100. The exterior junction 3100 between the main body 2102 and the sensor cap 2108 may be an entry point for aqueous humor to enter the main body 2102 of the housing assembly. Although any such aqueous humor may still be sealed out of the main body 2102 by the internal O-rings 2109 (or another type of seal), it may be desirable in some embodiments to form a moisture barrier seal at the exterior junction 3100 in addition to, or in place of, the internal moisture barrier provided by the O-rings 2109 (or another type of seal). FIG. 31B illustrates a moisture barrier seal 3110 formed at the exterior junction 3100 between the main body 2102 and the sensor cap 2108. In some embodiments, the moisture barrier seal 3110 can be provided by sputtering gold, or some other material, on/into the junction 3100. In this way, the moisture barrier seal 3110 can help prevent aqueous humor from entering the main body 2102.

Various sensors have been described herein for taking pressure measurements within the eye. Pressure measurements taken by a sensor located in the anterior chamber 110 or otherwise in fluid communication with the aqueous humor can be, for example, absolute pressure measurements which are referenced against a vacuum. Such pressure measurements may reflect not only the gauge pressure within the eye but also the atmospheric pressure outside of the eye. As a result, variations in atmospheric pressure can cause variations in the pressure measurements taken by such intraocular sensors. Variations in the data which are due to atmospheric pressure may be undesirable in some circumstances because they are independent of the pressure variations caused by physiological processes which are typically the subject of clinical and diagnostic interest. Therefore, in some embodiments, it is advantageous to obtain pressure measurements which are not subject to variations in atmospheric pressure or which are affected by variations in atmospheric pressure to a lesser degree.

Absolute pressure measurements recorded by a sensor implanted in the eye can be processed to subtract out the effect of atmospheric pressure in order to determine the gauge pressure within the eye. This can be done, for example, by measuring not only absolute pressure within the eye using an intraocular sensor of the type described herein but by also concurrently measuring atmospheric pressure using an external sensor outside of the body. Alternatively, localized barometric weather data can be used to determine the atmospheric pressure at the time and location where the absolute pressure measurements were recorded within the eye. In either case, the atmospheric pressure measurement can be subtracted, or otherwise removed, from the measurement of absolute pressure within the eye in order to determine the gauge pressure within the eye. Unless it is specifically stated otherwise or it is evident from context, both types of measurements of the pressure in the anterior chamber of the eye (i.e., absolute pressure and gauge pressure) may be referenced herein as IOP.

It is also possible, however, to determine gauge IOP measurements without necessarily using an external pressure sensor or location-based barometric data to obtain atmospheric pressure measurements which are used to correct absolute pressure measurements made within the eye. This can be done by, for example, using an implanted sensor to record pressure measurements at, or with access to, an anatomical location where the pressure is equal to, or correlated with, atmospheric pressure. One such anatomical location is the sub-conjunctival space located between the conjunctiva and the sclera. FIGS. 32-35 describe various embodiments of implanted pressure sensors which take advantage of this fact in order to provide pressure measurements which are reflective of the gauge IOP within the eye with reduced impact from the effects of atmospheric pressure.

Figure 32:
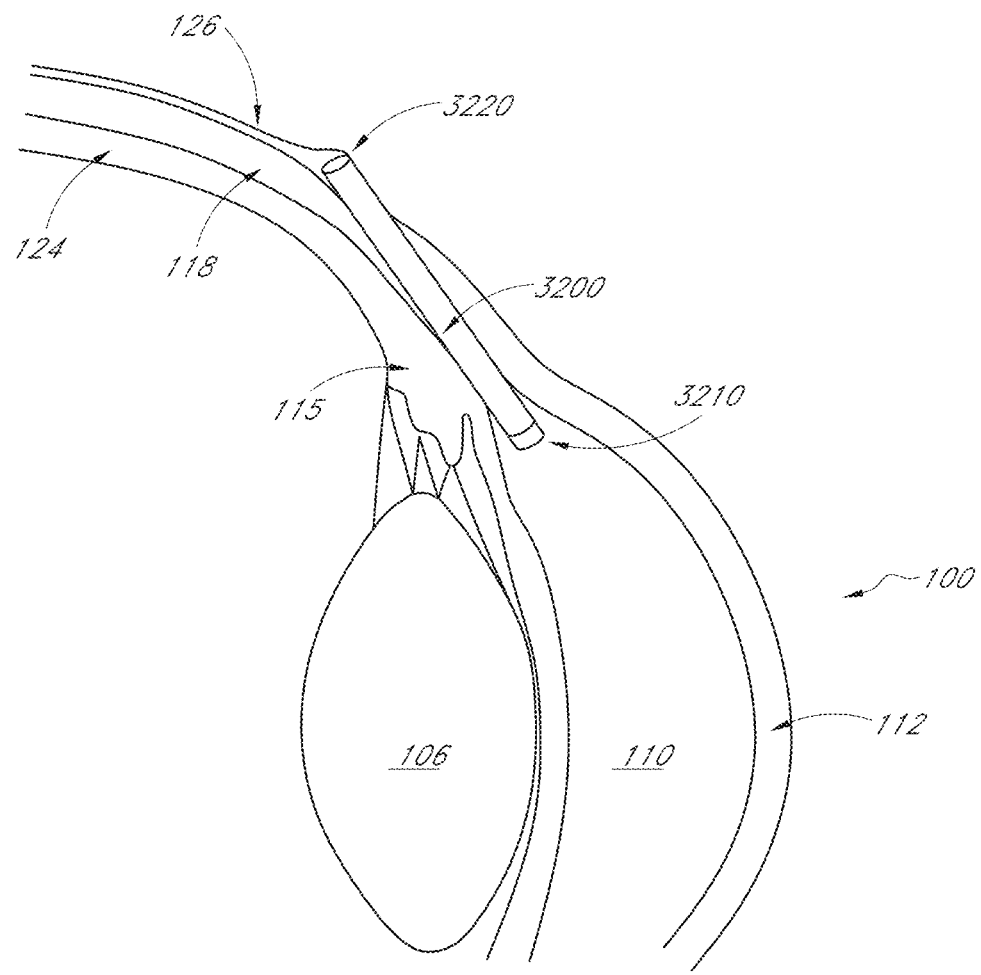
FIG. 32 is a schematic illustration of an implantable intraocular physiological sensor system located in a human eye which can be used to obtain measurements of the gauge pressure within the anterior chamber of the eye.

FIG. 32 is a schematic illustration of an implantable intraocular physiological sensor system 3200 located in a human eye 100 which can be used to obtain measurements of the gauge pressure within the anterior chamber of the eye. For reference, various anatomical features of the eye 100 are labeled in FIG. 32. For example, FIG. 32 shows the lens 106, the anterior chamber and aqueous humor 110, the cornea 112, the ciliary body 115, the sclera 118, the choroid 124, and the conjunctiva 126. As shown in FIG. 32, the intraocular physiological sensor system 3200 can be implanted partially within the anterior chamber 110, partially in the suprachoroidal space between the choroid 124 and the sclera 118, and/or partially in the sub-conjunctival space between the conjunctiva 126 and the sclera 118. It should be understood that the intraocular physiological sensor system 3200 is not necessarily drawn to scale.

In some embodiments, the intraocular physiological sensor system 3200 is an elongate tube which includes a first pressure sensor 3210 generally located at or near one end and a second pressure sensor 3220 generally located at or near the opposite end. The first and second pressure sensors can be capacitive sensors, though other types of pressure sensors may also be suitable.

As shown in FIG. 32, the physiological sensor system 3200 can be implanted within the eye such that the first pressure sensor 3210 is located in, or in fluid communication with, the anterior chamber 110. Meanwhile, the position, size, dimensions, and/or shape of the physiological sensor system 3200 can be such that the second pressure sensor 3220 at the opposite end is simultaneously located in, or in fluid communication with, the sub-conjunctival space between the conjunctiva 126 and the sclera 118. This placement can be accomplished by, for example, forming a tunnel through the sclera 118 using a sharp tool and inserting the intraocular physiological sensor system 3200 through that scleral tunnel using an ab interno approach. In some cases, access to the scleral tunnel can be achieved via the suprachoroidal space between the sclera 118 in the choroid 124. Other surgical implantation techniques, such as the ones described herein, can also be used. In some embodiments, the tunnel through the sclera 118 can be formed such that a substantially fluid-tight seal is formed between the tissue of the sclera 118 and the physiological sensor system 3200 in order to limit the exchange of fluid between the anterior chamber 110 and the sub-conjunctival space.

When the physiological sensor system 3200 is implanted, it has the capability to take concurrent measurements of the pressures within the anterior chamber and the sub-conjunctival space. Measurements taken by the first pressure sensor 3210 may be reflective of the absolute pressure within the anterior chamber 110, including the effects of atmospheric pressure outside of the eye. Meanwhile, measurements taken by the second pressure sensor 3220 may be reflective of the atmospheric pressure outside of the eye. For example, the pressure measured in, or with access to, the sub-conjunctival space may equal, or be correlated with, the atmospheric pressure outside of the eye. Concurrent pressure measurements can be taken from both the first pressure sensor 3210 and the second pressure sensor 3220. The atmospheric pressure measurement taken by the second pressure sensor 3220 can then be subtracted, or otherwise removed, from the absolute pressure measurement taken by the first pressure sensor 3210. The resulting value will be a gauge IOP value which is affected by atmospheric pressure to a lesser degree than the absolute pressure measurement taken by the first pressure sensor 3210.

In some embodiments, the gauge IOP value can be obtained according to the following equation: Gauge IOP=$P_{Sensor1}-P_{Sensor2}$, where $P_{Sensor1}$ equals a pressure measurement taken by the first pressure sensor 3210 and $P_{Sensor2}$ equals a pressure measurement taken by the second pressure sensor 3220. Alternatively, the gauge IOP value can be obtained according to the following equation: Gauge IOP=$P_{Sensor1}-f(P_{Sensor2})$, where $f(P_{Sensor2})$ is a function designed to account for any differences which may exist between the pressure in the sub-conjunctival pressure and the atmospheric pressure. For example, the sub-conjunctival pressure may be slightly less than the atmospheric pressure due to the osmotic pressure of interstitial fluid. Therefore, $f(P_{Sensor2})$ may include a negative offset to account for this difference. Other forms for the function $f(P_{Sensor2})$ can also be used.

Figure 33:
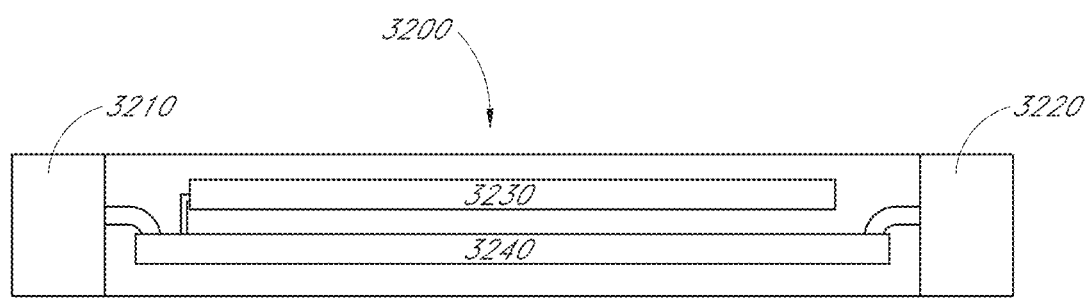
FIG. 33 is a schematic illustration of the physiological sensor system shown in FIG. 32.

FIG. 33 is a schematic illustration of the physiological sensor system 3200 shown in FIG. 32. As shown, the physiological sensor system 3200 can be an elongate tube with the first pressure sensor 3210 and the second pressure sensor 3220 located at opposite ends. The tube can be at least partially hollow inside so as to house a battery 3230 or other power source, as described herein with respect to other sensor embodiments. In addition, the tube can include circuitry 3240, such as a processor, a memory for storing pressure measurements, a transmitter/receiver, an antenna, etc., as disclosed herein. Any of the features of other sensor embodiments described herein can also be applied to the physiological sensor system 3200.

The pressure measurements taken by the first pressure sensor 3210 and the second pressure sensor 3220 can be stored locally in a memory in the device. The pressure measurements can be taken concurrently by the first pressure sensor 3210 and the second pressure sensor 3220. In some embodiments, the concurrent measurements are substantially simultaneous. Measurements can be taken by both pressure sensors at regular intervals. In some embodiments, measurements are taken by both sensors on a substantially continual basis. As already discussed, the measurement data taken by the first pressure sensor 3210 and the second pressure sensor 3220 can be processed to determine the gauge pressure within the eye. This processing can be performed on board the physiological sensor system 3200. Alternatively, the processing can be performed externally after the raw measurement data has been downloaded by an external reader device.

Although FIGS. 32 and 33 illustrate one example embodiment of an implanted sensor whose shape and positioning allows for concurrent anterior chamber and sub-conjunctival space pressure measurements to be taken, other shapes, positions, and/or configurations may also be possible. For example, in some embodiments, the first pressure sensor 3210 and the second pressure sensor 3220 may be provided in separate sensor housings. Each such sensor housing could include its own power source, memory for storing pressure measurements, and/or other electronic components described herein. In addition, each sensor housing could include suitable electronics (e.g., transmitter, antenna, etc.) to wirelessly communicate with each other and/or an external reader device. In some embodiments, the separate sensor housings could be tethered. For example, the sensor housing for the second sensor 3220 could include a tether to the sensor housing for the first sensor 3210. This tether could be used, for example, to communicate pressure measurements between the sensor housings. One of the tethered sensors may be positioned in the anterior chamber, while the other may be positioned under the conjunctiva.

While FIGS. 32 and 33 illustrate an embodiment of a physiological sensor system 3200 which can be used to determine gauge pressure within the anterior chamber of the eye based on mathematical processing of measurement data from two different sensors, it is also possible to obtain a direct measurement of the differential pressure between the anterior chamber and the sub-conjunctival space. A direct measurement of this differential pressure is also an indicator of the gauge pressure within the eye.

Figures 34A, 34B:
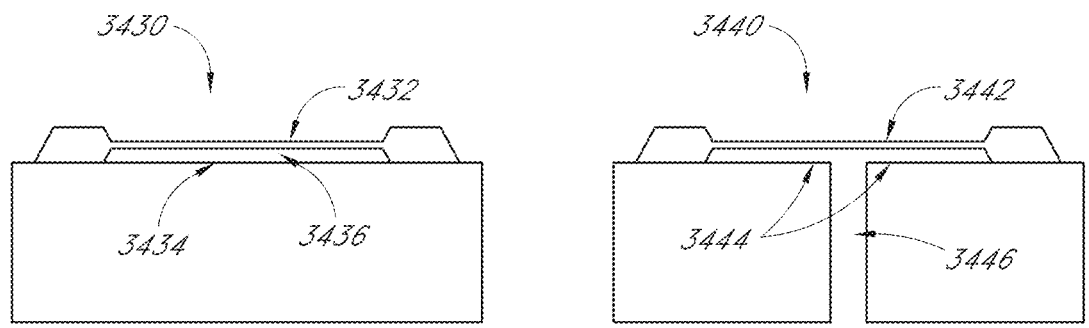

FIG. 34A illustrates an example embodiment of a capacitive absolute pressure sensor 3430, while FIG. 34B illustrates an example embodiment of a capacitive differential pressure sensor 3440. The absolute pressure sensor 3430 includes a flexible top electrode 3432 and a bottom electrode 3434. The two electrodes are separated by a sealed vacuum cavity 3436. When the absolute pressure sensor 3430 is exposed to a pressure-transmitting medium, such as a liquid, the flexible top electrode 3432 is deflected by an amount that is dependent upon the pressure of the medium. This deflection of the top electrode 3432 in turn alters the capacitance between the two electrodes. This capacitance can be measured in order to determine the pressure of the medium.

In contrast, the differential pressure sensor 3440 measures the difference in pressures between two pressure-transmitting media. The differential pressure sensor 3440 also includes a flexible top electrode 3442 and a bottom electrode 3444. The flexible top electrode 3442 can be exposed to a first pressure-transmitting medium located on its side which is opposite the bottom electrode. But the other side of the flexible top electrode 3442 can be exposed to a second pressure-transmitting medium. As shown in FIG. 34B, this can be accomplished via a channel 3446 that leads from a cavity between the top electrode 3442 and the bottom electrode 3444 to the second pressure-transmitting medium. The embodiment illustrated in FIG. 34B is just one example of a differential pressure sensor. Other designs are also possible. In some embodiments, a differential pressure sensor 3442 can be implanted in the eye such that the first pressure-transmitting medium in contact with the sensor is the aqueous humor from the anterior chamber, while the second pressure-transmitting medium is liquid in the sub-conjunctival space.

FIG. 35A illustrates a first embodiment of a differential sensor 3540 which can obtain measurements indicative of the gauge pressure within the anterior chamber of the eye. The differential sensor 3540 can have an elongate tubular body. In the illustrated embodiment, two spaced-apart electrodes 3542, 3544 are provided at the right end of the differential sensor 3540, while a channel 3560 extends from the space between the electrodes, through the tubular body, to the left end of the differential sensor 3540. As discussed above with respect to FIG. 34B, one of the electrodes 3542 is flexible.

The differential pressure sensor 3540 can be positioned as illustrated in FIG. 32 such that one end of the device is in, or in fluid communication with, the anterior chamber of the eye, while the other end of the device is in, or in fluid communication with, the sub-conjunctival space. As shown in FIG. 35A, in this instance, the flexible electrode 3542 is located in the anterior chamber, while the opposite end of the device is located in the sub-conjunctival space. With this positioning inside the eye, the aqueous humor transmits the pressure in the anterior chamber to the right side of the flexible electrode 3542. Meanwhile, the channel 3560 allows pressure from the sub-conjunctival space to be transmitted to the left side of the flexible electrode 3542. Thus, the capacitance sensed between the two electrodes 3542, 3544 is representative of the differential pressure between the anterior chamber and the sub-conjunctival space. Since the pressure in the sub-conjunctival space is equal to, or correlated with, atmospheric pressure, the differential pressure sensor 3540 measures the pressure inside the anterior chamber with respect to atmospheric pressure. This measurement represents the gauge pressure within the anterior chamber.

Although not illustrated, the channel 3560 can be open to the sub-conjunctival space or it can be primed with a non-compressible fluid and sealed with a flexible membrane such that pressure from the sub-conjunctival space can be transmitted through the flexible membrane to the non-compressible fluid in the channel 3560 and ultimately to the flexible electrode 3542 via the non-compressible fluid. In addition, in some embodiments, the differential sensor 3540 can be positioned in the eye in the direction opposite of what is illustrated, such that the electrodes 3542, 3544 are directly exposed to the sub-conjunctival space while the channel 3560 provides access to the anterior chamber.

FIG. 35B illustrates a second embodiment of a differential sensor 3540 which can obtain measurements indicative of the gauge pressure within the anterior chamber of the eye. This second embodiment is similar to the first embodiment shown in FIG. 35A except that the electrodes 3542, 3544 are provided in the middle portion of the elongate differential pressure sensor rather than at one end. Consequently, channels 3560 are formed through the elongate body on both sides of the flexible electrode 3542 so as to provide access from the pressure-transmitting media in the anterior chamber on one side and the sub-conjunctival space on the other side. These channels 3560 can be open or sealed with flexible membranes and primed with a non-compressible fluid in order to transmit pressure from the anterior chamber and the sub-conjunctival space to the flexible electrode 3542.

Correlation of Absolute IOP Measurements with Concurrent Atmospheric Pressure Measurements As just discussed, the IOP measurements taken by some of the implantable sensor devices described herein may be absolute IOP measurements which are affected by variations in atmospheric pressure. In such cases, the absolute IOP measurements can be corrected to reflect the gauge IOP within the eye—typically the clinically-relevant value—by compensating for the effect of atmospheric pressure on those measurements. This can be done by, for example, concurrently measuring atmospheric pressure using a local external sensor outside of the body and then subtracting the atmospheric pressure measurement from the absolute IOP measurement taken by the implanted sensor. In practice, this may be difficult to accomplish because the atmospheric pressure experienced by an individual can vary significantly over relatively short periods of time; therefore inadequate synchronization between the timing of the atmospheric pressure measurement and the absolute IOP measurement inside the eye may cause inaccuracies in the calculated gauge IOP value.

Figure 36A:
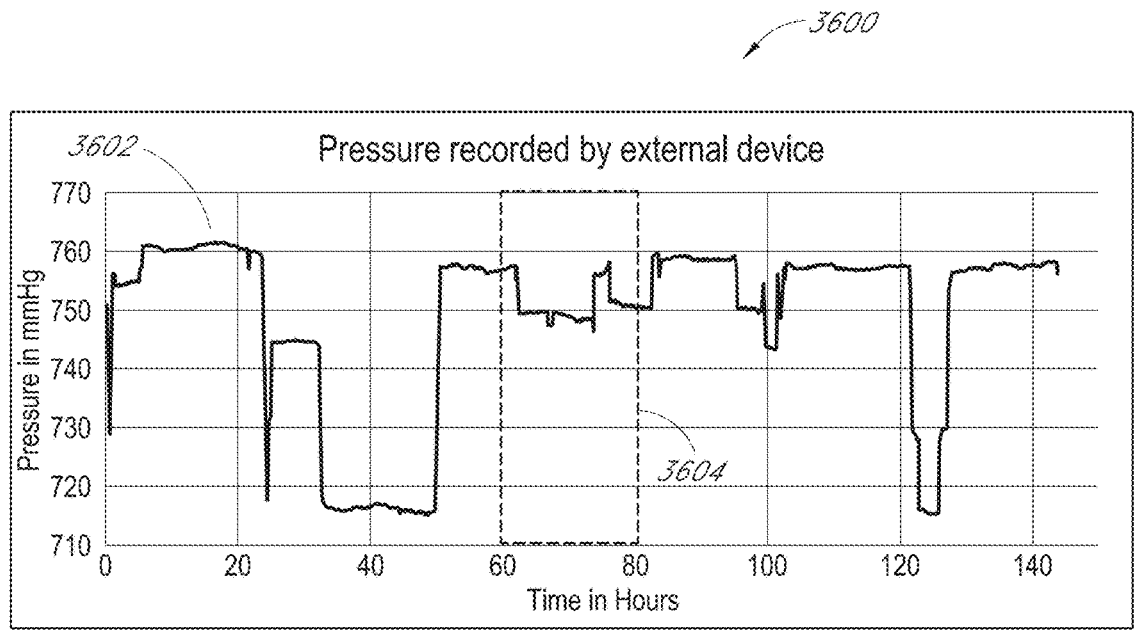
FIG. 36A is a graph of the atmospheric pressure measured by a barometer worn by a user.
Figure 36B:
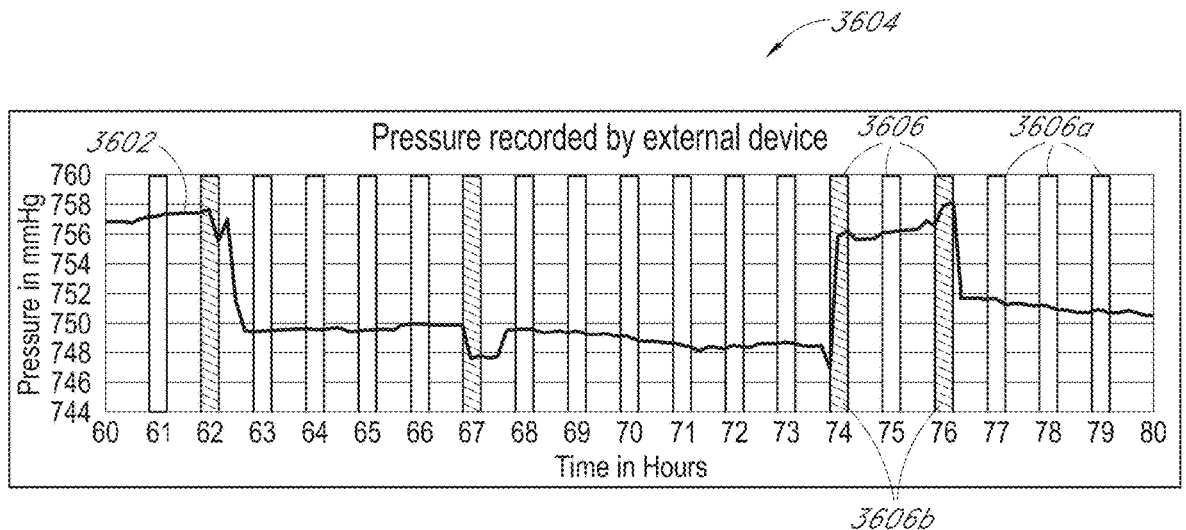
FIG. 36B shows a zoomed-in portion of the signal shown in FIG. 36A during the period of time from hour 60 until hour 80.

FIG. 36A is a graph 3600 of the atmospheric pressure measured by a barometer worn by a user. A signal 3602 shows the variation in atmospheric pressure over a period of about 140 hours. FIG. 36B shows a zoomed-in portion 3604 of the signal 3602 during the period of time from hour 60 until hour 80. During this period of time, the signal 3602 shows that the atmospheric pressure usually varied relatively slowly over time, most likely due to normal changes in weather conditions. An example of this kind of relatively slow weather-induced variation over time is shown by the signal 3602 from hour 69 until hour 73. However, the signal 3602 also shows that there were sudden, relatively large magnitude changes that also occurred. Examples of these types of sudden large changes in measured atmospheric pressure are seen in the signal 3602 approximately during hour 63 (i.e., between 62 and 63 on the graph), hour 68 (i.e., between 67 and 68 on the graph), hour 75 (i.e., between 74 and 75 on the graph), and hour 77 (i.e., between 76 and 77 on the graph). These sudden large changes in atmospheric pressure may have been the result of changes in altitude experienced by the user while he or she was driving up or down hills, moving between different floors of a building, etc.

Because relatively large changes in atmospheric pressure such as these can occur over relatively short periods of time, care should be taken when correlating an atmospheric pressure measurement with an absolute IOP measurement for use in calculating a gauge IOP value: if the external and internal pressure measurements are offset from one another in time by too great a degree, there is a potential that the gauge IOP value derived from the two measurements may be significantly affected by one of these sudden, large magnitude changes in atmospheric pressure, thus reducing the accuracy of the gauge IOP value.

This difficulty in correlating internal absolute IOP measurements with external atmospheric pressure measurements can be exacerbated if there is some amount of drift over time in the accuracy of the respective timekeeping devices used by the external and implanted pressure measurement devices. For example, as shown in FIG. 20, an IOP sensor implant may include a timekeeping device, such as a timer or a clock, which may be used to indicate the times at which pressure measurements are to be taken. Design constraints may favor or require the use of relatively simple timer or clock circuits. For example, cost, power consumption, and/or circuit size constraints may favor or require the use of less advanced timers and/or clocks, such as ones which do not include a piezoelectric resonator, in implantable sensor devices. These timers and/or clocks may be less accurate than more advanced versions which would require, for example, larger numbers of circuit elements, a larger amount of space within the implantable sensor device, and/or more power. As a result, the timekeeping accuracy of the timers and/or clocks which may be used in implantable devices of the sort described herein may drift over time. In addition, these timekeeping devices may be more affected by temperature variations.

Even a timekeeping drift of just 0.1%, for example, can result in relatively large inaccuracies over periods of time such as days, weeks, or months. As a result, there may be a time offset between an atmospheric pressure measurement taken by an external device and an internal absolute IOP measurement taken by an implant within the patient's eye even though the respective timekeeping elements used by the two devices may indicate that the two measurements were taken concurrently. And, of course, a significant change in either the atmospheric pressure or the absolute IOP could occur during that time offset. If so, it would result in an inaccurate calculation of the gauge IOP value.

Figure 36C:
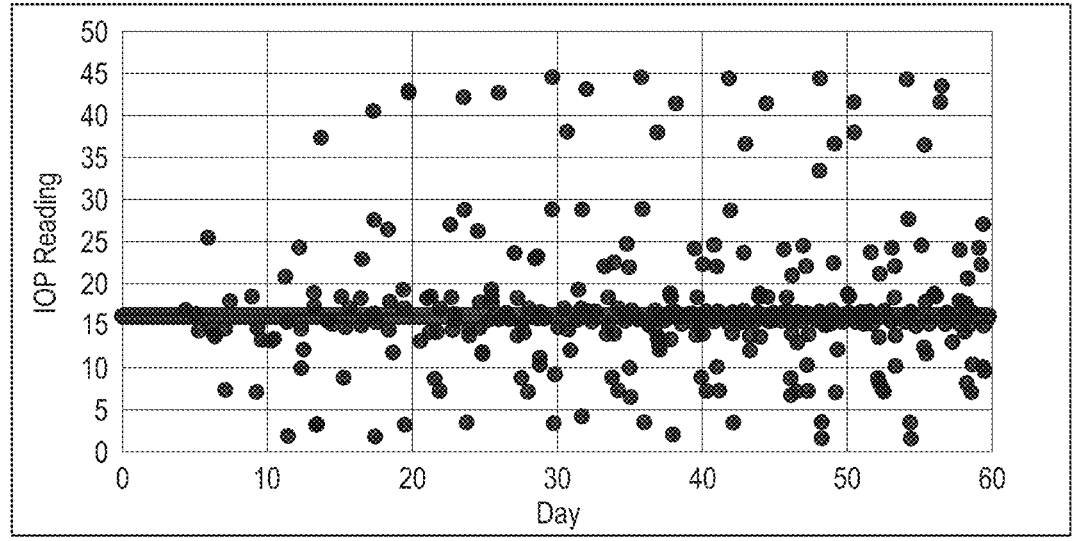
FIG. 36C illustrates the simulated effect of a timer inaccuracy of 0.1% which causes time offsets between absolute IOP measurements and atmospheric pressure measurements used to calculate gauge IOP values.
Figure 36D:
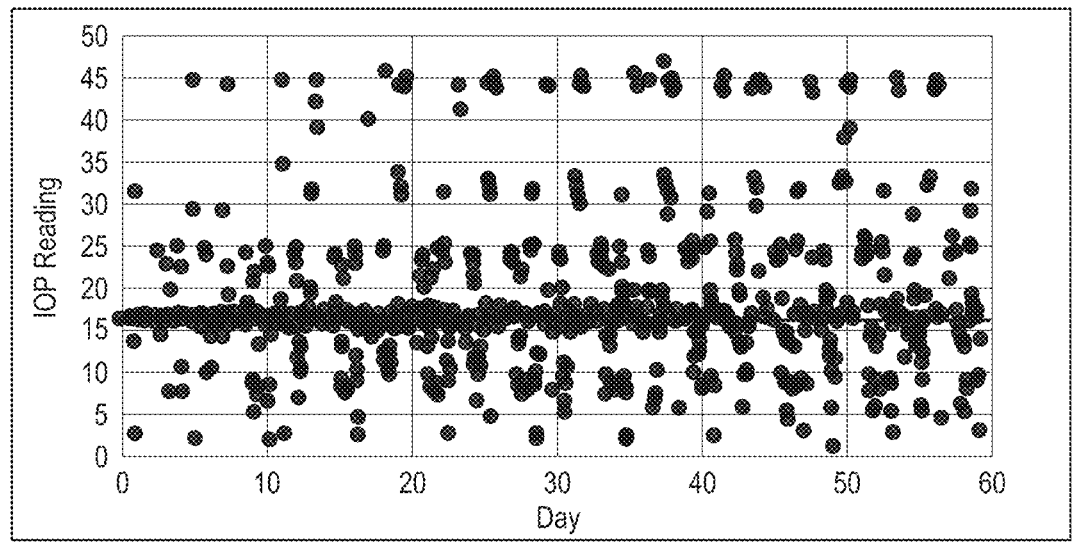
FIG. 36D illustrates the simulated effect of a timer inaccuracy of 1% which causes time offsets between absolute IOP measurements and atmospheric pressure measurements used to calculate gauge IOP values.
Figure 37A:
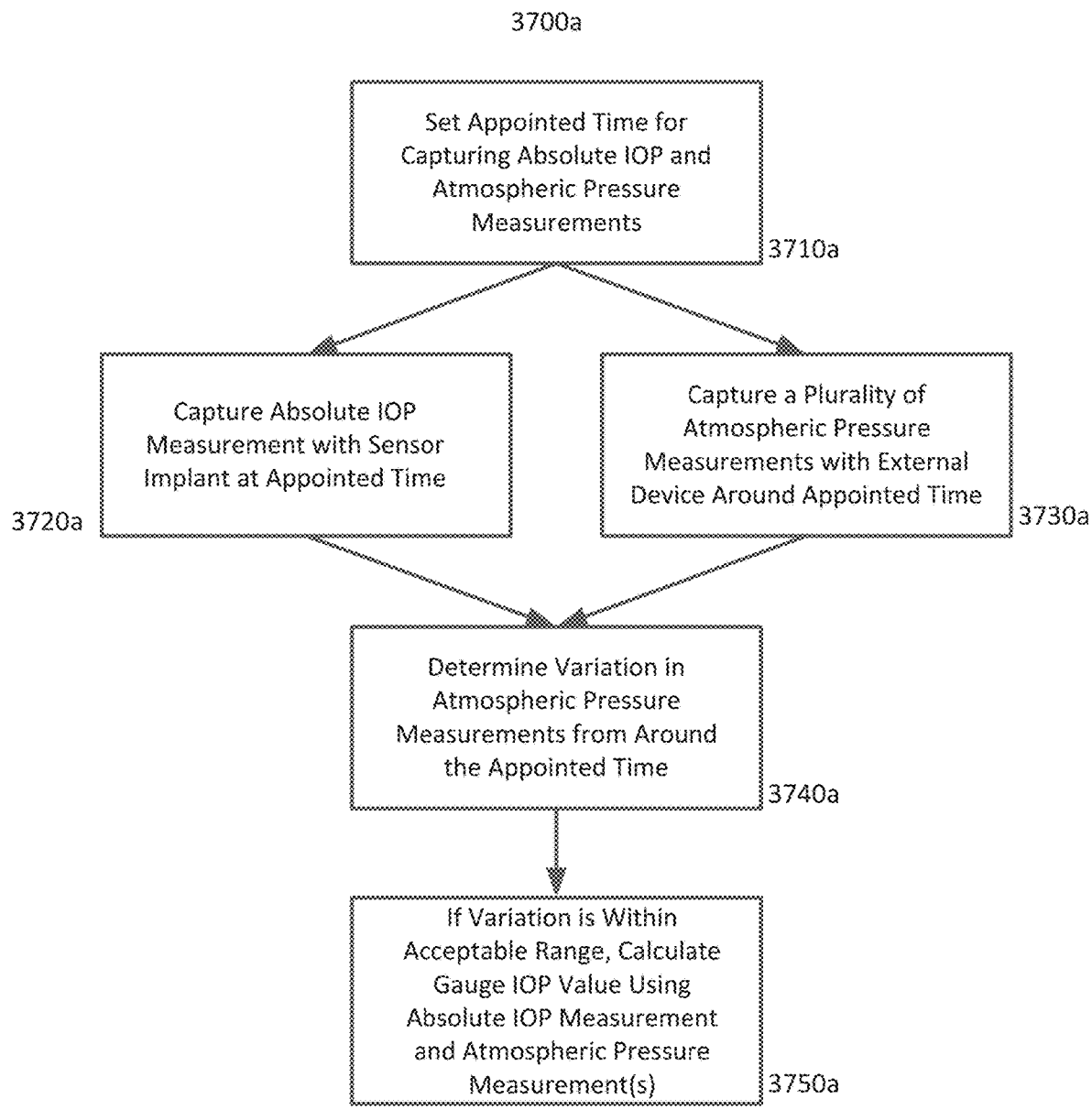
FIG. 37A illustrates an example method for calculating a gauge IOP value using one or more atmospheric pressure measurement(s) from an external device and one or more absolute IOP measurement(s) from a sensor implant within the patient's eye.
Figure 37B:
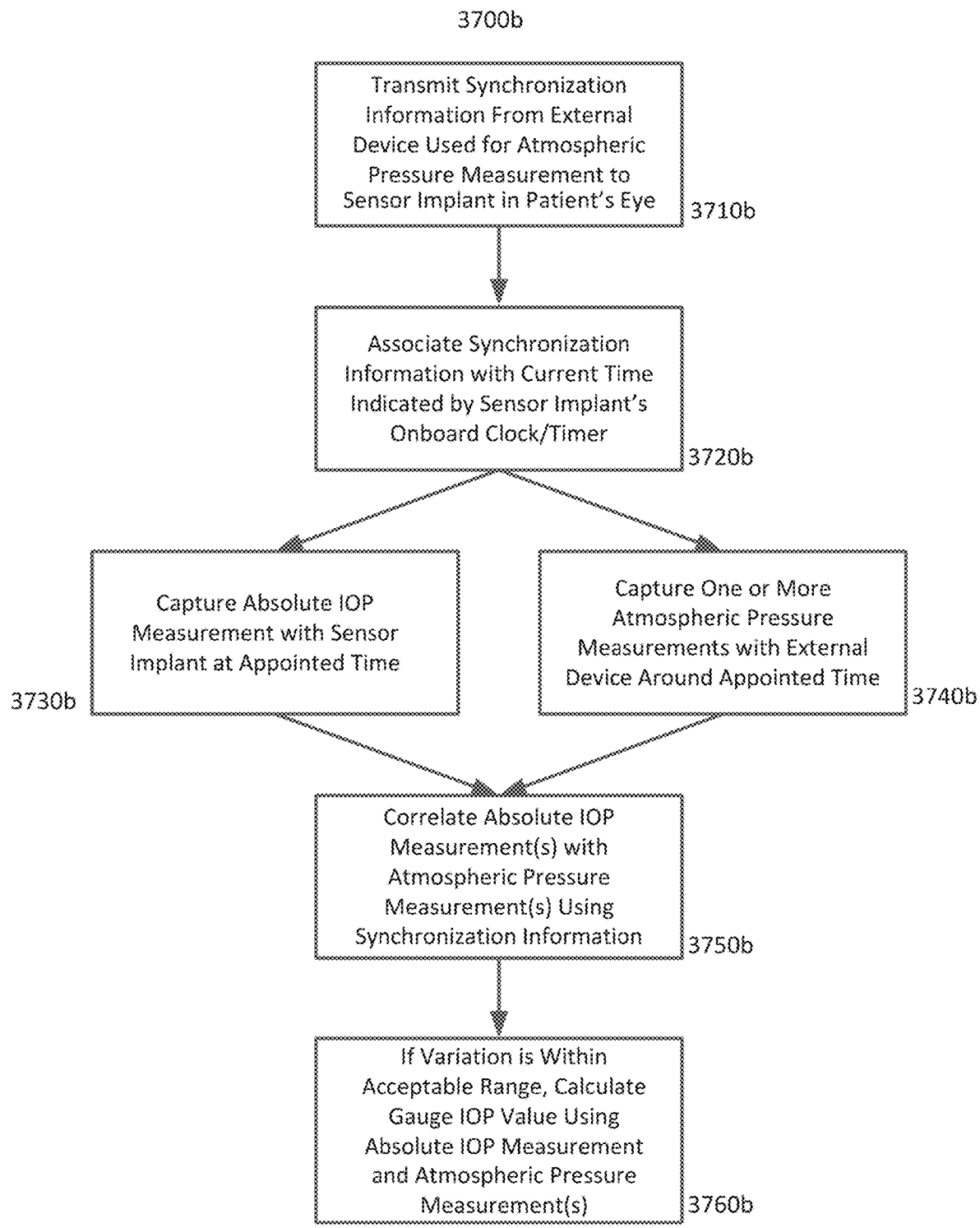
FIG. 37B illustrates an example method for correlating an atmospheric pressure measurement from an external device with an absolute IOP measurement from a sensor implant for purposes of determining a gauge IOP value.

FIGS. 36C and 36D are graphs 3610, 3620, respectively, which illustrate examples of the inaccuracies in calculated gauge IOP values which may result from time offsets between absolute IOP measurements and atmospheric pressure measurements. FIG. 36C illustrates the simulated effect of a timer inaccuracy of 0.1%, while FIG. 36D illustrates the simulated effect of a timer inaccuracy of 1%. In both graphs 3610, 3620, the plotted gauge IOP values were calculated by subtracting atmospheric pressure values from absolute IOP values at regular intervals (e.g., every hour). In these simulated examples, the absolute IOP signal and the atmospheric pressure signal were designed to result in a constant gauge IOP signal of 16 mmHg. That is, although the absolute IOP signal and the atmospheric pressure signal both varied in time similarly to what is shown in FIGS. 36A and 36B, the difference between these signals—gauge IOP—was designed to be constant. If the gauge IOP values had been calculated using absolute IOP values and atmospheric pressure values that were perfectly synchronized in time, then the plotted gauge IOP values would have remained constant at 16 mmHg. However, in these simulations, time drift was introduced between the atmospheric pressure values and the respective absolute IOP values used to calculate the gauge IOP values. As shown in the graphs 3610, 3620, within just a few days or less, the simulated timer inaccuracies resulted in a lack of synchronization between the respective absolute IOP values and atmospheric pressure values, which in turn caused large, false variations in the calculated gauge IOP values. FIGS. 37A and 37B illustrate example methods for avoiding these types of inaccuracies.

FIG. 37A illustrates an example method 3700a for calculating a gauge IOP value using one or more atmospheric pressure measurement(s) from an external device and one or more absolute IOP measurement(s) from a sensor implant within the patient's eye. The method begins at block 3710a where the appointed times and/or intervals are set for capturing absolute IOP measurements, using a sensor implant in the patient's eye, and atmospheric pressure measurements, using an external device. For example, both the external device and the implanted sensor device can be set (e.g., using onboard software, firmware, and/or hardware) so as to capture measurements at, or around, times $T_1$, $T_2$, $T_3$, . . . , etc. These times may be independently measured by the external device and the sensor implant using, for example, their respective onboard timekeeping devices.

As already discussed, even though the respective timekeeping devices used by the external device and the sensor implant may be initially synchronized, timekeeping drift may cause them to gain or lose time with respect to one another, thus losing synchronization. As a result, the sensor implant may actually capture absolute IOP measurements at times $T_1 \pm \Delta_1$, $T_2 \pm \Delta_2$, $T_3 \pm \Delta_3$, etc. Similarly, the external device may actually capture atmospheric pressure measurements at times $T_1 \pm \delta_1$, $T_2 \pm \delta_2$, $T_3 \pm \delta_3$, etc., where $\Delta_n$ and $\delta_n$ may be different and unknown. Additionally, or alternatively, both the external device and the sensor implant can be set so as to capture measurements at, or around, intervals $I_1$, $I_2$, $I_3$ . . . . But, once again, there may be unknown offsets between the instants in time when the external atmospheric pressure measurements and the absolute IOP measurements are actually captured.

At block 3720a, the sensor implant captures an absolute IOP measurement within the patient's eye at the appointed time/interval (e.g., $T_1$, $I_1$). This measurement may be stored in an onboard memory or transmitted to an external reader device, etc. At least partially concurrently, at block 3730a, the external device captures a plurality of measurements during a window of time that may extend before and/or after the appointed time/interval (e.g., $T_1$, $I_1$). The length of the atmospheric pressure measurement window can be determined based on, for example, the timekeeping drift that is present in the sensor implant timekeeping device and/or the timekeeping device used by the external device which measures atmospheric pressure. The amount of timekeeping drift can specify an uncertainty window around each appointed measurement time during which a measurement may occur. In some embodiments, the atmospheric pressure measurement window can be set to be at least as large as this timekeeping uncertainty window. For example, in some embodiments the external device captures a plurality of measurements during a 20 minute window of time centered on the appointed time/interval. These atmospheric pressure measurement windows are indicated in FIG. 36B by the bars 3606 which are centered at each hour on the hour. The number of atmospheric pressure measurements captured during each atmospheric pressure measurement window can be selected based on, for example, the length of the window of time, the desired sampling rate, the available memory, etc. During the window of time, atmospheric pressure measurements may be captured, for example, every second, every 10 seconds, every minute, etc.

At block 3740a, the measurements captured during the atmospheric pressure measurement window of time can be analyzed to determine the amount of variation that is present in the measurements. For example, the atmospheric pressure measurements can be analyzed to determine whether, during the window around the appointed measurement time/interval, the variation between the atmospheric pressure measurement values stays within a selected range (e.g., variation ≤10 mmHg, ≤5 mmHg, ≤1 mmHg, ≤10%, ≤1%, etc.) The calculation of the variation in the atmospheric pressure signal can be done according to any appropriate mathematical technique, including calculation of one or more differences, calculation of a variance or standard deviation, etc. This analysis can be performed by, for example, the external measurement device. Alternatively, the analysis can be performed by a separate processing device to which the atmospheric pressure measurements are uploaded. In FIG. 36B, the unshaded bars 3606a are examples of ones where the amount of variation in the measurements captured during an atmospheric pressure measurement window was within a selected acceptable range, while the shaded bars 3606b are examples of ones where the amount of variation was found to be outside the selected acceptable range.

At block 3750a, if the variation in the atmospheric pressure measurements captured during the window of time is acceptable, then one or more of the atmospheric pressure measurements within the window can be accepted and used, together with the absolute IOP measurement captured at the appointed time/interval using the sensor implant, to calculate a gauge IOP value. For example, the atmospheric pressure measurement which is nearest in time to the appointed time/interval may be selected for use in the calculation of the gauge IOP value. Or the average of all measurements during the atmospheric pressure measurement window may be used. Or a representative atmospheric pressure value can be computed or selected from all the measurements in the atmospheric pressure measurement window in some other way. However, in these embodiments, an atmospheric pressure measurement is only accepted for use in calculating a gauge IOP value if the atmospheric pressure data are relatively stable (within prescribed limits which can be set based on the application or the desired accuracy) over the course of the atmospheric pressure measurement window. In this way, a gauge IOP value is only calculated for times when it is relatively certain that the calculated value will not be substantially negatively impacted by variations in atmospheric pressure experienced by the user during the atmospheric pressure measurement window. Alternatively, the gauge IOP value could be calculated in all cases and then only stored and/or presented to the user if the foregoing criterion is met. Or a suspect gauge IOP value (e.g., one calculated using data captured during a period of time when variation in atmospheric pressure exceeded some set threshold) can be presented to the user with a flag or notification that it is a suspect value. The calculation of a gauge IOP value according to block 3750a can be performed by, for example, an external device to which atmospheric pressure measurements and IOP measurements are both uploaded.

FIG. 37B illustrates an example method 3700b for correlating an atmospheric pressure measurement from an external device with an absolute IOP measurement from a sensor implant for purposes of determining a gauge IOP value. The method 3700b begins at block 3710b, where an external device or system which is used to capture atmospheric pressure measurements initiates a synchronization operation by wirelessly transmitting synchronization information to the sensor implant within the patient's eye. The synchronization information can be, for example, a value, such as a timestamp or a unique correlation ID number, which is associated with a particular time (e.g., the current time when the synchronization signal is transmitted), as indicated by the timekeeping device used by the external device to determine when to capture atmospheric pressure measurements. In some embodiments, the synchronization information may be wirelessly transmitted at a different frequency than that which is used to send wireless power to the implant and/or to download data from the implant. The synchronization information can be stored by the external device in association with the time of the synchronization operation, as indicated by its onboard clock or timer. The synchronization information can be stored together with the measurements of atmospheric pressure, which may also be stored in association with the times when they were captured, as indicated by the onboard clock or timer.

In some embodiments, the synchronization information is transmitted by the external device at predetermined times and/or intervals. In some cases, the user may be prompted to interact with the external device so as to initiate a synchronization operation. In some embodiments, the external device used to capture atmospheric pressure measurements may be an article designed to be worn on the wrist like a watch. The external device may output an audible alarm or other prompt to remind the user to perform a synchronization operation. The synchronization operation may require the user to bring the external device in proximity to his or her eye so as to allow the sensor implant to more readily receive the synchronization information. In some embodiments the external device may transmit the synchronization information using a transmission power sufficiently high so that the user is not required to bring the external device in proximity to his or her eye. In such embodiments the external device may be located on the body of the patient, for example on the wrist of the user or hung from neck of the user, or even nearby the user such as in the same room, and it may not be required that the user bring the external device into close proximity to his or her eye.

At block 3720b, the sensor implant receives the synchronization information and associates it with the current time, as indicated by its onboard timekeeping device (e.g., clock or timer). The sensor implant can then store the synchronization information along with the associated time of the synchronization operation. The synchronization information can be stored together with the measurements of absolute IOP, which may also be stored in association with the times when they were captured, as indicated by the onboard timekeeping device of the sensor implant.

Then, at block 3730b the sensor implant captures an absolute IOP measurement within the patient's eye at the appointed measurement time/interval. At least partially concurrently, at block 3740b, the external device captures one or more atmospheric pressure measurements at and/or around the appointed measurement time (e.g., as discussed with respect to FIG. 37A).

After absolute IOP and atmospheric pressure measurements have been captured, they can both be uploaded, together with the synchronization information respectively stored by the two devices, to a processing device. The processing device can then, at block 3750b, correlate one or more absolute IOP measurements with one or more atmospheric pressure measurements based on the synchronization information. As already mentioned, the synchronization information received from the atmospheric pressure measurement device is associated with the time indicated by its timekeeping device when the synchronization operation was performed. Similarly, the synchronization information received from the sensor implant is associated with the time indicated by its timekeeping device when the synchronization operation was performed. Thus, the synchronization information can be used to identify one or more atmospheric pressure measurements which were taken at, or approximately at, the same time as an absolute IOP measurement from the sensor implant (e.g., within minutes or, more preferably, within seconds of each other). Then, at block 3760b, the processing device can calculate a gauge IOP value using the correlated absolute IOP measurement(s) and atmospheric pressure measurement(s). In other embodiments, the implant need not necessarily include a timekeeping device but may instead rely on receiving a wireless signal from an external device to initiate an IOP measurement. The external device could perform an atmospheric pressure measurement at or near the time when the wireless signal is transmitted (e.g., within 1 s, or within 10 s, or within 60 s).

In some embodiments, absolute IOP measurements can be correlated with respective concurrent atmospheric pressure measurements by using signal processing techniques, such as pattern correlation. For example, both a signal made up of absolute IOP measurements taken over time and a signal made up of atmospheric pressure measurements taken over an at least partially overlapping period of time can be analyzed according to known signal processing techniques (e.g., autocorrelation, feature extraction algorithms, etc.) to identify signal features, such as peaks, patterns, etc. If matching features are identified in both signals, then one of the signals can be shifted in time with respect to the other (e.g., by the time offset between matching features) so as to correlate absolute IOP measurements and atmospheric pressure measurements which were taken concurrently. These concurrent measurements can then be used to calculate gauge IOP values. This method could be applied in addition to other synchronizing methods (e.g., as discussed with respect to FIGS. 37A and 37B).

In some embodiments, an external device, such as the one used to measure atmospheric pressure, can emit a control signal to an IOP sensing implant which causes the implant to capture an absolute IOP measurement. The external device can capture an atmospheric pressure measurement substantially concurrently with the control signal such that the absolute IOP measurement and the atmospheric pressure measurement are taken sufficiently concurrently to avoid substantial inaccuracies in the calculation of gauge IOP values. In some such embodiments, the external device can prompt the user to initiate absolute IOP and atmospheric pressure measurements at appointed times. For example, the external device may provide an indicator such as an alarm to remind the user to initiate the measurements at an appointed time. In order to initiate the measurements, the user may, for example, actuate a button, switch, etc. on the external device. This action may 1) initiate an atmospheric pressure measurement; and 2) initiate the control signal from the external device to the implanted IOP sensing implant. As just discussed, this control signal may be used to cause the IOP sensing implant to capture an absolute IOP measurement. In such embodiments, the control signal may include, or consist of, a unique correlation ID number, or other uniquely identifying characteristic as described previously herein, which would enable the measurements of the IOP sensing implant and the external device to be correctly correlated even in the case that a control signal was not properly received by the IOP sensing implant. The external device may be provided in a kit with information which indicates that the user should bring the external device in proximity to his or her eye when performing this operation so as to improve communication of the control signal to the IOP sensing implant.

In some embodiments, the IOP sensing implant may include a low power clock—which may be relatively inaccurate—to initiate a ready state in which the implant can receive a signal from an external device. For example, the low power clock may cause the implant to enter this ready state for a window of time during which a signal such as those described herein (e.g., synchronization signal, control signal, etc.) is expected to be received from an external device. This period may be, for example, a 1, 5, 10, 30, or 60 minute window about the time when a signal is expected from the external device. This scheme may be beneficial because it may allow for the use of radio signals rather than signals sent via inductive coupling. While radio signals can travel further, they may lack the power needed to wake up the implant from a sleep state. For radio signals to be used, typically the IOP sensing implant needs to have a radio circuit powered on and ready to receive the signal. It can be advantageous, though, to use the low-power clock to shut down the radio circuit except during the ready period when a signal is expected from the external device. In some embodiments, the low power clock can be synched to the correct time at various intervals by an external device (e.g., during a charging or data download interaction).

Compensation for Variations in Temperature

The IOP sensing implants described herein may be affected by temperature. Although the temperature inside the eye is somewhat stabilized against large swings, it can still vary by about ±5° depending on, for example, the ambient temperature and whether the eyelid is open or closed. In addition, body temperature can vary somewhat from person to person, as well as over time for an individual user, due to fever or other individualized factors. Certain components of an IOP sensing implant, such as, for example, the sensing module itself, an onboard timekeeping device, or other electronic circuitry, may be affected by such temperature variations. Therefore, in some embodiments, a temperature sensor may be provided to capture temperature measurements over time. The temperature sensor may be provided in the IOP sensing implant itself, in a secondary intraocular implant (e.g., a drug delivery implant or a drainage implant) that is communicatively coupled to the IOP sensing implant (or to an external device that is also communicatively coupled to the IOP sensing implant), and/or in an external device such as those described herein. These temperature measurements can be used to at least partially compensate for the effect of temperature variations on one or more components of the IOP sensing implant.

Figure 38:
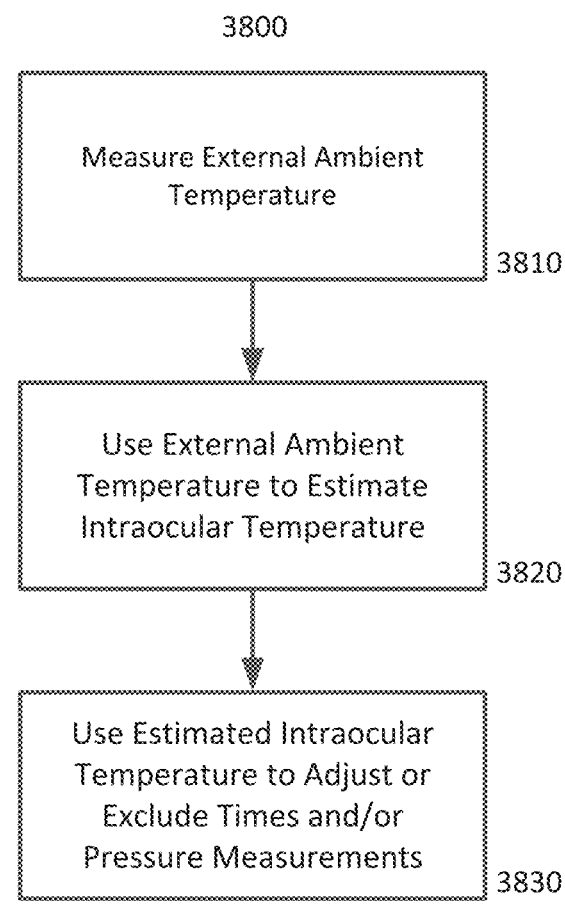
FIG. 38 is a flowchart which illustrates a method for at least partially compensating for the effect of temperature variations on an IOP sensing implant.

FIG. 38 is a flowchart which illustrates a method 3800 for at least partially compensating for the effect of temperature variations on an IOP sensing implant. The method 3800 begins with block 3810 where the external ambient temperature is measured. In some embodiments, this is accomplished using a temperature sensor that is provided as part of an external device that is worn or carried by the patient. The external device can be, for example, the same device which is used to capture atmospheric pressure measurements or to download measurements from the IOP sensing implant. At block 3820, the external ambient temperature is used to estimate the intraocular temperature which is being experienced by the IOP sensing implant. This can be done, for example, using calibration information which relates external ambient temperatures to intraocular temperatures based on measurements taken during controlled experiments.

Then, at block 3830, the estimated intraocular temperature can be used to adjust IOP measurements taken by the IOP sensing implant, the time of the implant's onboard timekeeping device, or any other characteristic of the implant which is affected by temperature. Such adjustments can be performed on IOP measurement values and/or times by a processor in post processing after data is downloaded from the implant. The adjustments may be determined using, for example, calibration data which relates one or more temperature measurements to one or more corresponding adjustments. In some embodiments, the temperature information may additionally, or alternatively, be used simply to exclude certain measurements. For example, if a temperature measurement exceeds a set threshold, lies outside a set range, varies more than a specified amount over time, etc., then IOP measurements captured during that time period can be disregarded or otherwise excluded.

In other embodiments, the temperature sensor may be provided onboard the IOP sensing implant itself. In such embodiments, temperature measurements can be recorded and logged over time just as IOP measurements. The temperature measurements can likewise be downloaded from the sensing implant and used in post processing, as just discussed, to at least partially compensate for the effect of temperature variations on the sensing implant.

Power Supplies

The various IOP sensing implants described herein can include one or more power supply devices to provide operating power for the various components of the IOP sensing implants. In some embodiments, an IOP sensing implant can include two separate power supply devices of different types. A first power supply device can be, for example, a battery, while a second power supply device can be, for example, a capacitor or supercapacitor. These separate power supply devices can collectively supply operating power for the IOP sensing implant.

While batteries can hold much greater amounts of energy than capacitors, capacitors offer the advantage of being capable of being re-charged very quickly (e.g., within just seconds or less). This characteristic is especially advantageous for supercapacitors because of their relatively large energy storage capacity as compared to other types of capacitors. Supercapacitors are capable of storing 1-2 orders of magnitude, or more, of energy per unit volume or mass than, for example, electrolytic capacitors. Unlike a solid dielectric used by other capacitors, supercapacitors may also employ, for example, electrostatic double-layer capacitance and/or electrochemical pseudocapacitance in order to store energy. Some energy storage devices may possess combinations of physical, chemical, or behavioral properties that make their classification as a battery, capacitor, or super capacitor somewhat indeterminate. In some embodiments, a supercapacitor may be considered as having 1-2 orders of magnitude less storage capacity per unit volume or mass than a battery as well as the capability to be fully charged within a comparatively short time period (e.g., 1-10 seconds) by the application of an appropriate voltage.

The IOP sensing implant may include a circuit with separate physical connections to the battery and to the supercapacitor (e.g., one pair of pads for each power source). The circuit may also include a third, separate pair of pads for the inductor coil (antenna). When the external inductive field is present, the circuit may cause a voltage to be applied to both the supercapacitor and the battery, with a source current to charge both of them. The voltage may remain on while the external inductive field is present (the supercapacitor will charge relatively quickly to that voltage and the battery will continue to draw current for a longer period of time). The supercapacitor and battery can be connected to the same charge circuit in parallel with the same charging voltage applied. This configuration may be advantageous because it does not require complex charging circuitry. However, in other embodiments, there could also be two different charge circuits—one to charge the supercapacitor and another to charge the battery (possibly with different voltages and/or currents).

For discharging, in some embodiments the supercapacitor and the battery are not connected in parallel. Instead, the IOP sensing implant may be powered from the supercapacitor until its charge is depleted and then the implant may switch to use the battery. Alternatively, the supercapacitor may be used to charge the battery (while the battery powers the implant). This approach could introduce energy losses during the charging of the battery, but could be an advantageous approach if, for example, the self-discharge rate of the supercapacitor is high.

Figure 39A:
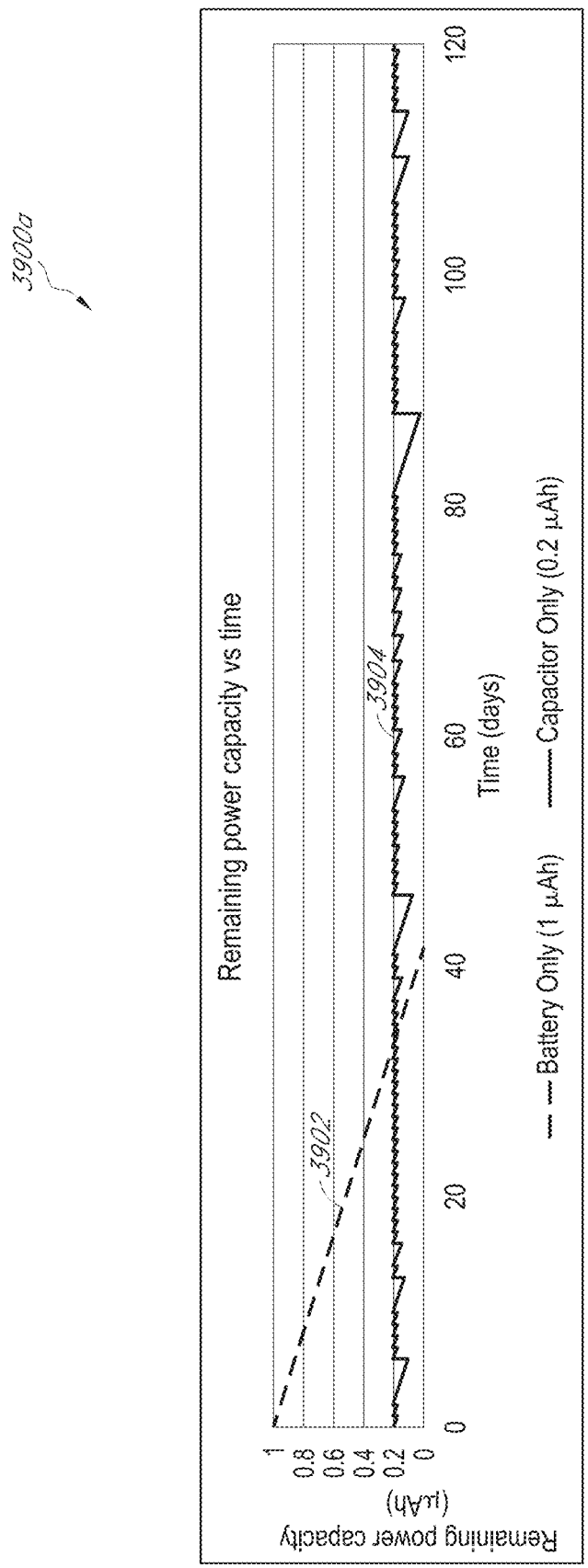
FIG. 39A is a graph which shows the power usage of an example IOP sensing implant in the case where the implant is powered by a battery and, separately, for the case where the implant is powered by a supercapacitor.

FIG. 39A is a graph 3900a which shows the power usage of an example IOP sensing implant in the case where the implant is powered by a battery (i.e., signal 3902) and, separately, for the case where the implant is powered by a supercapacitor (i.e., signal 3904). Signal 3902 illustrates the first case where the IOP sensing implant is powered solely by a battery. In this example, the IOP sensing implant is assumed to use 1 nAh of electrical energy per hour and the battery is assumed to have a usable storage capacity of 1 μAh. As shown by the signal 3902, the plotted remaining power capacity starts at 1 μAh and linearly decreases at a rate of 1 nAh per hour until all of the stored energy in the battery is exhausted after approximately 41 days.

Meanwhile, signal 3904 illustrates the second case where the IOP sensing implant is powered solely by a supercapacitor. In the case where the IOP sensing implant is powered at least partially by a supercapacitor, the IOP sensing implant may be part of a system which is designed to prompt the patient to perform charging interactions, or to more frequently perform charging interactions, with the IOP sensing implant. In such embodiments, an external charging device can be provided for wirelessly charging the IOP sensing implant. Wireless power transfer from the external device to the IOP sensing implant can be performed using electromagnetic energy, such as radio frequency (RF) energy, infrared (IR) energy, etc. The electromagnetic energy can be transferred by, for example, inductive coupling, propagating waves, etc. The external charging device can include, for example, a charging power source, a transmitter, and an antenna or inductive coupling element. The IOP sensing implant can likewise include an antenna or inductive coupling element to receive power from the external charging device.

In addition, the external charging device can also include an output device, such as a speaker, a display, a haptic transducer, etc. The output device can be used by the external charging device to provide prompts to the patient to perform charging interactions with the IOP sensing implant. Such prompts can be provided at regular intervals (e.g., daily, every 12 hours, weekly, etc.). Or the prompts can be provided at irregular intervals based on some criterion (e.g., when the supercapacitor has a predetermined percentage of power capacity remaining). The prompts may take the form of, for example, an audible cue, such as an alarm. In other embodiments, the prompt may be a visual cue, such as a certain symbol or text on a display. In still other embodiments, the prompt may take some other form, such as, for example, a haptic cue.

A charging interaction prompt can coincide with a timer synchronization prompt and/or a data download prompt. In such embodiments, use of a supercapacitor power source may have a synergistic effect because the user may already be required to perform regular timer synchronization interactions (e.g., due to time-keeping drift onboard the IOP sensing implant, as discussed herein) and/or data downloads (due to limited memory capacity) using, for example, inductive coupling. These interactions can be taken advantage of to also charge the supercapacitor. Accordingly, it may be possible to eliminate or reduce the frequency, and associated inconvenience, of battery recharges (which may otherwise require 30-45 minutes of wearing a special charging device).

The charging interactions themselves can take many forms. For example, the patient may be required to manipulate a control on the external charging device, such as a button, switch, etc. Manipulation of the control can cause the external charging device to initiate the wireless transfer of power from the external charging device to the IOP sensing implant. The control can also initiate the synchronization of timekeeping devices, the downloading of data from the IOP sensing implant, etc., as discussed elsewhere herein.

In some embodiments, the external charging device may include or be accompanied by usage instructions which indicate to the user that he or she should bring the external charging device in proximity to his or her eye as part of the charging interaction. Closer physical proximity between the external power charging device and the IOP sensing implant will generally improve power transfer to the implant. In some embodiments, the external charging device may repeatedly or continuously provide the prompt until sensing that the user has carried out the charging interaction. Since the power source is a supercapacitor, the charging interaction may only take seconds or less, thus making it practical to conduct frequent charging interactions.

In some embodiments, the external charging device may be set to provide the charging prompt at intervals of time such that the expected energy usage of the IOP sensing implant during the interval is less than the storage capacity of the supercapacitor. For example, for the case illustrated by signal 3904, the IOP sensing implant is assumed to use 1 nAh of electrical energy per hour and the supercapacitor is assumed to have a usable storage capacity of 0.2 μAh. Thus, the supercapacitor can provide sufficient energy to power the IOP sensing implant for several days. So long as the external charging device prompts the user to conduct charging interactions with the IOP sensing implant at intervals which are shorter than this expected operation time (and assuming the user actually conducts the prompted charging interactions), then the IOP sensing implant can operate continuously. For example, signal 3904 shows that charging interactions are prompted—and generally performed—daily. However, even if the patient ignores the charging interaction prompt for a few days at a time (as indicated by the larger teeth in the sawtooth signal waveform 3904), the IOP sensing implant can still be operated continuously because the supercapacitor is capable of storing adequate energy to power the device for a few days at a time. The expected energy usage of the IOP sensing implant can be determined in a variety of ways, including experimentally during typical usage conditions or analytically based on rated power usage of the various components of the sensing implant.

Figure 39B:
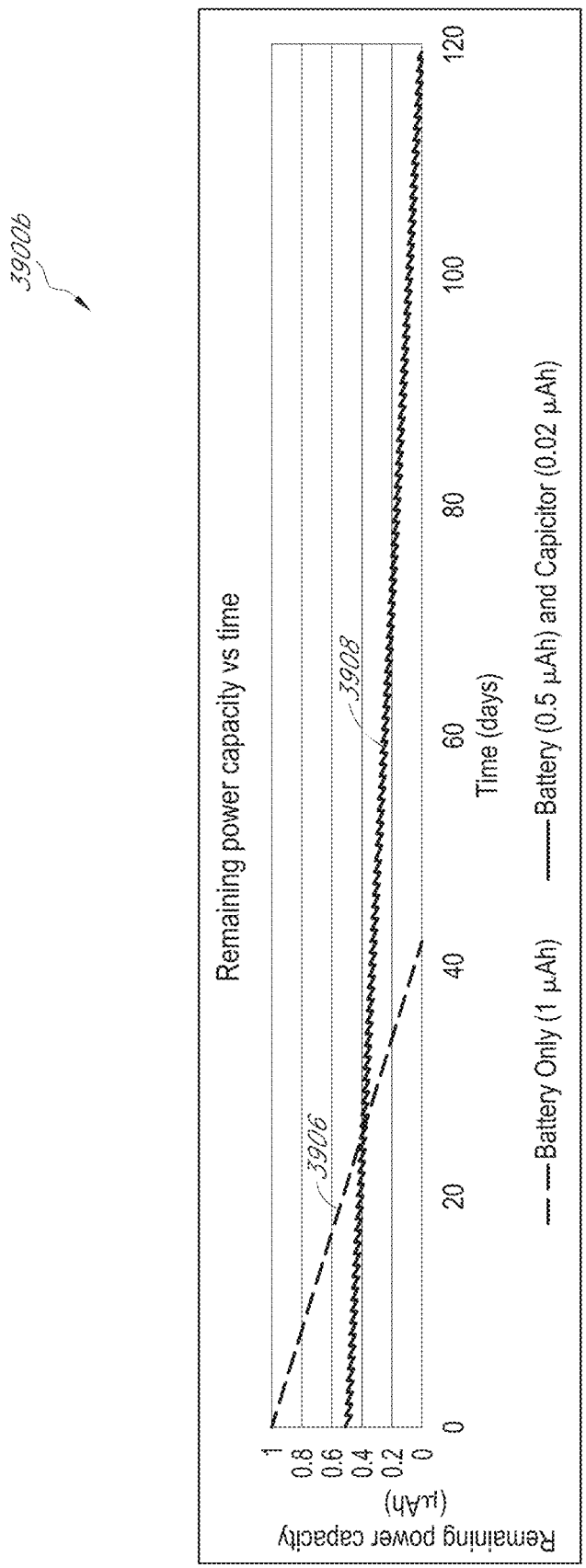
FIG. 39B is a graph which shows the power usage of an example IOP sensing implant that is powered by the combination of a battery and a supercapacitor, where the capacity of the supercapacitor is less than the power usage of the implant between charging interaction times.

FIG. 39B is a graph 3900b which shows the power usage of an example IOP sensing implant that is powered by the combination of a battery and a supercapacitor, where the capacity of the supercapacitor is less than the power usage of the implant between charging interaction times. In the example illustrated by signal 3908, the IOP sensing implant consumes 1 nAh of electrical power per hour, while the battery has a storage capacity of 0.5 μAh and the supercapacitor has a storage capacity of 0.02 μAh. As just described with respect to FIG. 39A, the IOP sensing implant can be part of a system which includes an external charging device which occasionally prompts the patient to perform a charging interaction to charge the supercapacitor. (As mentioned above, the charging interaction prompt can also serve as, or coincide with, timer synchronization prompts and/or data download prompts.) In the example illustrated by signal 3908, the external charging device outputs the charging interaction prompt daily and the supercapacitor is therefore re-charged daily so long as the patient adheres to the prompt. This is evident from the 0.02 μAh sawtooth pattern which is evident in the signal 3908, where the supercapacitor is charged and then drops in remaining capacity until being re-charged once again. The 0.02 μAh storage capacity of the supercapacitor in this example is slightly less than the expected energy usage of 0.024 μAh by the IOP sensing implant between the daily charging interaction times.

For comparison purposes, FIG. 39B also includes a signal 3906, which illustrates a case where the IOP sensing implant is powered solely by a battery with a storage capacity of 1 μAh—double the storage capacity of the battery represented by signal 3908. As shown by the signal 3906, this battery capacity is sufficient to power the IOP sensing implant for approximately 41 days. But notwithstanding the fact that the battery corresponding to signal 3906 has twice the capacity as the battery corresponding to signal 3908, the IOP sensing implant corresponding to signal 3908 can operate approximately 3 times longer than the IOP sensing implant corresponding to signal 3906. This is due to the presence of the supercapacitor combined with regular (e.g., daily) charging interaction. This example illustrates the synergy which can be achieved by using even a relatively small-capacity supercapacitor in conjunction with a battery to supply operating power to the IOP sensing implant.

Figure 39C:
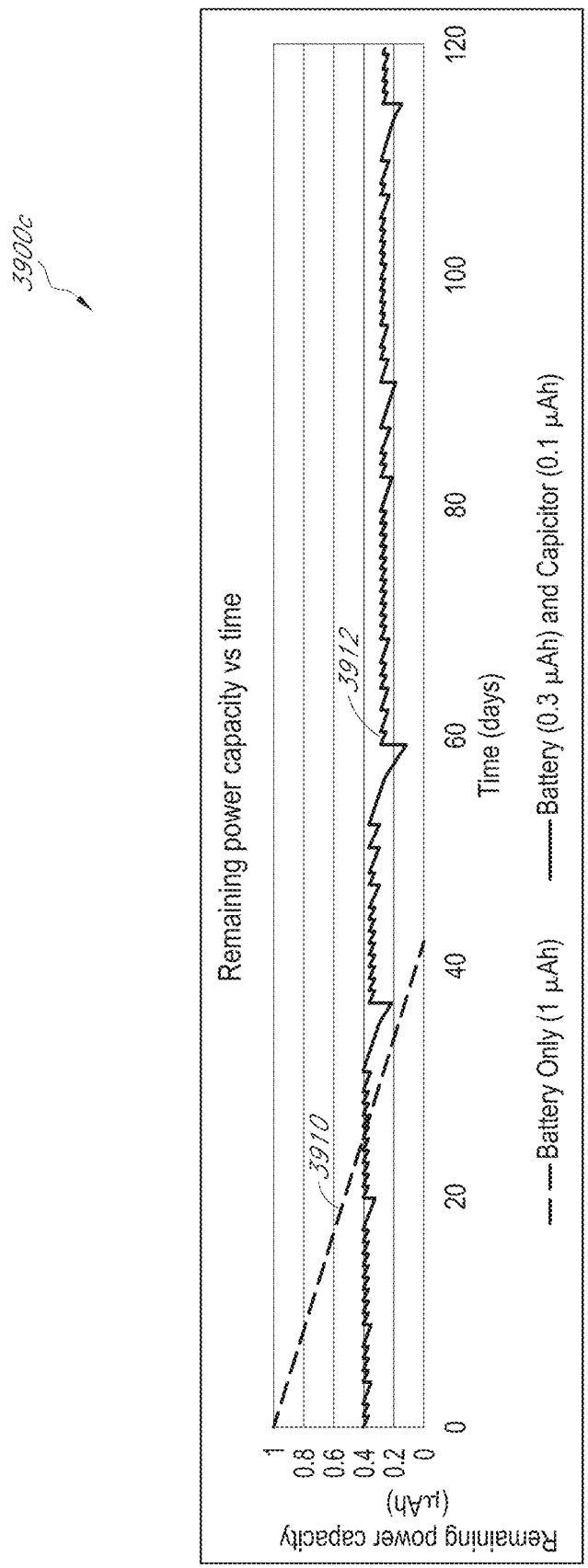
FIG. 39C is a graph which shows the power usage of an example IOP sensing implant that is powered by the combination of a battery and a supercapacitor, where the capacity of the supercapacitor is greater than the power usage of the implant between charging interaction times.

FIG. 39C is a graph 3900c which shows the power usage of an example IOP sensing implant that is powered by the combination of a battery and a supercapacitor, where the capacity of the supercapacitor is greater than the power usage of the implant between charging interaction times. In the example illustrated by signal 3912, the IOP sensing implant once again consumes 1 nAh of electrical power per hour, while the battery has a storage capacity of only 0.3 μAh and the supercapacitor has a storage capacity of 0.1 μAh. Once again, the IOP sensing implant can be part of a system which includes an external charging device which occasionally prompts the patient to perform a charging interaction to charge the supercapacitor. In the example illustrated by signal 3912, the external charging device outputs the charging interaction prompt daily and the supercapacitor is therefore generally re-charged daily, though allowance is made for these charging interactions to be occasionally skipped.

For comparison purposes, FIG. 39C also includes a signal 3910, which illustrates a case where the IOP sensing implant is powered solely by a battery with a storage capacity of 1 μAh—more than three times the storage capacity of the battery represented by signal 3912. As shown by the signal 3910, this battery capacity is sufficient to power the IOP sensing implant for approximately 41 days. In contrast, the IOP sensing implant corresponding to signal 3912 can operate for much longer periods of time because the supercapacitor is capable of supplying all of the necessary operating power for the entire period of time between scheduled charging interaction prompts. So long as the patient adheres to these prompts and carries out the charging interactions, the battery power is not needed. However, the battery is available to supply back-up power in the event that the patient fails to adhere to one or more charging interaction prompts.

Figure 40:
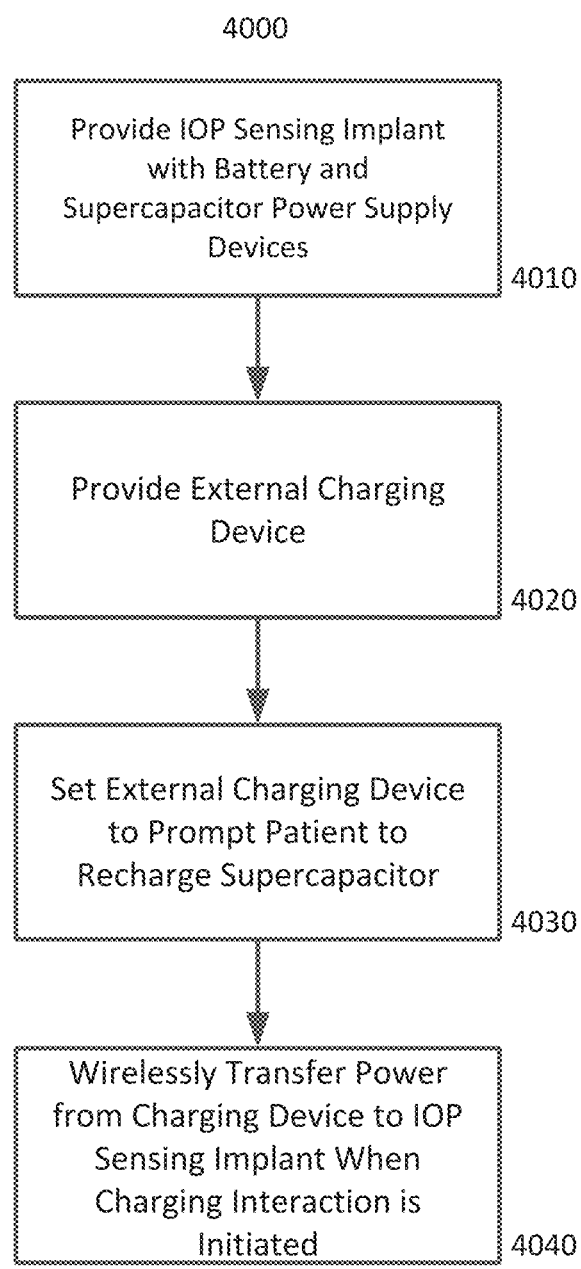
FIG. 40 is a flowchart which illustrates a method for supplying operating power to an IOP sensing implant.

FIG. 40 is a flowchart which illustrates a method 4000 for supplying operating power to an IOP sensing implant. The method 4000 begins at block 4010 where a battery and a supercapacitor are provided onboard the IOP sensing implant to provide operating power for the implant. At block 4020, an external charging device is provided. At block 4030, the external charging device is set to prompt the patient to initiate a charging interaction between the external charging device and the IOP sensing implant. Finally, at block 4040, the external charging device wirelessly transfers power to, for example, a supercapacitor onboard the IOP sensing implant when a charging interaction is initiated. As already discussed, charging interactions can be prompted by the external charging device at, for example, regular intervals or based on satisfaction of some criterion.

Laser Welding of Main Housing and Sensor Cap of IOP Sensing Implant

As already discussed above, various embodiments of the IOP sensing implants disclosed herein can include a main tubular housing (e.g., 2102) and a sensor cap (e.g., 2108) which mates with the main housing, though other types of combinable housing parts can also be used. The sensor cap can be designed to press into one end of the main housing. A moisture barrier seal can be provided or formed between the sensor cap and the main housing.

Figure 41:
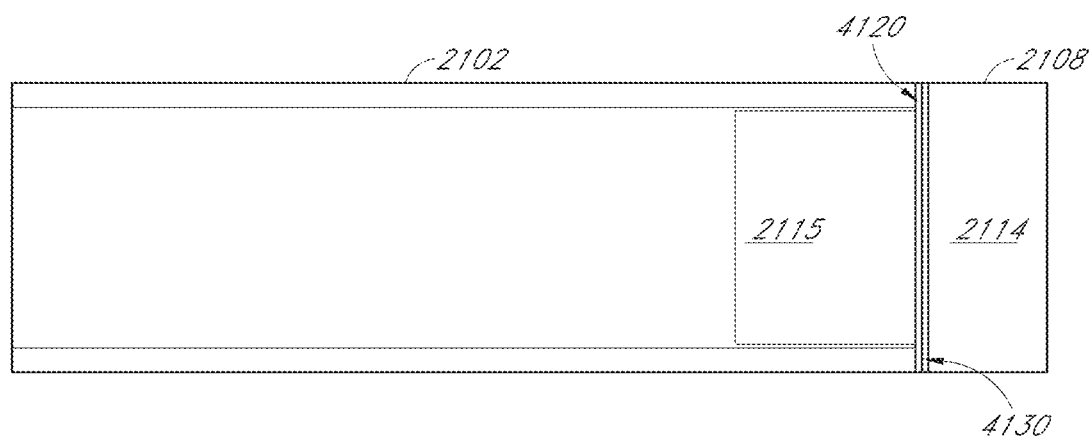
FIG. 41 illustrates an embodiment of a sensor cap inserted into a main housing of an IOP sensing implant with a moisture barrier seal formed between the sensor cap and the main housing.

FIG. 41 illustrates an embodiment of a sensor cap 2108 inserted into a main housing 2102 with a moisture barrier seal formed therebetween. In some embodiments, the sensor cap 2108 has a bi-diameter design with a plug portion 2115 and a head portion 2114. The plug portion 2115 can be sized so as to be snugly insertable into the main body 2102 of the housing. For example, the diameter of the plug portion 2115 can be equal to, or just smaller (e.g., <5% smaller, <1% smaller, <0.1% smaller, <0.01% smaller, <0.001% smaller), than the inner diameter of the main body 2102. The head portion 2114, in contrast, may have a diameter which is larger than the inner diameter of the main body 2102. A shoulder therefore results at the junction between the plug portion 2115 and the head portion 2114. When the sensor cap 2108 is inserted into the main housing 2102, this shoulder serves as a mechanical stop which abuts against a mating surface 4120 of the main housing 2102. In some embodiments, the mating surface 4120 is located at the end of the sidewall of the main housing 2102 and is oriented perpendicular to the axis of the main housing 2102 (i.e., perpendicular to the insertion axis of the sensor cap 2108). This abutment between the shoulder of the sensor cap 2114 and the main housing 2102 is advantageous because it helps to ensure correct positioning of the sensor cap 2114 within the main housing 2102.

In some embodiments, the moisture barrier seal between the main housing 2102 and the sensor cap 2108 is formed by welding these two structures together at the mating surface. This can be accomplished by providing, for example, a metal interlayer 4130 at the location of the mating surface 4120. This metal interlayer 4130 can be formed or provided on or adjacent to either the main housing 2102 or the sensor cap 2108 at the location of the mating surface 4120. For example, the metal interlayer 4130 can be a ring with an inner diameter equal to or larger than the diameter of the plug portion 2115 of the sensor cap 2108 and an outer diameter that is preferably smaller than the diameter of the head portion 2114 of the sensor cap 2108. Then, a laser can be used to apply heat to the metal interlayer 4130 so as to melt it and fuse the main housing 2102 and the sensor cap 2108 together at the mating surface 4120. The laser can have an operating wavelength which causes the laser to be substantially transparent to the material of the main housing 2102 and/or the sensor cap 2108. For example, the main housing 2102 and/or the sensor cap 2108 may be made of silicon and the welding laser may have an operating wavelength (e.g., in the infrared spectrum) which is not substantially absorbed by the silicon. In this way, the laser light can pass through the structure of the main housing 2102 and/or the sensor cap 2108 until it impinges upon the metal interlayer 4130, which absorbs, and is heated by, the laser light, causing the metal interlayer to form a welded interface between the main housing 2102 and the sensor cap 2108. In some embodiments, light from the welding laser is applied through the head portion 2114 of the sensor cap 2108 toward the mating surface.

Bi-Diameter Main Housing for IOP Sensing Implant

Figure 42A:
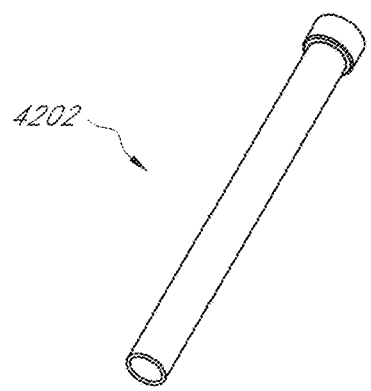
FIG. 42A is a perspective view of an embodiment of an IOP sensing implant with a bi-diameter main housing.
Figure 42B:
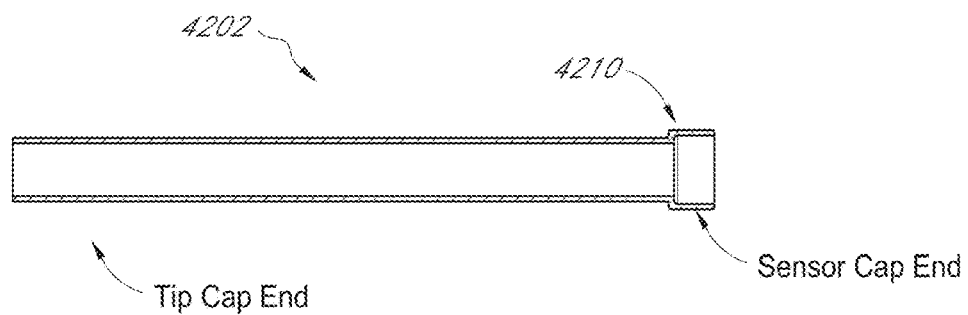
FIG. 42B is a side view of the bi-diameter main housing shown in FIG. 42A.

FIG. 42A is a perspective view of an embodiment of an IOP sensing implant with a bi-diameter main housing 4202. FIG. 42B is a side view of the bi-diameter main housing 4202 shown in FIG. 42A. The bi-diameter main housing 4202 can be similar to other main housings described herein (e.g., the main housing 2102 shown in FIG. 21 and elsewhere) in that it can be an elongate tubular body designed to receive a tip cap (e.g., 2102) and a sensor cap (e.g., 2108) at opposite ends. The end which receives the tip cap will be referenced as the tip cap end, while the end which receives the sensor cap will be referenced as the sensor cap end. The bi-diameter main housing 4202 can have a first diameter at the tip cap end and a second, larger diameter at the sensor cap end. In some embodiments, the diameter of the sensor cap end may be at least 10%, and as much as 300%, larger than the diameter of the tip cap end. A shoulder 4210 can join the smaller-diameter (tip cap end) and the larger-diameter (sensor cap end) portions of the bi-diameter main housing 4202. In some embodiments, the tip cap end of the main housing can have a constant first diameter, and the sensor cap end of the main housing can have a constant second, larger diameter, though this is not required.

Figure 42C:
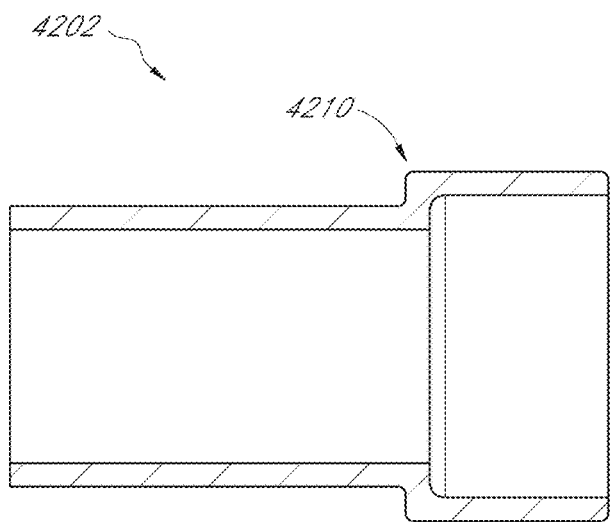
FIG. 42C illustrates a magnified view of the region around the shoulder of the bi-diameter main housing shown in FIGS. 42A and 42B.

FIG. 42C illustrates a magnified view of the region around the shoulder 4210 of the bi-diameter main housing 4202 shown in FIGS. 42A and 42B. As shown in FIG. 42C, in some embodiments, the shoulder 4210 can be a step transition between the smaller-diameter (tip cap end) and the larger-diameter (sensor cap end) portions of the bi-diameter main housing 4202. In other words, the shoulder 4210 can be formed as one or more surfaces which join the smaller-diameter and the larger-diameter portions of the main housing 4202 and which are generally perpendicular to the axis of the elongate main housing 4202. Alternatively, the shoulder can be a tapered transition between the smaller-diameter and the larger-diameter portions of the main housing.

As already discussed herein, the IOP sensing implant can be sized and shaped for insertion into certain ocular anatomical structures, such as the supraciliary/suprachoroidal space. The bi-diameter design of the main housing 4202 can be advantageous in such embodiments because the shoulder 4210 can serve as a mechanical stop when inserting the IOP sensing implant (tip cap end first) into ocular tissue. This can help to ensure that the IOP sensing implant is properly positioned in the ocular tissue. For example, the shoulder 4210 of the bi-diameter main housing 4202 can help prevent over-insertion of the IOP sensing implant into the supraciliary/suprachoroidal space. This in turn helps to ensure that the sensor cap end at least partially extends into the anterior chamber of the eye so as to measure IOP in the anterior chamber. The distance from the shoulder 4210 to the furthest extent of the sensor cap end of the IOP sensing implant can correspond to the desired distance that the IOP sensing implant is to extend into the anterior chamber from the ocular tissue where the implant is anchored. Additional benefits of the bi-diameter design of the main housing 4202 include that the smaller diameter of the tip cap end helps to provide for easier insertion into ocular tissue, while the larger diameter of the sensor cap end can accommodate a larger IOP sensing module.

While FIGS. 42A-42C illustrate a shoulder 4210 in the main housing 4202 which serves as a mechanical stop to prevent over-insertion of the IOP sensing implant in ocular tissue, other designs for mechanical stops are also possible. For example, the main housing could alternatively and/or additionally include one or more ridges, flanges, or other structures which project radially from the housing, and wholly or partially surround the circumference of the housing, so as to act as a mechanical stop when inserting the implant into ocular tissue.

Cupped Sensor Cap Design

Figure 43A:
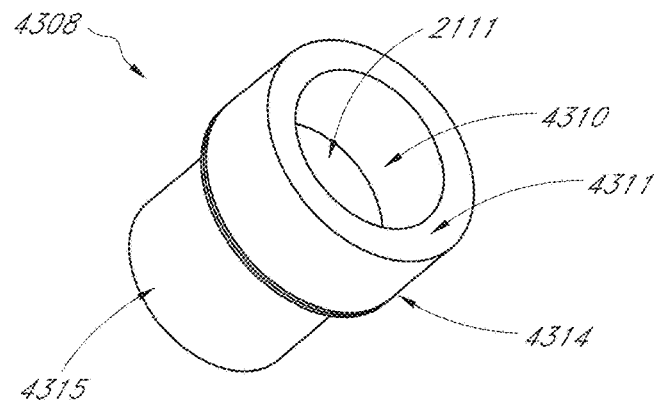
FIG. 43A is a perspective view of a cupped sensor cap for an intraocular pressure sensing implant.

FIG. 43A is a perspective view of a cupped sensor cap 4308 for an intraocular pressure sensing implant. In the illustrated embodiment, the sensor cap 4308 is implemented as a bi-diameter sensor cap which includes a plug portion 4315 that is designed to be inserted into the main housing (e.g., 2102, 4202) of the implant and a head portion 4314 that extends from the plug portion 4315. The IOP sensing module may be provided, for example, wholly in the head portion 4314 or partially in the head portion and partially in the plug portion 4315. The head portion 4314 of the sensor cap 4308 has a concave shape in that it includes a depression 4310 formed in the outward-facing portion of the cap 4308. The depression 4310 is formed in the central portion of the sensor cap and is surrounded by a peripheral wall 4311. The IOP sensing module of the sensor cap can be formed in the depression 4310 so that it is surrounded by the peripheral wall 4311. In some embodiments, the IOP sensing module includes a flexible diaphragm 2111 which is part of a pressure sensing module (e.g., a capacitive or piezoresistive pressure sensing module). As the flexible diaphragm 2111 may be delicate, its location in the depression 4310 of the sensor cap 4308, surrounded by the peripheral wall 4311, offers a measure of protection against damage when the implant is being handled or manipulated prior to, and during, surgical implantation. Other pressure sensing devices may also benefit from the physical protection offered by the cupped sensor cap design shown in FIG. 43A. While FIG. 43A illustrates a bi-diameter sensor cap 4308 design, other types of housings can likewise include cupped regions (e.g., at a distal location) like the one illustrated in FIG. 43A.

Figure 43B:
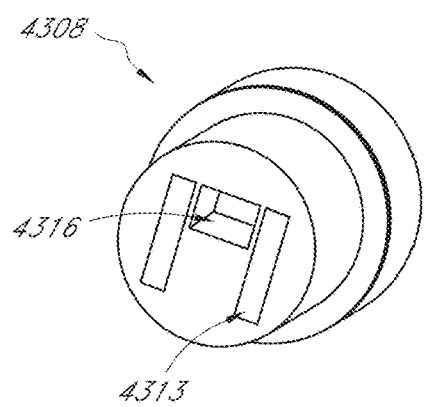
FIG. 43B is another perspective view of the cupped sensor cap but from the opposite side of what is shown in FIG. 43A.
Figure 43C:
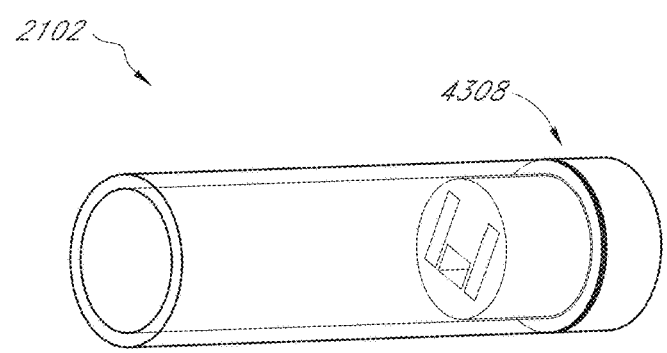
FIG. 43C is yet another perspective view of the cupped sensor cap but this time as mounted in a tubular main body of the IOP sensor implant housing.

FIG. 43B is another perspective view of the cupped sensor cap 4308 but from the opposite side of what is shown in FIG. 43A. As is evident in FIG. 43B, the sensor cap 4308 can, like other embodiments of sensor caps disclosed herein (e.g., 2108), include a cutout 4316 to physically connect with a carrier member (e.g., 2072) which has various electronic components mounted thereon. In addition, the sensor cap 4308 can include one or more electrical contacts 4313 to electrically connect the IOP sensing module located in the sensor cap 4308 with one or more other electrical components in the IOP sensing implant. FIG. 43C is yet another perspective view of the cupped sensor cap 4308 but this time as mounted in a tubular main body 2102 of the IOP sensor implant housing.

Although the cupped design of the sensor cap 4308 in FIG. 43A is advantageous for its protective properties, it may also pose some complications which could affect the capability of the IOP sensing module—located in the depression 4310 of the sensor cap—to operate within the eye. For example, the depression 4310 in the sensor cap may have a tendency to trap an air pocket adjacent to the IOP sensing module when the implant is inserted into the eye. If an air pocket were to be trapped by the peripheral wall 4311 inside the depression 4310, it could act as a barrier between the IOP sensing module and the aqueous humor. Although an air pocket may at least partially transmit pressure from the aqueous to the sensing module, it is also possible that an air pocket which fills, or partially fills, the depression 4310 may negatively impact the accuracy of IOP measurements due to forces generated by surface tension at the interfaces of the air pocket and aqueous and/or flexible diaphragm 2111, or due to other effects such as affecting the parasitic capacitance acting on the IOP sensing module. This potential problem may be at least partially ameliorated by providing a hydrophilic coating on the inside of the depression 4310 of the sensor cap 4308. For example, the inside of the peripheral wall 4311 may be coated with a hydrophilic material. Similarly, the flexible diaphragm 2111 located at the bottom of the depression 4310 may likewise be coated with a hydrophilic material. The presence of the hydrophilic material within the depression 4310 of the sensor cap may facilitate priming of the depression with aqueous humor. Examples of suitable hydrophilic materials include various oxides including silicon oxide, titanium oxide, tantalum oxide, etc., various nitrides including silicon nitride, titanium nitride, tantalum nitride, etc., various carbides including silicon carbide, titanium carbide, etc. Such materials may be deposited as a thin layer using atomic layer deposition (ALD), physical vapor deposition (PVD) methods such as sputtering or evaporation, or chemical vapor deposition (CVD), among other methods. Other materials may be applied as a thin film to create a hydrophilic surface including biomaterials such as heparin, poly-L-lysine, etc. Alternatively and/or additionally, the hydrophilicity of the hydrophilic surfaces of the inside of the peripheral wall 4311 and/or flexible diaphragm 2111 may be increased by increasing the surface roughness using a variety of means such as dry or wet chemical etching or physical etching such as ion bombardment. Such roughening may be performed before, after, or in place of coating with a hydrophilic material. Alternatively and/or additionally, the potential problem of the cupped region of the sensor cap 4308 failing to prime with aqueous humor can be reduced or eliminated by using a special delivery apparatus to surgically insert the implant.

Figure 44:
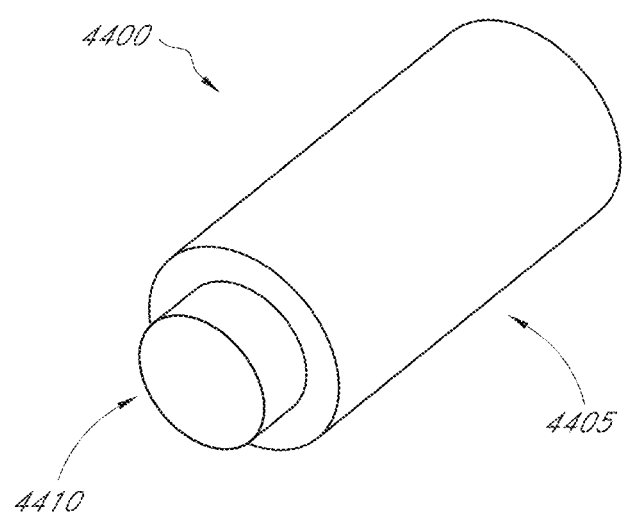
FIG. 44 illustrates an embodiment of a distal portion of a delivery apparatus for surgically inserting an IOP sensing implant having a cupped sensor cap.

FIG. 44 illustrates an embodiment of a distal portion 4400 of a delivery apparatus for surgically inserting an IOP sensing implant having a cupped sensor cap. The delivery apparatus can include, for example, a handpiece, a holder, a delivery mechanism, a plunger, etc., as described elsewhere herein. The distal portion 4400 of the delivery apparatus is the portion of the delivery apparatus which is in contact with the IOP sensing implant during surgical implantation. In some embodiments, the distal portion 4400 of the delivery apparatus is a plunger tip. The plunger tip can include, for example, a main body 4405 and a projection 4410 which is used to engage the concave portion of the sensor cap 4308. The projection 4410 can be the physical complement of the depression 4310 formed in the sensor cap 4308. In the illustrated embodiment, the projection 4410 has a diameter which is no larger than the diameter of the depression 4310 in the sensor cap 4308, while the main body 4405 of the distal portion 4400 of the delivery apparatus has a diameter which is larger than that of the depression 4310 in the sensor cap 4308. This results in a shoulder where the projection 4410 is joined with the main body 4405. The length of the projection 4410 from the main body 4405 may be, for example, less than or equal to the depth of the depression 4310 in the sensor cap 4308. When the projection 4410 is inserted into the depression 4310 of the sensor cap 4308, the shoulder may engage with the peripheral wall 4311 of the sensor cap. This engagement may prevent over insertion of the projection 4410 into the depression 4310 of the sensor cap 4308, which could otherwise damage the IOP sensing module located in the depression.

As discussed elsewhere herein, the delivery apparatus can be used to surgically insert the IOP sensing implant at the desired location within the eye. Once the IOP sensing implant is released from the delivery apparatus, the projection 4410 is withdrawn from the depression 4310 in the sensor cap 4308. The withdrawal of the projection 4410 creates a vacuum which draws aqueous humor into the depression 4310 of the sensor cap 4308, thereby priming the depression with fluid and reducing or eliminating the amount of air trapped in the depression of the sensor cap.

In other embodiments, the depression 4310 of the sensor cap 4308 can be filled with a non-compressible, pressure-transmitting gel or other substance prior to insertion into the eye. The gel may displace air from the depression in the sensor cap. Further, once the IOP sensing implant is surgically implanted, the gel may act as a pressure-transmitting medium which can allow pressure to be exerted on the IOP sensing module (located in the depression of the sensor cap) by the aqueous humor in the eye. Examples of suitable materials for the non-compressible, pressure-transmitting gel include silicon gel, fluorosilicon gel, etc.

Sealing and Sterilizing an IOP Sensing Implant

Various embodiments of the IOP sensing implants disclosed herein include a housing made up of an elongate, tubular main body (e.g., 2102, 4202), a sensor cap (e.g., 2108, 4308), and a tip cap (e.g., 2104). As discussed elsewhere, these various parts of the IOP sensing implant housing (or other parts of another embodiment of an IOP sensing implant housing) can be assembled and hermetic seals can be provided at the junctions between the various parts so as to prevent fluid from entering the housing after it has been implanted into the eye. Notwithstanding the fact that the IOP sensing implant housing may be hermetically sealed, it nevertheless may be advantageous to sterilize the interior of the implant. Sterilization could potentially be accomplished by heating the implant to a temperature that is sufficient to kill or deactivate bacteria, viruses, etc. However, the electronic components of the IOP sensing implant may not be able to withstand such temperatures. Therefore, it may be more advantageous to perform sterilization using, for example, a sterilization agent, such as a disinfectant gas. However, this technique, too, could pose technical challenges because of difficulty in assembling, bonding, and/or sealing the various parts of the IOP sensing implant housing while concurrently injecting and evacuating the sterilization agent, or alternatively sterilizing the various parts of the IOP sensing implant, including internal parts, prior to assembling, bonding and/or sealing the parts under aseptic conditions. Thus, FIGS. 45 and 46 illustrate a technique for advantageously separating the assembling, bonding, and/or sealing step(s) from the sterilization step(s) during the manufacturing process.

Figure 45:
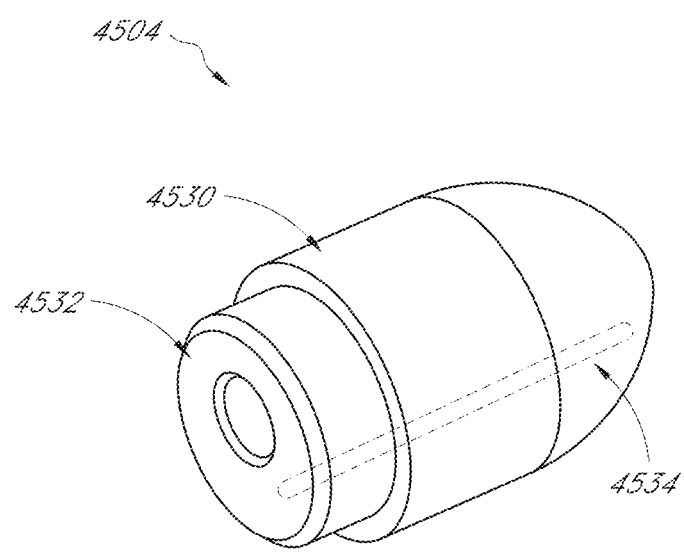
FIG. 45 illustrates an example embodiment of a tip cap that can be used to facilitate sterilization of an IOP sensing implant.

FIG. 45 illustrates an example embodiment of a tip cap 4504 that can be used to facilitate sterilization of an IOP sensing implant. Meanwhile, FIG. 46 illustrates an example method 4600 for assembling, bonding, sealing, and sterilizing the IOP sensing implant. The method begins at block 4610 by providing the various parts of the IOP sensor implant housing. As discussed elsewhere herein, the various parts of the implant housing can include, for example, an elongate tubular main body, a sensor cap, and a tip cap. These housing parts can be as described elsewhere herein, with the exception that an injection port can be provided in at least one of the housing parts so as to facilitate the injection of a sterilization agent at a later time after the housing parts have been assembled, bonded, and/or hermetically sealed.

FIG. 45, for example, illustrates a tip cap 4504 which includes an injection port 4534 to facilitate injection of a sterilization agent after the IOP sensing implant housing has been assembled, bonded, and/or hermetically sealed. The tip cap 4504 includes a plug portion 4532 that is inserted into the tubular main body of the implant housing. The diameter of the plug portion 4532 corresponds to the inner diameter of the main body. In addition, the illustrated tip cap 4504 includes a head portion 4530 which extends from the tubular main body of the implant housing when the tip cap is inserted into the main body. As discussed elsewhere, the head portion 4530 of the tip cap can be rounded and/or pointed so as to facilitate insertion of the implant housing into ocular tissue. The injection port 4534 is a passageway (shown in FIG. 45 with dotted lines) that extends from an exterior location, through the tip cap 4504, and into the tubular main body of the implant housing when the tip cap and the main body are assembled.

Figure 46:
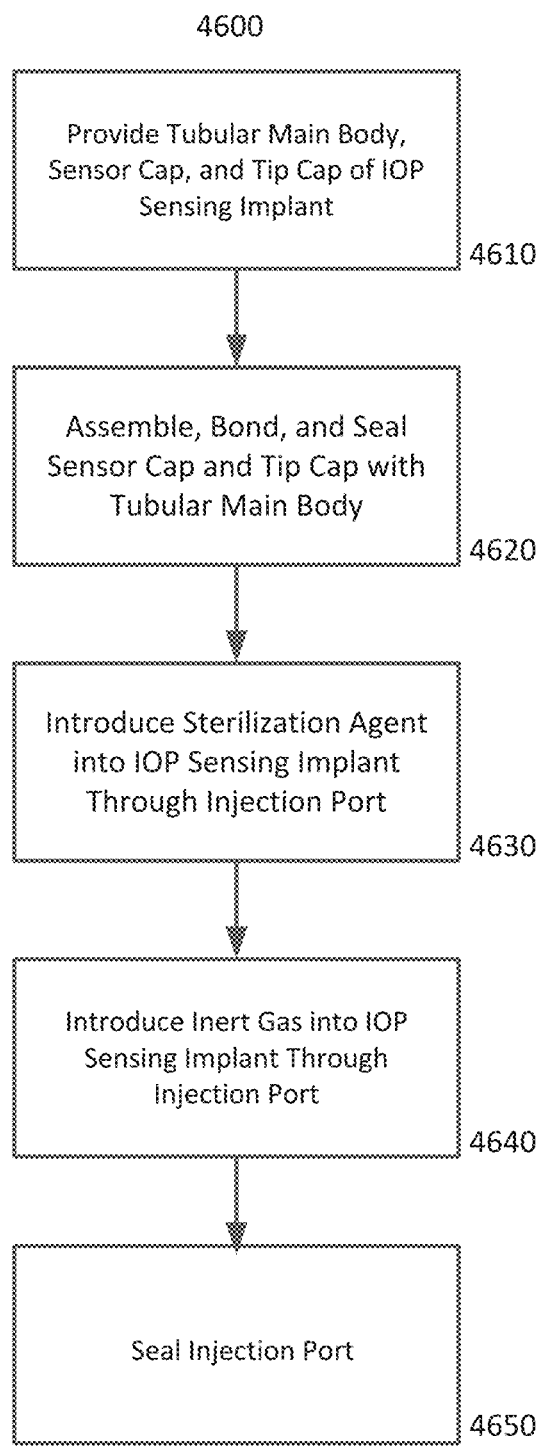
FIG. 46 illustrates an example method for assembling, bonding, sealing, and sterilizing the IOP sensing implant.

At block 4630 of the method 4600 shown in FIG. 46, the injection port 4534 in the tip cap 4504 can be used to introduce a sterilization agent, such as ethylene oxide or hydrogen peroxide, into the assembled IOP sensing implant housing. The sterilization agent can also be evacuated through the same port. Alternatively, multiple ports can be provided for injection and/or evacuation of the sterilization agent. These can be provided all in the same housing part or in different housing parts.

The fact that sterilization can be performed after the various parts of the IOP sensing implant housing have already been assembled, bonded, and/or hermetically sealed his advantageous because it simplifies both the assembly procedure and the sterilization procedure since they need not necessarily be performed concurrently.

At block 4640 an inert gas can optionally be injected into the assembled IOP sensing implant housing. For example, argon gas can be injected into the implant housing. The inert gas can advantageously extend the life of the battery inside the implant housing in the case that the battery includes lithium, which would otherwise be very reactive with the atmosphere inside the implant housing.

Finally, at block 4650, the injection port 4534 in the tip cap 4504 can be sealed. This can be accomplished in a variety of ways, including, for example, by melting the tip cap material surrounding the port (with laser energy, for example), by inserting a wire or plug (and optionally melting the wire or plug to seal the injection port), etc.

Although the sterilization technique has been described with respect to an injection port provided in the tip cap 4504, in other embodiments the injection ports may be provided in the sensor cap, in the tubular main body, or in any other housing part(s).

IOP Sensing Implant with Flow-Enabling Features

Various embodiments of the IOP sensor implants disclosed herein can be designed to be inserted/implanted/anchored at or in a physiological outflow pathway of the eye. In healthy eyes, these outflow pathways, such as Schlemm's canal (via the trabecular meshwork) or the uveoscleral outflow pathway, drain aqueous humor from the anterior chamber to prevent IOP from exceeding healthy levels.

Figure 47A:
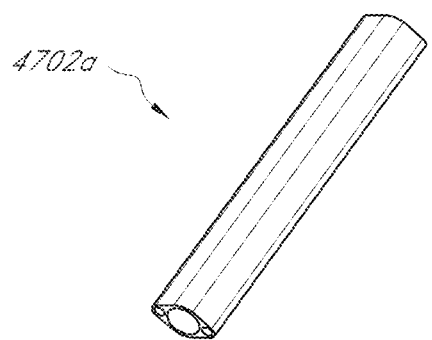
FIG. 47A is a perspective view of an example IOP sensor implant housing main body with enclosed flow-enabling features.
Figure 47B:
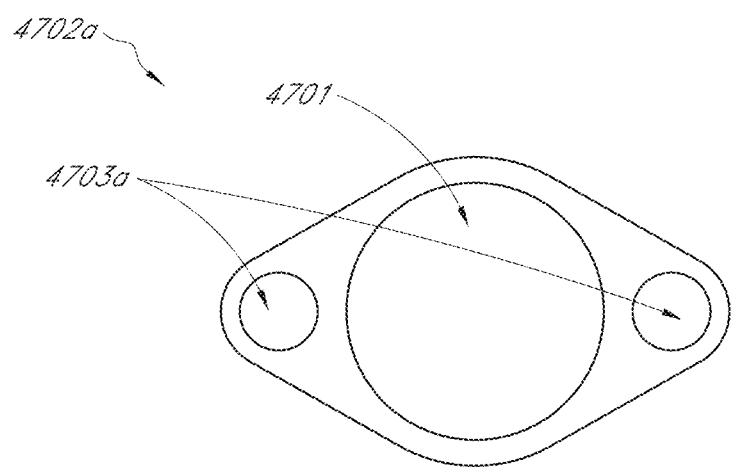
FIG. 47B is a cross-sectional view of the IOP sensor housing main body shown in FIG. 47A.
Figure 47C:
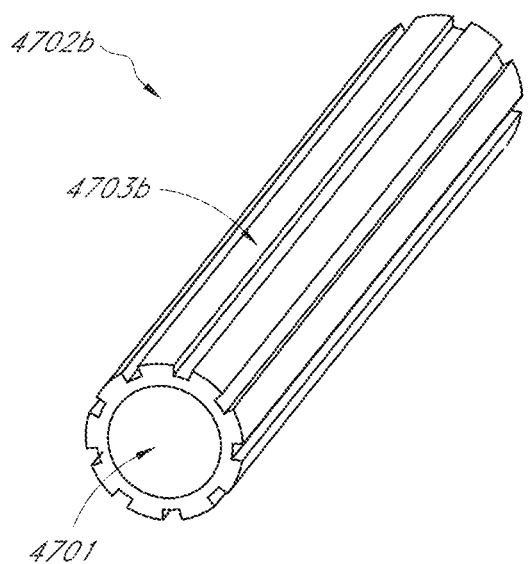
FIG. 47C is a perspective view of an example IOP sensor implant housing main body with open, external flow-enabling features.

FIGS. 47A-47C illustrates embodiments of an IOP sensor implant housing with flow-enabling features. The flow-enabling features can enhance outflow of the aqueous, thereby reducing IOP levels. The flow enabling features may be, for example, external features of the IOP sensor implant housing which are not enclosed by the housing. Alternatively, and/or additionally, the flow enabling features may be at least partially enclosed by the IOP sensor implant housing.

FIG. 47A is a perspective view of an example IOP sensor implant housing main body 4702a with enclosed flow-enabling features. FIG. 47B is a cross-sectional view of the IOP sensor housing main body 4702a shown in FIG. 47A. The housing main body 4702a can include a central main cavity 4701 to accommodate electrical components of the IOP sensor implant, as discussed elsewhere herein. In addition, the housing main body 4702a can also include one or more flow pathways 4703a. The flow pathways 4703a may have, for example, a smaller diameter than the central cavity 4701. In the embodiment illustrated in FIG. 47B, the housing main body 4702a includes two flow pathways 4703a on opposing sides of the central cavity 4701. Each of these flow pathways 4703 can be, for example, an enclosed lumen running substantially the entire axial length of the main body 4702a of the IOP sensor implant housing. When the housing is surgically implanted in, for example, a physiological outflow pathway of the eye, one end of each flow pathway 4703a can be located in the anterior chamber, while the opposite end of each flow pathway can be located in the physiological outflow pathway. The flow pathways can enhance drainage by conducting aqueous out of the anterior chamber.

As shown in FIG. 47B, the enclosed flow pathways 4703a give the main body 4702 of the implant housing a widened shape in the direction of the transverse axis. The flow pathways 4703a can advantageously occupy gaps that may otherwise exist between layers of tissue when inserting the implant in, for example, the supraciliary/suprachoroidal space.

FIG. 47C is a perspective view of an example IOP sensor implant housing main body 4702b with open, external flow-enabling features. Once again, the housing main body 4702b can include a central main cavity 4701 to accommodate electrical components of the IOP sensor implant. In addition, the housing main body 4702b can include one or more open, external flow-enabling features. In the illustrated embodiment, the open, external flow-enabling features are one or more ribs 4703b, or alternatively grooves/channels, which run substantially the entire axial length of the main body 4702b of the IOP sensor implant housing. The ribs 4703 can be in contact with eye tissue and aqueous can flow along the grooves/channels. Again, when the housing 4702b is surgically implanted in, for example, a physiological outflow pathway of the eye, one end of each flow-enabling feature 4703b can be located in the anterior chamber, while the opposite end of each flow-enabling feature can be located in the physiological outflow pathway. In this way, drainage can be enhanced.

In some embodiments, external flow-enabling features can be made out of or include a porous material, such as fritted glass, porous plastic such as polypropylene, polyethylene, etc., porous bonded polymer fibers such as polyethylene, polyester, etc. or other materials that are preferably hydrophilic and can be formed into an open-cell porous structure. Such porous materials provide a plurality of fluid handling capillary or pseudo-capillary structures that enable fluid transfer through the bulk structure of the material itself. For example, the porous material may be provided on substantially the entire exterior surface of the housing, in axial ribs or strips on the housing, in grooves/channels formed on the outside of the housing (e.g., between the ribs 4703b shown in FIG. 47C), etc.

Intraocular Pressure Sensing Implant with Anchoring Tacks

Figure 48A:
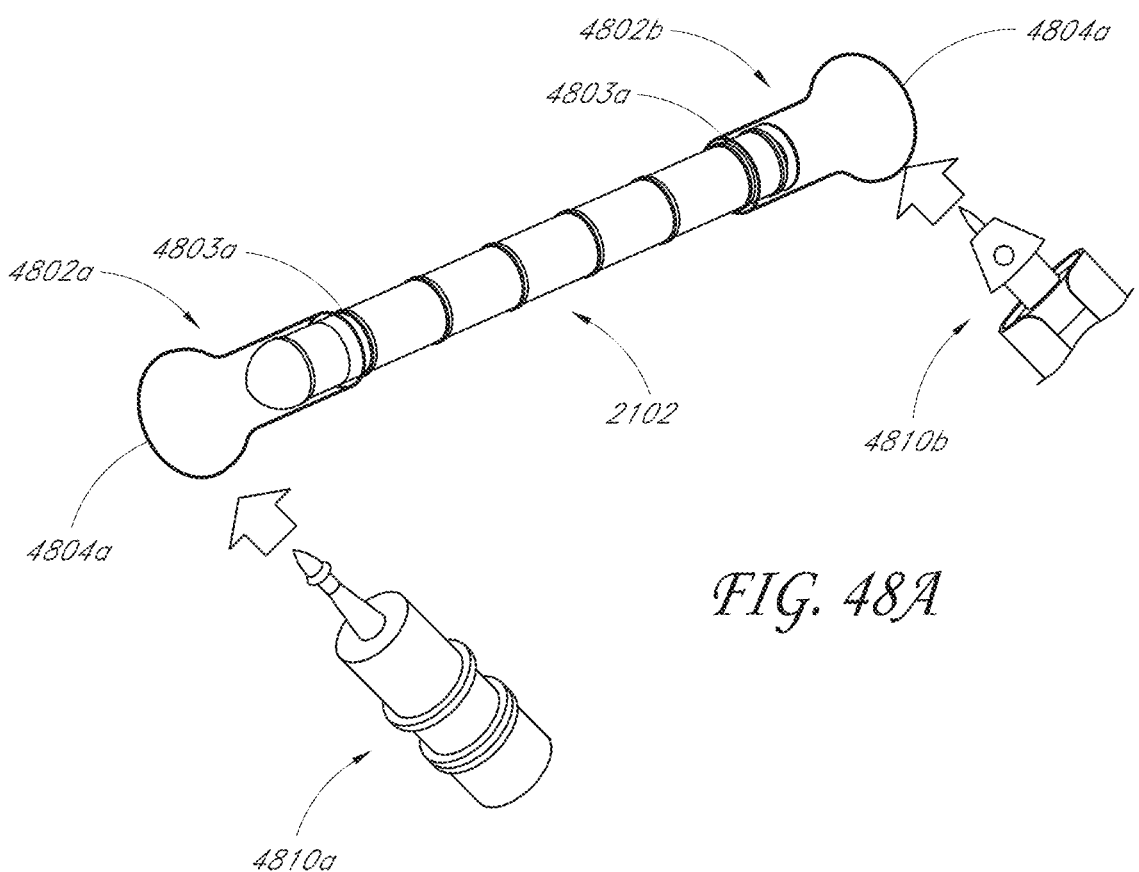
FIG. 48A illustrates an example embodiment of an anchoring system for attaching an intraocular implant to eye tissue.
Figure 48B:
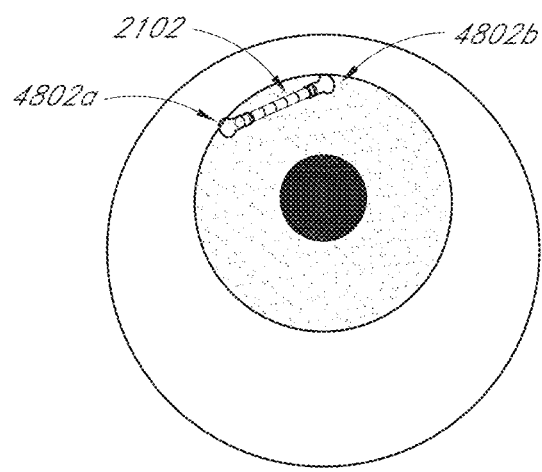
FIG. 48B illustrates an intraocular implant anchored inside the eye using the anchoring system shown in FIG. 48A.

FIGS. 48A and 48B illustrate an example embodiment of an anchoring system for attaching an intraocular implant to eye tissue. This anchoring system can be used to attach IOP sensing implants like those described herein (e.g., IOP sensing implant 2102) to tissue and/or anatomical structures inside the eye (e.g., in the anterior chamber). The anchoring system may include one, two, or more anchoring tethers 4802. As shown in the figures, a first portion of each anchoring tether can be designed to attach to the intraocular implant that is to be anchored down, while a second portion of each anchoring tether can be designed to attach to an anchoring tack which is inserted into eye tissue. The anchoring tacks can be functional beyond simply serving as anchors in ocular tissue. For example, the anchoring tacks can also be implant devices which perform one or more functions which are complementary to, and/or in addition to, the function(s) performed by the intraocular implant that is being anchored to the eye tissue by the anchoring tacks.

In the embodiment illustrated in FIG. 48A, the anchoring system includes a first anchoring tether 4802a located at the tip end of the IOP sensing implant 2102 and a second anchoring tether 4802b located at the sensor end, though other embodiments could include a different number of anchoring tethers. It should be understood that while IOP sensing implant 2102 is shown in these figures, the illustrated anchoring tethers 4802 can be used on other designs of an IOP sensing implant and other types of implants as well. The anchoring tethers 4802 can be made of, for example, flexible wires or cords. Nitinol is a possible material due to its super-elasticity and biocompatibility. Also, thin wires or other loop structures made of titanium, gold, or stainless steel are also possible. Non-metallic cords made of nylon, polyester, polyvinylidene fluoride, polypropylene, etc. may also be used in some embodiments.

Each anchoring tether 4802 can be attached to the IOP sensing implant 2102. This can be done by, for example, providing an attachment loop portion 4803 which wraps around the housing of the IOP sensing implant. The housing of the IOP sensing implant may in turn include one or more circumferential ridges, flanges, or troughs, and/or one or more hooks, eyelets, etc. so as to help position the attachment loop portions 4803 and/or hold the attachment loop portions in place with respect to the IOP sensing implant housing. As illustrated in FIG. 48A, in some embodiments the attachment loop portion 4803 of each anchoring tether can azimuthally wrap around the circumference of the implant body in a plane that is perpendicular to the axis of the implant body. The anchoring tethers 4802 can also each include an anchor loop portion 4804 which extends from the attachment loop portion 4803 at one or more connection points to form a loop which can receive an anchoring tack. In some embodiments the anchoring loop portion 4804 of each anchoring tether 4802 can extend from the attachment loop portion 4803 in a plane that is parallel with the axis of the implant body. In other words, the attachment loop portion 4003 and the anchoring loop portion 4804 of each anchoring tether 4002 can be oriented generally in planes that are orthogonal to one another. In other embodiments, an anchoring tether could be attached to the implant in different ways, such as by welding or brazing the tether to the housing, by use of adhesives such as epoxy, or by providing an eyelet or similar structure in the housing through which the anchoring tether can loop through, for example.

FIG. 48A illustrates two example embodiments of anchoring tacks 4810a, 4810b. The first example anchoring tack 4810a is a drug eluting intraocular implant. This implant can be similar to, for example, the one illustrated in FIG. 18 of U.S. Patent Publication 2015/0342875 (see accompanying appendix), filed May 28, 2015, and entitled "IMPLANTS WITH CONTROLLED DRUG DELIVERY FEATURES AND METHODS OF USING SAME," the entire contents of which are hereby incorporated by reference herein. The second example anchoring tack 4810*b* is a drainage stent which enhances outflow of aqueous humor from the eye. This implant can be similar to, for example, the one illustrated in FIG. 18 of U.S. Pat. No. 9,554,940 (see accompanying appendix), filed Mar. 14, 2013, and entitled "SYSTEM AND METHOD FOR DELIVERING MULTIPLE OCULAR IMPLANTS," the entire contents of which are hereby incorporated by reference herein.

Each of the anchoring tacks 4810*a*, 4810*b* can include a penetrating tip which is designed to penetrate ocular tissue, such as the sclera, the trabecular meshwork, etc., and remain anchored therein after having been inserted. The penetrating tip of each anchoring tack 4810 can be inserted through the respective anchoring loop portion 4804 of the anchoring tethers 4802, as illustrated by the arrows in FIG. 48A. The body portions of the anchoring tacks 4810 can include one or more structural features designed such that the anchoring loop portions 4804 of the anchoring tethers 4802 are firmly retained once the tacks are inserted through the anchoring loop portions 4804. For example, the body portions of the anchoring tacks 4810 can include one or more features (e.g., ridges, projections, flanges, etc.) which prevent the anchoring loop portions 4804 of the anchoring tethers 4802 from passing over the anchoring tacks once the anchoring tacks are inserted through the loops. For example, the feature(s) on the body portion of an anchoring tack 4810 can have at least one dimension that is larger than the diameter of the anchoring loop portion 4804. Thus, the anchoring loop portions 4804 of the anchoring tacks 4810 can be firmly held between ocular tissue and the body portions of the anchoring tacks 4810.

FIG. 48B illustrates an intraocular implant anchored inside the eye using the anchoring system shown in FIG. 48A. Although FIG. 48B illustrates one example placement of the IOP sensing implant 2102 using the anchoring tethers 4802, the illustrated anchoring system can also be used to attach various types of intraocular implants to various other locations within the eye.

Sealed Battery with Through-Substrate Via Interconnects

Figure 49A:
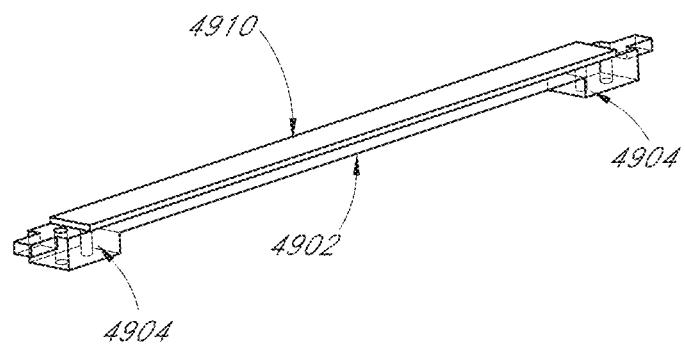
FIG. 49A illustrates a sealed thin-film battery mounted on a substrate and electrically connected to other components by through-substrate vias.

FIG. 49A illustrates a sealed thin-film battery 4910 mounted on a substrate 4902 and electrically connected to other components by through-substrate vias 4904. The sealed thin-film battery 4910 may be, for example, a thin-film lithium-ion battery. Thin-film lithium-ion batteries can be advantageous because of their relatively high power density. But they can include very reactive materials and therefore should be well-sealed in order to provide a long-lasting useful lifetime.

In some embodiments, the substrate 4902 upon which the thin-film battery 4910 is mounted is the carrier member 572 described elsewhere herein. As such, the substrate 4902 may be provided in an IOP sensing implant, as described herein. The battery 4910 may be electrically connected to other electrical components of an IOP sensing implant (e.g., controller, memory, IOP sensing module, etc.) by way of the through-substrate vias 4904. In some embodiments, the substrate 4902 is made of glass, though it can also be made at least partially of other electrically insulating materials.

The through-substrate vias 4904 are formed in the substrate 4902 on the side of the substrate upon which the battery 4910 is mounted. The vias 4904 include conductive structures or terminals (e.g., posts) which are oriented perpendicularly with respect to the bottom surface of the battery 4910 and are used to make electrical connections to the battery. The battery 4910 can be mounted, or fabricated in situ, flush with the surface of the substrate 4902 over the vias 4904. As discussed further herein, this advantageously allows the physical interface between the battery 4910 and the substrate to be completely sealed. In some embodiments, the vias 4904 span the entire thickness of the substrate 4902. In such embodiments, the vias 404 may allow the battery 4910 to be electrically connected with one or more conductive traces which are formed on the opposite side of the substrate from which the battery 4910 is mounted. In other embodiments, the vias 4904 may only partially span the thickness of the substrate. In such embodiments, the vias 4904 may allow the battery 4910 to be electrically connected with one or more conductive traces which are embedded in the substrate.

Figure 49B:
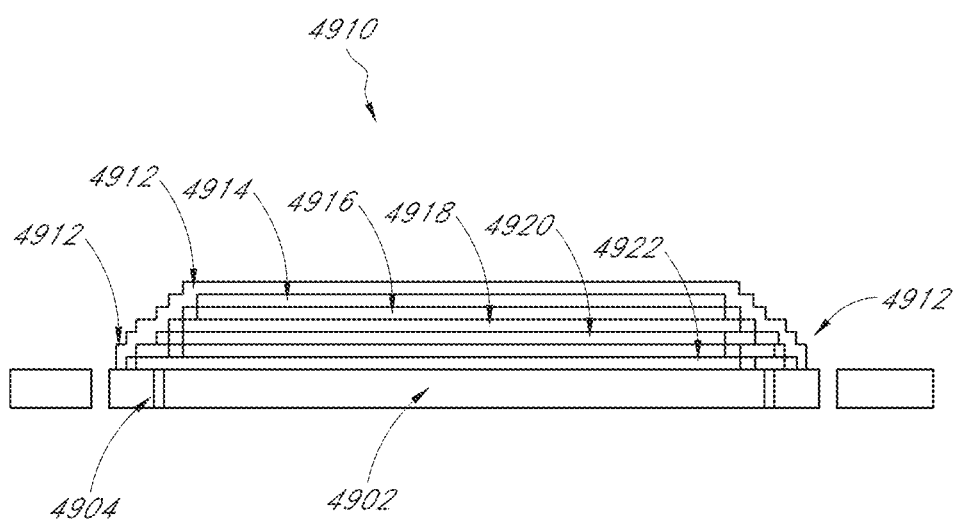
FIG. 49B is a schematic cross-sectional view of an embodiment of the sealed thin-film lithium-ion battery mounted on the substrate.

FIG. 49B is a schematic cross-sectional view of an embodiment of the sealed thin-film lithium-ion battery 4910 mounted on the substrate 4902. The thin-film battery 4910 can be made up of several electrically-active layers 4916, 4918, 4920, and 4922. For example, the thin-film battery 4910 can include a cathode current collector layer, a cathode layer, an electrolyte layer, and an anode current collector layer, depicted as layers 4922, 4920, 4918, and 4916, respectively, in FIG. 49B. As shown in the drawing, the electrically-active layers may have somewhat different sizes, such that the peripheral edges of one layer may extend out from beyond another layer when they are provided in a stacked configuration. In other embodiments of thin-film batteries, different layers and/or layer configurations may be utilized beyond the ones illustrated in FIG. 49B. For example, an anode layer may be included between the electrolyte layer and the anode current collector. In some embodiments, the anode layer is created during fabrication of the thin-film battery, while in other embodiments the anode layer is formed during the first instance of charging the battery. In some embodiments, the anode is Lithium metal. In a "Li-free" design, the anode can be plated onto the anode current collector during the charging of the battery. During discharge, the Li metal can be de-plated. After the first charge of the battery some Li metal may remain on the anode current collector even after battery discharge. In other embodiments, the Li anode can be deposited as part of the battery fabrication process and may be present even before first charge.

The battery 4910 can be fabricated on the substrate itself (in situ). It can be produced in a batch process in a wafer format. The substrate can be made from the wafer material by cutting/releasing the individual substrates from the wafer after battery fabrication is complete.

The electrically-conductive terminals of the thin-film battery 4910 are located at the bottom layer of the stack of electrically-active layers 4916, 4918, 4920, and 4922. These terminals make electrical connection to the through-substrate vias 4904 that are formed in the substrate 4902 upon which the thin-film battery 4910 is mounted (or fabricated in situ). In this way, the stack of electrically-active layers of the thin-film battery 4910 can be flush with the mounting surface of the substrate 4902.

FIG. 49B also illustrates an insulating layer 4914 which is formed over the stack of electrically-active layers 4916, 4918, 4920, and 4922. As shown in the drawing, the insulating layer 4914 can be formed not only over the surface of the top layer of the stack of electrically-active layers 4916, 4918, 4920, and 4922, but also over any portions of the layers in the stack which may extend beyond the layers above. The insulating layer may extend to the mounting surface of the substrate 4902 around the entire perimeter of the battery 4910. The insulating layer 4914 can be made of, for example, any suitable electrically-insulating material, such as a polymer.

Additionally, FIG. 49B shows a sealing layer 4912 which is formed over the insulating layer 4914. In some embodiments, the sealing layer is an impermeable metal barrier layer which prevents atoms or molecules outside the battery 4910 from interacting with atoms or molecules inside the battery, and vice versa. The sealing layer may extend to the mounting surface of the substrate 4902 around the entire perimeter of the battery 4910, including the perimeter of the insulating layer 4914. Since the through-substrate via interconnects allow the thin-film battery 4910 to sit flush on the surface of the substrate 4902, the sealing layer 4912 can be provided or formed without gaps between the substrate 4902 and the sealing layer 4912. Thus, the illustrated battery architecture offers improved sealing performance which in turn improves the useful lifetime of the battery 4910 without requiring more complex sealing structures or techniques, specifically by not requiring lateral feedthroughs or interconnects that must transit the sealing layer 4912.

Figure 49C:
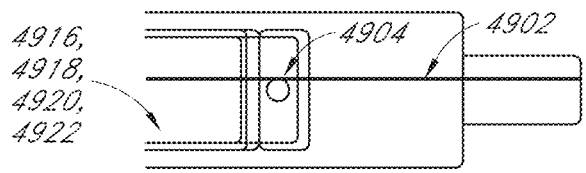
FIGS. 49C-49E are top views which further illustrate the architecture of the thin-film battery shown in FIGS. 49A and 49B.
Figure 49D:
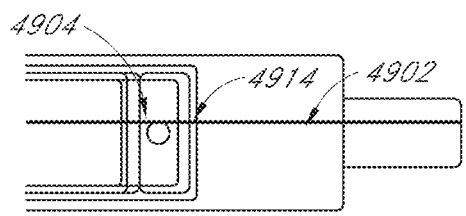
Figure 49E:
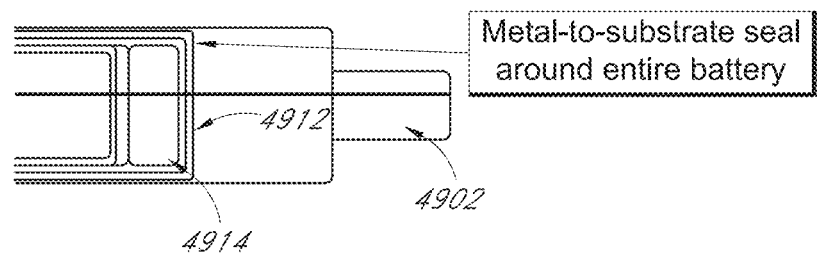

FIGS. 49C-49E are top views which further illustrate the architecture of the thin-film battery 4910. FIG. 49C is a top view of the stack of electrically-active layers 4916, 4918, 4920, 4922 of the thin-film battery 4910. As illustrated, the stack of electrically-active layers is provided on the substrate 4902 and a through-substrate via 4904 (shown in phantom line) is provided under the stack. FIG. 49D shows the insulating layer 4914 provided over the stack of electrically-active layers 4916, 4918, 4920, 4922. As illustrated, the insulating layer 4914 extends all the way to the substrate 4902, both in its lateral and longitudinal extent. FIG. 49E shows the metal sealing layer 4912 provided over the insulating layer 4914. The insulating layer 4914 serves to separate the metal sealing layer 4912 from the electrically-active layers 4916, 4918, 4920, 4922. As illustrated in FIG. 49E, the metal sealing layer 4912 extends all the way to the substrate 4902, both in its lateral and longitudinal extent, completely covering the insulating layer 4914 and leaving no gaps between the sealing layer 4912 and of the substrate 4902. The fact that there are no electrical interconnect structures which extend laterally outward from the battery 4910 on or over the mounting surface of the substrate 4902 means that the quality of the seal between the sealing layer 4912 and the substrate 4902 is enhanced. This is in contrast to the configuration shown in FIG. 49F.

Figure 49F:
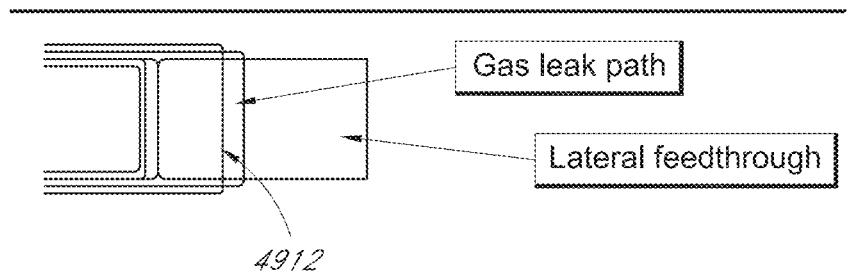
FIG. 49F illustrates a thin-film battery architecture which includes a lateral electrical interconnect rather than a through-substrate via electrical interconnect.

FIG. 49F illustrates a thin-film battery architecture which includes a lateral electrical interconnect rather than a through-substrate via electrical interconnect. As illustrated, the lateral electrical interconnect extends laterally from the battery on the mounting side of the substrate. As a result of the lateral electrical interconnect, the battery shown in FIG. 49F is likely to have a less effective seal between the sealing layer 4912 and the substrate 4902. This is because the sealing layer 4912 can extend completely down to the substrate on the sides of the lateral electrical interconnect but then must rise over the top of the lateral electrical interconnect, which extends from the battery underneath the sealing layer 4912. This can result in the formation of a gas diffusion pathway through the insulating layer 4914 between the sealing layer 4912 and the substrate, which in turn can allow materials inside the battery to react with gases and water vapor entering the battery structure from the outside environment, therefore reducing the useful lifetime of the battery.

Stacked IC and Battery Structure

Figure 50:
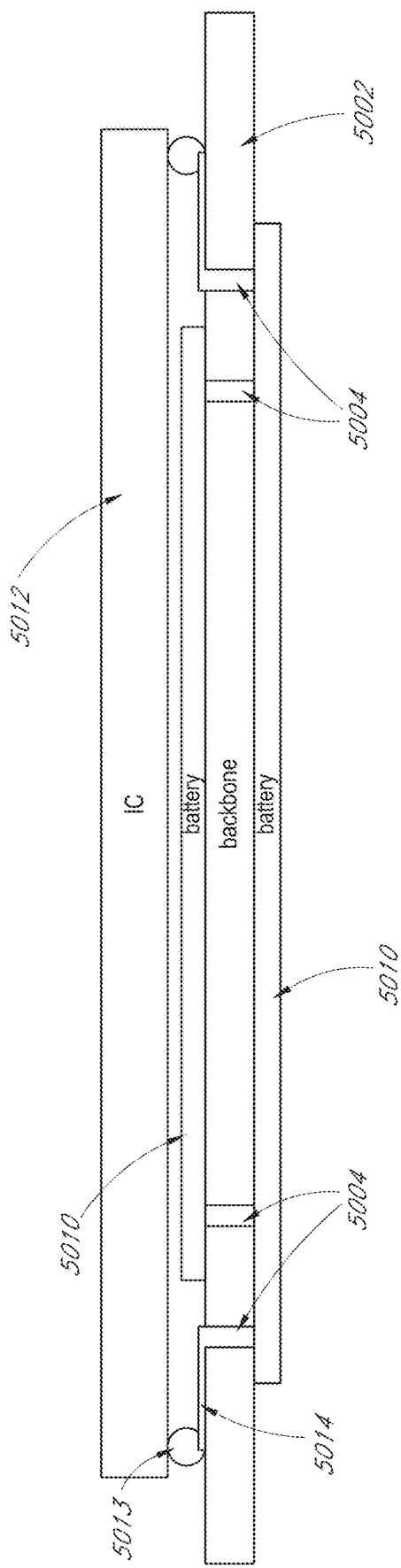
FIG. 50 illustrates a compact stacked integrated circuit and battery structure for an intraocular implant.

FIG. 50 illustrates a compact stacked integrated circuit and battery structure for an intraocular implant. This compact structure is advantageous because intraocular implants, such as IOP sensing implants, are typically quite small in size and therefore space inside the implant is limited. The illustrated stacked structure includes a substrate 5002, which, in some embodiments, is the carrier member 572 described elsewhere herein. As such, the substrate 5002 may be provided in an IOP sensing implant, as described herein. A first battery 5010 is mounted to the top of the substrate 5002 and a second battery 5010 is mounted to the bottom of the substrate. The batteries 5010 may be mounted to the substrate 5002 by way of through-substrate vias 5004, as described with respect to FIGS. 49A and 49B. In some embodiments, the first and second batteries each have a thickness of less than 50 μm. For example, the first and second batteries may each have a thickness of approximately 30μ or less.

A first integrated circuit 5012 is mounted to the top surface of the substrate 5002 over, and spanning, the first battery 5010 which is likewise mounted on the top surface of the substrate. Although not illustrated, the structure could also include a second integrated circuit mounted to the bottom surface of the substrate 5002 over, and spanning, the second battery 5010. The first integrated circuit 5012 is electrically connected to one or more conductive traces 5014 on the substrate 5002 by way of one or more solder bumps 5013. The solder bumps have at least one dimension (e.g. a height) which is greater than the thickness of the battery 5010 over which the integrated circuit is mounted. For example, in some embodiments, the solder bumps have a height of 50 μm or more. The lateral dimensions of the integrated circuit are greater than those of the battery 5010 over which the integrated circuit is mounted. Thus, the integrated circuit 5012 can span the battery 5010 and can be supported by solder bumps 5013 located around the periphery of the integrated circuit beyond the lateral extent of the battery 5010. Since the height of the solder bumps 5013 can be greater than the thickness of the battery 5010, the battery can occupy the space underneath the integrated circuit which otherwise would not have been occupied by any component and would instead have been wasted. In other embodiments, the solder bumps can be replaced by stud bumps, such as gold stud bumps. Stud bumps may be used in conjunction with conductive epoxy to perform the same function as the solder bumps, but they can be smaller and can be processed at lower temperatures.

Although a battery 5010 is illustrated as being mounted on the substrate 5002 below the integrated circuit 5012, in other embodiments some other electrical component could be mounted under the integrated circuit. However, this mounting location is particularly suited for a thin-film battery due to its relatively small thickness in comparison to the size of the solder bumps 5013 which are used to connect the integrated circuit to the substrate 5002. Similarly, although an integrated circuit 5012 is illustrated as being connected and mounted by one or more solder bumps, in other embodiments some other electrical component could be mounted over the battery 5010 using solder bumps, such as an additional battery.

Antenna for Intraocular Implant

Various embodiments of the intraocular implants described herein can include a transceiver module (and/or other wireless interface) and an antenna for wirelessly communicating with one or more external devices. The antenna can also be used for receiving power from an external device via inductive coupling. Any antenna that is used will have a natural or self-resonant frequency which is dependent upon the associated inductance and capacitance of the antenna design. The natural or self-resonant frequency is the frequency of electromagnetic radiation to which the antenna is most sensitive. Therefore, it is advantageous that there be a relative match between the self-resonant frequency of the antenna and the operating frequency of the transceiver module or other wireless interface used by the intraocular implant.

FIG. 24 illustrates an example coil antenna 2085 which consists of loops of wire which spiral around the internal components of the intraocular implant as the coil antenna extends along the longitudinal axis of the implant housing. It is not unusual that this type of antenna design may have a self-resonant frequency of several hundred megahertz or that it even extend into the gigahertz range. These frequencies are typically much higher than the operating frequency of the transceiver module or other wireless interface used by the intraocular implant. Accordingly, it may be necessary to use additional circuit elements, such as a capacitor and/or an inductor, to tune the antenna so that it is more sensitive to the operating frequency of the transceiver module or other wireless interface. One disadvantage associated with this approach is that such circuit elements may occupy valuable space within the intraocular implant. If the antenna could be tuned in another manner without requiring the use of additional circuit elements, or if the antenna could be designed such that its self-resonant frequency naturally corresponded to the operating frequency of the transceiver module or other wireless interface, then the size of the intraocular implant could advantageously be reduced.

Figure 51A:
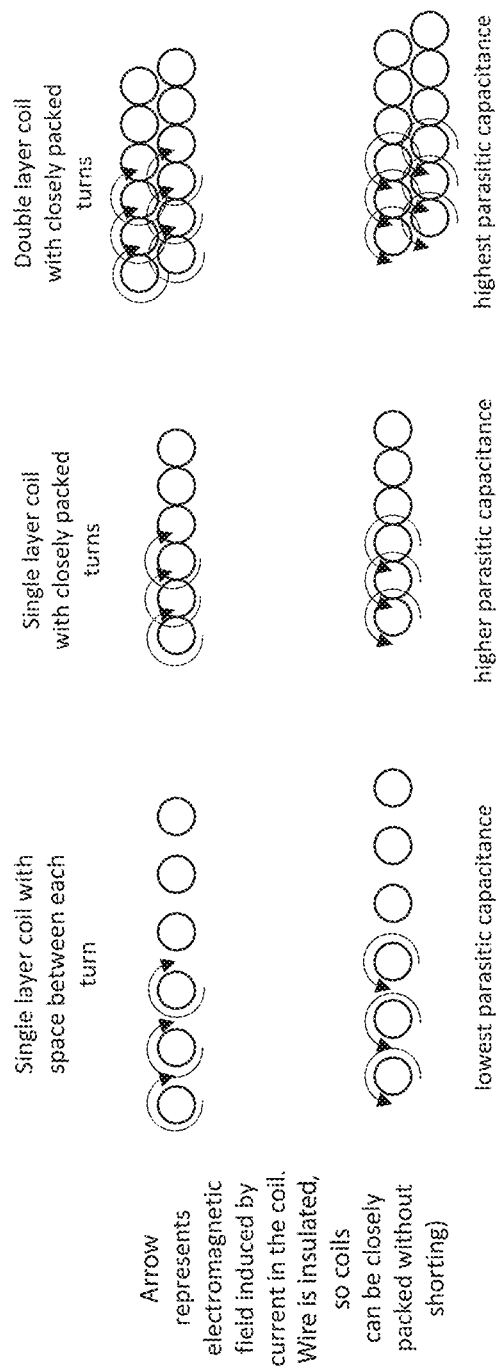
FIG. 51A schematically illustrates cross-sectional views of three example coil antennas which may be used in an intraocular implant.
Figure 51B:
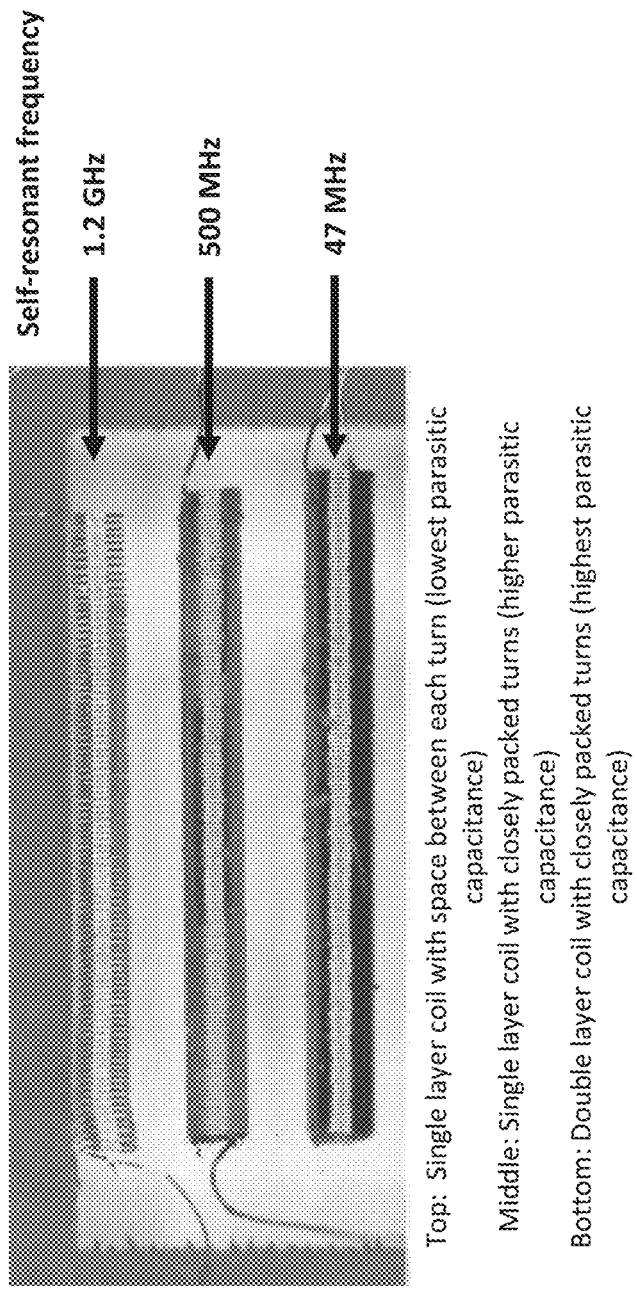
FIG. 51B is a photograph of example embodiments of the three coil antenna designs shown in FIG. 51A.

FIG. 51A schematically illustrates cross-sectional views of three example coil antennas which may be used in an intraocular implant. The black dots represent cross-sections of coils of wire. Meanwhile, the arrows represent the magnetic field induced by the current flowing through the coils of wire. FIG. 51B is a photograph of example embodiments of the three coil antenna designs shown in FIG. 51A. The left-hand, middle, and right-hand coil antennas in FIG. 51A respectively correspond to the top, middle, and bottom coil antennas in FIG. 51B.

The coil antenna design on the left in FIG. 51A is one in which the wire turns are spaced apart from one another along the longitudinal axis of the coil antenna. In addition, in the left-hand coil antenna design, there is only one layer (in the radial direction) of wire turns. The loops formed by the turns of wire result in an amount of inductance which impacts the self-resonant frequency of the antenna. In addition, the proximity of the turns of wire, as determined by the spacing between adjacent turns, results in some amount of parasitic capacitance which also impacts the self-resonant frequency of the antenna. As shown in FIG. 51B, this coil antenna design may typically have a self-resonant frequency of about 1.2 GHz.

The coil antenna design in the middle of FIG. 51A is similar to the left-hand coil design except that the turns of wire are touching one another in the middle coil antenna design. The wire is tightly wrapped along the longitudinal axis of the coil antenna such that each turn of wire is in contact with the adjacent turn of wire in the longitudinal direction. (The wire may be coated with a thin insulator to allow the turns of wire to be in contact with one another without shorting out the coil.) The middle coil antenna design has certain advantages over the left-hand coil antenna design. These advantages include that a greater number of turns of wire can fit into a given longitudinal space because they are not spaced apart from one another. This can increase the self-inductance of the antenna and improve the inductive coupling performance of the coil antenna for purposes of, for example, wireless power transfer. In addition, the lack of separation between adjacent turns of wire increases the parasitic capacitance of the coil antenna. The increased parasitic capacitance and the increased self-inductance lower the self-resonant frequency of this coil antenna design. For example, as shown in FIG. 51B, this coil antenna design may typically have a self-resonant frequency of about 500 MHz. This reduction in self-resonant frequency, as compared to the coil antenna with spaced apart wire turns, is advantageous because it can be tuned to the operating frequency of the transceiver module or other wireless interface using smaller capacitor and/or inductor circuit elements.

The coil antenna design on the right-hand side in FIG. 51A is distinct from the middle coil antenna design in that it includes two (or more) layers of wire turns (in the radial direction). As indicated by the blue arrows, the wire turns are wrapped such that the electrical current through the first and second layers of wire turns flows in the same direction. As illustrated, in this design each turn of wire is now not only in contact with the adjacent turn in the longitudinal direction but it is also in contact with one or more adjacent turns in the radial direction. The close proximity of each turn of wire to multiple other turns of wire greatly increases the parasitic capacitance of the right-hand coil antenna design. This in turn greatly reduces the self-resonant frequency of the coil antenna. For example, as shown in FIG. 51B, this coil antenna design may typically have a self-resonant frequency of about 47 MHz. Although the coil antenna design shown on the right-hand side of FIG. 51A takes up more space in the radial direction because it has multiple layers of wire turns, which correspondingly either reduces the amount of space available for other components to be housed inside the coil or requires an increase in the size of the housing of the intraocular implant, it turns out that any drawbacks associated with this increase in the radial thickness of the coil antenna is more than compensated by the reduction in the self-resonant frequency of the antenna. The reduction in the self-resonant frequency means that the capacitor and/or inductor circuit elements which may otherwise be required so as to tune the antenna to the operating frequency of the transceiver module and/or other wireless interface can be reduced in size or even completely eliminated. The coil antenna design shown on the right-hand side of FIG. 51A also has an additional advantage which is illustrated in FIG. 51C.

Figure 51C:
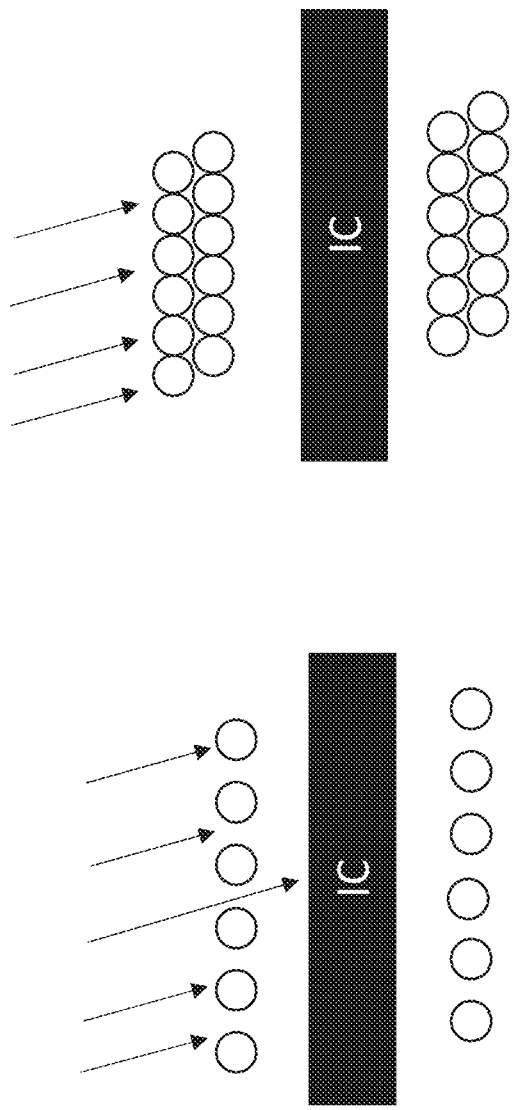
FIG. 51C illustrates the electromagnetic shielding effect offered by the two-layer coil antenna design shown in FIG. 51A.

FIG. 51C illustrates the electromagnetic shielding effect offered by the two-layer coil antenna design shown in FIG. 51A. As already discussed previously herein, a carrier member with one or more electrical components can be provided in the open space in the interior of the coil antenna. The left-hand side of FIG. 51C shows an integrated circuit component provided in the interior space of a coil antenna with a single layer of spaced apart wire turns (i.e., as in the left-hand side of FIG. 51A). Rays of electromagnetic radiation (e.g., background electromagnetic radiation in the environment) are incident upon the transverse side of the coil antenna. The electromagnetic radiation can penetrate the coil antenna due to the spacing between the coil turns. This electromagnetic radiation can then be incident upon the integrated circuit, causing electromagnetic interference which may be detrimental to the operation of the integrated circuit, particularly if low-power subthreshold transistors are used. In contrast, as shown on the right-hand side of FIG. 51C, the coil antenna with two or more layers of wire turns which are tightly wrapped, and touching one another, in the longitudinal direction is much more effective at shielding the interior integrated circuit from electromagnetic radiation.

Antenna for Intraocular Implant Having Bi-Diameter Main Housing

Figure 52A:
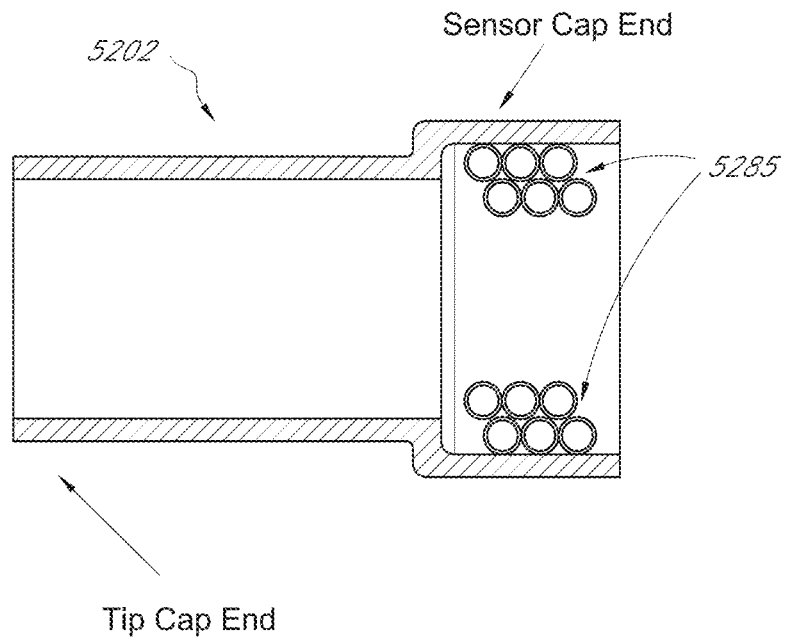
FIG. 52A illustrates the location of an antenna inside an embodiment of an intraocular implant with a bi-diameter main housing.

FIG. 52A illustrates the location of an antenna 5285 inside an embodiment of an intraocular implant with a bi-diameter main housing 5202. The bi-diameter main housing 5202 of the intraocular implant is described herein with respect to FIG. 42A. It has a first, larger diameter at the sensor cap end of the bi-diameter main housing 5202 and a second, smaller diameter at the tip cap end. As shown in FIG. 52A, a coil antenna 5285, such as the one illustrated on the right-hand side of FIG. 51A, can be provided at least partially in the sensor cap end of the bi-diameter main housing. This arrangement has multiple advantages. First, the diameter of the coil antenna can be made larger than if the antenna were provided in the smaller-diameter portion of the bi-diameter main housing. This increases the amount of electromagnetic flux which can pass through the coil during inductive power transfer from external device. Another advantage is illustrated in FIG. 52B.

Figure 52B:
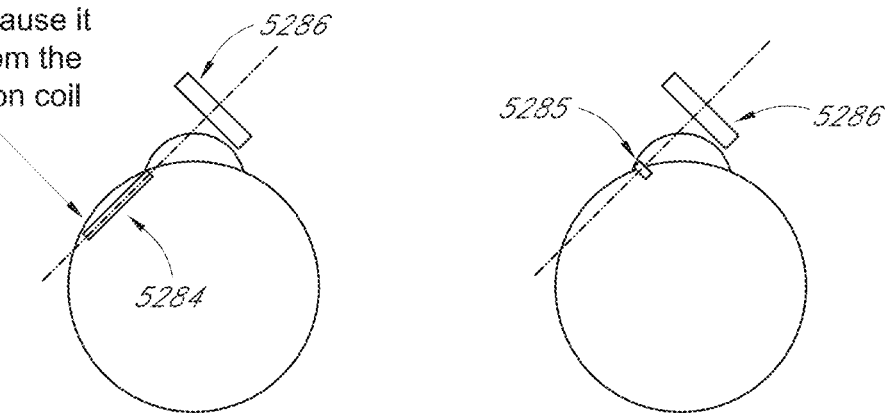
FIG. 52B shows the intraocular implant of FIG. 52A implanted in the eye of a patient.

FIG. 52B shows the intraocular implant of FIG. 52A implanted in the eye of a patient. In this embodiment, the intraocular implant is anchored in, for example, the suprachoroidal/superciliary space of the patient's eye. The left-hand side of FIG. 52B shows a coil antenna 5284 that is narrower and longer than the coil antenna 5285 shown in FIG. 52A due to its being provided in the smaller-diameter portion of the bi-diameter housing 5202. The charging coil 5286 of an external power device is also illustrated. The charging coil 5286 of the external power device is brought in proximity to the patient's eye so as to inductively couple with the coil antenna 5284. The distal end of the coil antenna 5284 contributes less to the inductive power transfer than does the proximal end because it is located further away from the charging coil 5286 of the external power device. Thus, it would be advantageous if a greater portion of the coil antenna inside the intraocular implant could be positioned nearer the charging coil of the external device when the implant is installed at the desired location within the eye. As shown in the right-hand side of FIG. 52B, this aim is achieved by the configuration shown in FIG. 52A. When the coil antenna 5285 is provided in the larger-diameter sensor cap end of the intraocular implant, a larger percentage of the coil is located nearer the charging coil 5286 of the external power device when the intraocular implant is installed at the desired location within the patient's eye. This improves inductive coupling between the antenna 5285 and the charging coil 5286, thus improving wireless power transfer to the intraocular implant.

IOP Sensing System Devices

FIG. 53 is a table which describes several devices and systems which can be used in conjunction with the intraocular implants described herein. A physician diagnostic device can be used by a physician to download data (e.g., IOP measurements), wirelessly re-charge a patient's IOP sensing implant, perform implant system diagnostics, re-program the implant, etc. The physician diagnostic device may take the form of a pair of glasses, a soft mask, etc.

An atmospheric pressure monitor device may be a patient-worn device which measures and records local atmospheric pressure readings which can be used together with readings from the implant to determine IOP gauge pressure values. This device may take the form of a wrist band, watch, pendant, smartphone application, etc.

A patient device can be used to download absolute IOP measurements from the implant, re-sync timers and/or re-charge super capacitor power sources on the implant. The device can include a screen or other output device to provide information (IOP readouts, battery life, etc.) and reminders (to re-sync timers, re-charge super capacitors, etc.). This device can be combined with the atmospheric pressure monitor device in some embodiments.

A patient at-home recharge device can be worn by the patient for minutes or hours to recharge the intraocular implant's battery and/or supercapacitor, and/or to download data from the implant. This device may also allow increased functionality from the IOP sensing implant, such as taking and transmitting continuous IOP readings, that may otherwise consume too much power to perform when the IOP sensing implant is operating under battery power alone. This device may take the form of a pair of glasses, soft mask, etc.

An at-home link-box can connect to other patient devices, such as those described above, to transfer data collected by them to a central server. It can also include a re-charging station to re-charge the external devices.

A central server can be provided to receive patient data from multiple patients via the internet. The central server can process raw data to provide processed, adjusted, and/or corrected measurements. The central server can also provide a web-based interface for patients and physicians to view and/or download data.

The foregoing devices may each communicate with one another via network connectivity, such as a wired or wireless network interface.

Example Embodiments

In some embodiments, an intraocular pressure (IOP) sensing system may comprise: an intraocular pressure sensing implant to be implanted into the eye of a patient for capturing absolute intraocular pressure measurements; and an external device for capturing atmospheric pressure measurements, wherein the intraocular pressure sensing implant is configured to capture an absolute intraocular pressure measurement at an appointed time, and wherein the external device is configured to capture a plurality of atmospheric pressure measurements around the appointed time.

In any of the preceding embodiments, the intraocular pressure sensing implant may include a first onboard timekeeping device, and the absolute intraocular pressure sensing implant may be configured to capture the intraocular pressure measurement at the appointed time, as indicated by the first onboard timekeeping device.

In any of the preceding embodiments, the external device may include a second timekeeping device, and the external device may be configured to capture the plurality of atmospheric pressure measurements around the appointed time, as indicated by the second timekeeping device.

In any of the preceding embodiments, the external device may be configured to capture the plurality of atmospheric pressure measurements during a window of time which extends before and after the appointed time.

In any of the preceding embodiments, the IOP sensing system may further comprise a processing device configured to analyze the plurality of atmospheric pressure measurements to determine a measure of the variation between the plurality of atmospheric pressure measurements.

In any of the preceding embodiments, the processing device may be configured to determine whether the variation is within a predetermined range.

In any of the preceding embodiments, the processing device may be configured to correlate one or more of the plurality of atmospheric pressure measurements with an absolute intraocular pressure measurement if the variation is within the predetermined range.

In any of the preceding embodiments, the processing device may be configured to calculate a gauge intraocular pressure measurement from the correlated atmospheric pressure and absolute intraocular pressure measurements.

In any of the preceding embodiments, the processing device may be separate from the external device.

In any of the preceding embodiments, the external device may be configured to execute a synchronization operation by wirelessly transmitting synchronization information to the intraocular pressure sensing implant to aid in correlating one or more atmospheric pressure measurements with one or more absolute intraocular pressure measurements.

In any of the preceding embodiments, the synchronization information may comprise a unique identification value or a timestamp.

In any of the preceding embodiments, the external device may initiate the synchronization operation automatically at a predetermined time or interval.

In any of the preceding embodiments, the external device may be configured to prompt the patient to initiate the synchronization operation.

In any of the preceding embodiments, the prompt may comprise an audible alarm.

In any of the preceding embodiments, initiating the synchronization operation may comprise positioning the external device within 12 inches of the patient's eye.

In any of the preceding embodiments, the synchronization operation may comprise synchronizing a first timekeeping device onboard the intraocular pressure sensing implant with a second timekeeping device onboard the external device.

In any of the preceding embodiments, the external device may be configured to be worn by the patient.

In some embodiments, an intraocular pressure (IOP) sensing method may comprise: receiving an absolute intraocular pressure measurement from an intraocular pressure sensing implant implanted in the eye of a patient, the absolute intraocular pressure measurement having been captured at an appointed time; and receiving a plurality of atmospheric pressure measurements from an external device outside of the eye, the plurality of atmospheric pressure measurement having been captured around the appointed time.

In any of the preceding embodiments, the absolute intraocular pressure measurement may be captured at the appointed time, as indicated by a first onboard timekeeping device included with the intraocular pressure sensing implant.

In any of the preceding embodiments, the plurality of atmospheric pressure measurements may be captured around the appointed time, as indicated by a second timekeeping device included with the external device.

In any of the preceding embodiments, the plurality of atmospheric pressure measurements may be captured during a window of time which extends before and after the appointed time.

In any of the preceding embodiments, the IOP sensing method may further comprise analyzing the plurality of atmospheric pressure measurements to determine a measure of the variation between the plurality of atmospheric pressure measurements.

In any of the preceding embodiments, the IOP sensing method may further comprise determining whether the variation is within a predetermined range.

In any of the preceding embodiments, the IOP sensing method may further comprise correlating one or more of the plurality of atmospheric pressure measurements with the absolute intraocular pressure measurement if the variation is within the predetermined range.

In any of the preceding embodiments, the IOP sensing method may further comprise calculating a gauge intraocular pressure measurement from the correlated atmospheric pressure and absolute intraocular pressure measurements.

In any of the preceding embodiments, the IOP sensing method may further comprise analyzing the plurality of atmospheric pressure measurements using a processing device that is separate from the external device.

In any of the preceding embodiments, the IOP sensing method may further comprise executing a synchronization operation by wirelessly transmitting synchronization information to the intraocular pressure sensing implant to aid in correlating one or more atmospheric pressure measurements with the absolute intraocular pressure measurement.

In any of the preceding embodiments, the synchronization information may comprises a unique identification value or a timestamp.

In any of the preceding embodiments, the IOP sensing method may further comprise initiating the synchronization operation automatically at a predetermined time or interval.

In any of the preceding embodiments, the IOP sensing method may further comprise prompting the patient to initiate the synchronization operation.

In any of the preceding embodiments, the prompt may comprises an audible alarm.

In any of the preceding embodiments, initiating the synchronization operation may comprise positioning the external device within 12 inches of the patient's eye.

In any of the preceding embodiments, the synchronization operation may comprise synchronizing a first timekeeping device onboard the intraocular pressure sensing implant with a second timekeeping device onboard the external device.

In any of the preceding embodiments, the external device may be configured to be worn by the patient.

In some embodiments, an intraocular pressure (IOP) sensing system may comprise: an intraocular pressure sensing implant to be implanted into the eye of a patient for capturing intraocular pressure measurements; and a temperature sensor for capturing temperature measurements, wherein the temperature measurements are used to at least partially compensate for the effect of temperature variations on the intraocular pressure sensing implant.

In any of the preceding embodiments, the temperature sensor may be onboard the intraocular pressure sensing implant.

In any of the preceding embodiments, the temperature sensor may be provided as part of an external device and the temperature measurements may be ambient temperature measurements.

In any of the preceding embodiments, wherein the ambient temperature measurements may be used to estimate intraocular temperature values.

In any of the preceding embodiments, he IOP sensing system may further comprise a processor to perform one or more operations to compensate for the effect of temperature variations on the intraocular pressure sensing implant.

In any of the preceding embodiments, the processor may be configured to adjust the intraocular pressure measurements based on the temperature measurements.

In any of the preceding embodiments, the processor may be configured to adjust measurement times corresponding to the intraocular pressure measurements based on the temperature measurements.

In any of the preceding embodiments, the processor may be configured to exclude one or more intraocular pressure measurements based on the temperature measurements.

In some embodiments, an intraocular pressure (IOP) sensing method may comprise: capturing intraocular pressure measurements using an intraocular pressure sensing implant implanted in the eye of a patient; capturing temperature measurements using a temperature sensor; and using the temperature measurements to at least partially compensate for the effect of temperature variations on the intraocular pressure sensing implant.

In any of the preceding embodiments, the temperature sensor may be onboard the intraocular pressure sensing implant.

In any of the preceding embodiments, the temperature sensor may be provided as part of an external device and the temperature measurements may be ambient temperature measurements.

In any of the preceding embodiments, the ambient temperature measurements may be used to estimate intraocular temperature values.

In any of the preceding embodiments, the IOP sensing method may further comprise performing one or more operations, using a processor, to compensate for the effect of temperature variations on the intraocular pressure sensing implant.

In any of the preceding embodiments, the IOP sensing method may further comprise adjusting the intraocular pressure measurements based on the temperature measurements.

In any of the preceding embodiments, the IOP sensing method may further comprise adjusting measurement times corresponding to the intraocular pressure measurements based on the temperature measurements.

In any of the preceding embodiments, the IOP sensing method may further comprise excluding one or more intraocular pressure measurements based on the temperature measurements.

In some embodiments, an intraocular pressure (IOP) sensing system may comprise: an IOP sensing implant configured to be implanted into a patient's eye, the IOP sensing implant including a supercapacitor for supplying at least a portion of operating power for the IOP sensing implant; and an external charging device configured to charge the IOP sensing implant, the external charging device including an output device for providing a prompt to the patient to carry out a charging interaction between the external device and the IOP sensing implant.

In any of the preceding embodiments, the IOP sensing implant may further include a battery for supplying at least a portion of the operating power for the IOP sensing implant.

In any of the preceding embodiments, the external charging device may be configured to output the prompt at charging interaction times, and the storage capacity of the supercapacitor may be greater than the expected energy usage of the IOP sensing implant between charging interaction times.

In any of the preceding embodiments, the external charging device may be configured to output the prompt at charging interaction times, and the storage capacity of the supercapacitor may be less than the expected energy usage of the IOP sensing implant between charging interaction times.

In any of the preceding embodiments, the storage capacity of the storage capacitor may be at least 0.01 µAh.

In any of the preceding embodiments, the storage capacity of the storage capacitor may be at least 0.10 µAh.

In any of the preceding embodiments, the storage capacity of the storage capacitor may be at least 1 µAh.

In any of the preceding embodiments, the prompt to carry out the charging interaction may coincide with a prompt to synchronize a timekeeping device onboard the IOP sensing implant.

In any of the preceding embodiments, the prompt to carry out the charging interaction may coincide with a prompt to download measurement data from the IOP sensing implant.

In some embodiments, an intraocular pressure (IOP) sensing method may comprise: providing an IOP sensing implant configured to be implanted into a patient's eye, the IOP sensing implant including a supercapacitor for supplying at least a portion of operating power for the IOP sensing implant; charging the IOP sensing implant using an external charging device; and providing a prompt to the patient, using an output device included with the external charging device, to carry out a charging interaction between the external device and the IOP sensing implant.

In any of the preceding embodiments, the IOP sensing implant may further include a battery for supplying at least a portion of the operating power for the IOP sensing implant.

In any of the preceding embodiments, the IOP sensing method may further comprise outputting the prompt at charging interaction times, and the storage capacity of the supercapacitor may be greater than the expected energy usage of the IOP sensing implant between charging interaction times.

In any of the preceding embodiments, the IOP sensing method may further comprise outputting the prompt at charging interaction times, and the storage capacity of the supercapacitor may be less than the expected energy usage of the IOP sensing implant between charging interaction times.

In any of the preceding embodiments, the storage capacity of the storage capacitor may be at least 0.01 µAh.

In any of the preceding embodiments, the storage capacity of the storage capacitor may be at least 0.10 µAh.

In any of the preceding embodiments, the storage capacity of the storage capacitor may be at least 1 µAh.

In any of the preceding embodiments, the prompt to carry out the charging interaction may coincide with a prompt to synchronize a timekeeping device onboard the IOP sensing implant.

In any of the preceding embodiments, the prompt to carry out the charging interaction may coincide with a prompt to download measurement data from the IOP sensing implant.

In some embodiments, an intraocular pressure sensor implant may comprise: a tubular main body; a bi-diameter sensor cap with a plug portion and a head portion, the diameter of the plug portion being smaller than the inner diameter of the tubular main body and the diameter of the head portion being larger than the inner diameter of the tubular main body, the sensor cap having a shoulder where the head portion and the plug portion meet; and a metal interlayer provided at a junction between the tubular main body and the shoulder of the sensor cap.

In some embodiments, a method of manufacturing an intraocular pressure sensor implant may comprise: providing a tubular main body; providing a bi-diameter sensor cap with a plug portion and a head portion, the diameter of the plug portion corresponding to the inner diameter of the tubular main body and the diameter of the head portion being larger than the inner diameter of the tubular main body, the sensor cap having a shoulder where the head portion and the plug portion meet; providing a metal interlayer between the tubular main body and the shoulder of the sensor cap; inserting the plug portion of the sensor cap into the tubular main body until the shoulder abuts against the tubular main body; heating the metal interlayer until it melts, thereby fusing the tubular main body and the sensor cap.

In any of the preceding embodiments, the method may further comprise heating the metal interlayer with a laser.

In any of the preceding embodiments, the sensor cap may be formed of a material that is substantially transparent to the laser.

In any of the preceding embodiments, the method may further comprise providing the metal interlayer as a preformed component of annular shape.

In any of the preceding embodiments, the method may further comprise providing the metal interlayer on an end surface of the tubular main body.

In any of the preceding embodiments, the method may further comprise providing the metal interlayer on the shoulder of the sensor cap.

In any of the preceding embodiments, an intraocular pressure sensor implant may comprise: an intraocular pressure sensing module; and a tubular main body, the tubular main body including a first portion having a first diameter and a second portion having a second diameter which is larger than the first diameter.

In any of the preceding embodiments, the implant may further include a tip cap inserted into the first portion of the tubular main body.

In any of the preceding embodiments, the implant may further include a sensor cap inserted into the first portion of the tubular main body, the intraocular pressure sensing module being provided in the sensor cap.

In any of the preceding embodiments, the tubular main body may be elongate.

In any of the preceding embodiments, the tubular main body may be sized and shaped to be inserted into the supraciliary/suprachoroidal space of a human eye.

In any of the preceding embodiments, the first portion and the second portion of the tubular main body may be joined by a shoulder.

In any of the preceding embodiments, the shoulder may be a step transition between the first portion and the second portion of the tubular main body.

In any of the preceding embodiments, the shoulder may be a tapered transition between the first portion and the second portion of the tubular main body.

In some embodiments, a method for surgically implanting an intraocular pressure (IOP) sensing implant may comprise: providing the IOP sensing implant, wherein the IOP sensing implant includes an IOP sensing module and a tubular main body, the tubular main body including a first portion having a first diameter and a second portion having a second diameter which is larger than the first diameter; and inserting the IOP sensing implant into eye tissue such that the first portion of the tubular main body is located in the eye tissue and the second portion of the tubular main body extends from the eye tissue.

In any of the preceding embodiments, the eye tissue may comprise the supraciliary/suprachoroidal space of a human eye.

In any of the preceding embodiments, the first portion and the second portion of the tubular main body may be joined by a shoulder, and inserting the IOP sensing implant into eye tissue may comprise abutting the shoulder against the eye tissue.

In some embodiments, an intraocular pressure sensor implant may comprise: an intraocular pressure sensing module; and a housing having a depression, the intraocular pressure sensing module being located in the depression.

In any of the preceding embodiments, the intraocular pressure sensor implant may further comprise a peripheral wall surrounding the depression.

In any of the preceding embodiments, the housing may include a tubular main body and a sensor cap configured to be inserted into an end of the tubular main body, and the intraocular pressure sensing module may be located in the sensor cap.

In any of the preceding embodiments, a hydrophilic material may be provided in the depression.

In any of the preceding embodiments, the intraocular pressure sensing module may include a flexible diaphragm.

In any of the preceding embodiments, the intraocular pressure sensor implant may further comprise a non-compressible, pressure-transmitting gel provided in the depression.

In some embodiments, a system for surgically implanting an intraocular pressure (IOP) sensing implant may comprise: an intraocular pressure sensing implant having an intraocular pressure sensing module and a housing with a depression, the intraocular pressure sensing module being located in the depression; and a delivery apparatus having a distal portion configured to engage the intraocular pressure sensing implant, the distal portion including a projection configured to mate with the depression in the housing of the intraocular pressure sensing implant.

In any of the preceding embodiments, the depression in the intraocular pressure sensing implant and the projection of the distal portion of the delivery apparatus may be physical complements of one another.

In any of the preceding embodiments, the length of the projection may be less than or equal to the depth of the depression.

In any of the preceding embodiments, the diameter of the projection may be no greater than the diameter of the depression.

In any of the preceding embodiments, the distal portion of the delivery apparatus may include a main body having a diameter that is greater than the diameter of the depression.

In some embodiments, a method for surgically implanting an intraocular pressure (IOP) sensing implant may comprise: providing an intraocular pressure sensing implant having an intraocular pressure sensing module and a housing with a depression, the intraocular pressure sensing module being located in the depression; providing a delivery apparatus having a distal portion configured to engage the intraocular pressure sensing implant, the distal portion including a projection configured to mate with the depression in the housing of the intraocular pressure sensing implant; engaging the depression with the distal portion of the delivery apparatus; and inserting the intraocular pressure sensing implant into the eye of a patient using the delivery apparatus.

In any of the preceding embodiments, the method may further comprise removing the distal portion of the delivery apparatus from the depression after inserting the intraocular pressure sensing implant into the eye of the patient.

In any of the preceding embodiments, removing the distal portion of the delivery apparatus from the depression may cause aqueous humor in the eye to be drawn into the depression.

In any of the preceding embodiments, the depression in the intraocular pressure sensing implant and the projection of the distal portion of the delivery apparatus may be physical complements of one another.

In any of the preceding embodiments, the length of the projection may be less than or equal to the depth of the depression.

In any of the preceding embodiments, the diameter of the projection may be no greater than the diameter of the depression.

In any of the preceding embodiments, the distal portion of the delivery apparatus may include a main body having a diameter that is greater than the diameter of the depression.

In some embodiments, an intraocular pressure sensor implant may comprise: an intraocular pressure sensing module; and a multi-part housing, at least one of the parts of the multi-part housing including an injection port to facilitate injection of a sterilization agent after the parts of the multi-part housing have been assembled.

In any of the preceding embodiments, the multi-part housing may include at least a tubular main body and one or more caps configured to mate with the tubular main body.

In any of the preceding embodiments, the injection port may be provided in a tip cap.

In any of the preceding embodiments, the multi-part housing may include one or more connecting structures to join parts of the multi-part housing, and the injection port may be physically separate from the one or more connecting structures.

In some embodiments, a method for sterilizing an intraocular pressure sensing implant may comprise: assembling at least a first housing part and a second housing part to form a housing of the intraocular pressure sensing implant, the housing comprising an intraocular pressure sensing module, and either the first housing part or the second housing part including an injection port; forming a hermetic seal at a junction between the first housing part and the second housing part; introducing a sterilization agent into the housing through the injection port; and sealing the injection port.

In any of the preceding embodiments, the method may further comprise evacuating the sterilization agent from the housing before sealing the injection port.

In any of the preceding embodiments, the method may further comprise introducing an inert gas into the housing through the injection port before sealing the injection port.

In any of the preceding embodiments, sealing the injection port may comprise inserting a plug into the injection port.

In any of the preceding embodiments, sealing the injection port may comprise applying heat to the injection port.

In some embodiments, an intraocular implant may comprise: a housing; a main cavity in the housing with one or more components provided therein; and a first enclosed lumen extending from a first opening located at a first end of the housing to a second opening located at a second end of the housing.

In any of the preceding embodiments, the first enclosed lumen may run the entire axial length of the housing.

In any of the preceding embodiments, the one or more components provided in the main cavity may include one or more electrical components.

In any of the preceding embodiments, the intraocular implant may further comprise a second enclosed lumen extending from a third opening located at the first end of the housing to a fourth opening located at the second end of the housing.

In any of the preceding embodiments, the first enclosed lumen and the second enclosed lumen may be provided on opposite sides of the main cavity.

In any of the preceding embodiments, the diameter of the first enclosed lumen and the diameter of the second enclosed lumen may be smaller than the diameter of the main cavity.

In any of the preceding embodiments, the housing may taper in size from the main cavity to the first enclosed lumen, and from the main cavity to the second enclosed lumen.

In some embodiments, an intraocular implant may comprise: a housing; a main cavity in the housing with one or more components provided therein; and one or more external flow-enabling features configured to increase flow of aqueous humor in proximity to the housing.

In any of the preceding embodiments, the one or more external flow-enabling features may comprise a rib projecting from an external surface of the housing.

In any of the preceding embodiments, the one or more external flow-enabling features may comprise a groove or channel formed in an external surface of the housing.

In any of the preceding embodiments, the one or more external flow-enabling features may extend the entire axial length of the housing.

In any of the preceding embodiments, the one or more external flow-enabling features may comprise an open-cell porous material.

In some embodiments, a system for anchoring an intraocular implant in the eye of a patient may comprise: the intraocular implant; a first anchoring tether attached to the intraocular implant, the first anchoring tether including an anchoring loop portion which extends from the intraocular implant; and an anchoring tack including a penetrating tip configured to be inserted into eye tissue and a body portion configured to hold the intraocular implant in place at the eye tissue via the first anchoring tether.

In any of the preceding embodiments, the first anchoring tether may include an attachment loop portion wrapped around the intraocular implant.

In any of the preceding embodiments, the attachment loop portion may be generally perpendicular to the anchoring loop portion.

In any of the preceding embodiments, the anchoring tack may be configured to hold the intraocular implant in place at the eye tissue via the anchoring loop portion of the first anchoring tether.

In any of the preceding embodiments, the anchoring tack may be configured to be inserted through the anchoring loop portion.

In any of the preceding embodiments, the anchoring tack may include a structure with a dimension that is larger than the diameter of the anchoring loop portion.

In any of the preceding embodiments, the anchoring tack may comprise a drug delivery implant.

In any of the preceding embodiments, the anchoring tacks may comprise a drainage stent.

In any of the preceding embodiments, the first anchoring tether may comprise a wire.

In any of the preceding embodiments, the system may further comprise a second anchoring tether, and the first anchoring tether may be connected to the intraocular implant at a first end and the second anchoring tether may be connected to the intraocular implant at a second end.

In any of the preceding embodiments, the first anchoring tether may be attached to the intraocular implant by welding or brazing it to the intraocular implant, by use of an adhesive, or by passing through an eyelet.

In some embodiments, a method for anchoring an intraocular implant in the eye of a patient may comprise: providing the intraocular implant, the intraocular implant including a first anchoring tether with an anchoring loop portion which extends from the intraocular implant; providing a first anchoring tack which includes a penetrating tip configured to be inserted into eye tissue; inserting the intraocular implant and the first anchoring tack into the eye; and inserting the penetrating tip of the first anchoring tack through the anchoring loop portion of the first anchoring tether and into the eye tissue.

In any of the preceding embodiments, the penetrating tip of the first anchoring tack may be inserted through the anchoring loop portion of the first anchoring tether before inserting the intraocular implant and the first anchoring tether into the eye.

In any of the preceding embodiments, the penetrating tip of the first anchoring tack may be inserted through the anchoring loop portion of the first anchoring tether after inserting the intraocular implant and the first anchoring tether into the eye.

In any of the preceding embodiments, the penetrating tip of the first anchoring tack may be inserted through the anchoring loop portion of the first anchoring tether and into eye tissue in one motion.

In any of the preceding embodiments, the intraocular implant may further include a second anchoring tether, and the method may further comprise: providing a second anchoring tack with an anchoring loop portion which extends from the intraocular implant; and inserting at least a portion of the second anchoring tack through the anchoring loop portion of the second anchoring tether.

In some embodiments, an intraocular implant component may comprise: a substrate with a mounting surface, the mounting surface including an electrically-conductive via formed therein; and a thin-film battery mounted on the mounting surface of the substrate, the battery comprising, one or more electrically-active layers, an electrical terminal on the surface of the battery in contact with the via, a sealing layer formed over the one or more electrically-active layers, the sealing layer extending to the mounting surface of the substrate around the entire perimeter of the battery without a gap between the sealing layer and the mounting surface.

In any of the preceding embodiments, the sealing layer may comprise a metal.

In any of the preceding embodiments, the intraocular implant component may further comprise an insulating layer formed between the one or more electrically-active layers and the sealing layer.

In any of the preceding embodiments, the substrate may comprise glass and the via may comprise silicon or metal.

In any of the preceding embodiments, the substrate may comprise ceramic and the via may comprise metal.

In any of the preceding embodiments, the thin-film battery may comprise a lithium-ion battery.

In any of the preceding embodiments, the via may be flush with the mounting surface.

In any of the preceding embodiments, the via may extend through the entire thickness of the substrate.

In any of the preceding embodiments, the one or more electrically-active layers may include a cathode current collector layer, a cathode layer, an electrolyte layer, an anode current collector layer, or an anode layer.

In any of the preceding embodiments, the battery may be mounted over the via.

In any of the preceding embodiments, the battery may not include an electrical interconnect extending laterally from the battery over the substrate.

In any of the preceding embodiments, the battery may be fabricated on the mounting surface of the substrate over the via.

In some embodiments, an intraocular implant may comprise: a substrate with a mounting surface for one or more electrical components; a first electrical component mounted on the substrate; a second electrical component mounted on the substrate over the first electrical component such that the second electrical component spans the first electrical component and the first electrical component is located in a space between the second electrical component and the substrate.

In any of the preceding embodiments, the first electrical component may comprise a battery.

In any of the preceding embodiments, the battery may comprise a thin-film battery.

In any of the preceding embodiments, the thickness of the film-film battery may be 30 µm or less.

In any of the preceding embodiments, the second electrical component may comprise an integrated circuit.

In any of the preceding embodiments, the second electrical component may be connected to the substrate by one or more solder bumps.

In any of the preceding embodiments, the second electrical component may be connected to the substrate by one or more stud bumps.

In any of the preceding embodiments, the one or more solder bumps may have a dimension which is larger than the thickness of the first electrical component.

In any of the preceding embodiments, the one or more solder bumps may have a diameter greater than 50 µm.

In some embodiments, an intraocular implant comprises: a housing; and an antenna provided in the housing, the antenna comprising a first row of a plurality of turns of wire which form at least a portion of a coil extending in a longitudinal direction, each of the plurality of turns of wire in the first row being in contact with an adjacent turn of wire in the longitudinal direction, and a second row of a plurality of turns of wire which form at least a portion of the coil, each of the plurality of turns of wire in the second row being in contact with an adjacent turn of wire in the longitudinal direction and an adjacent turn of wire in the radial direction.

In any of the preceding embodiments, the self-resonant frequency of the antenna may be less than 100 MHz.

In any of the preceding embodiments, the self-resonant frequency of the antenna may be less than 50 MHz.

In any of the preceding embodiments, the intraocular implant may further comprise one or more electrical components provided in an interior space of the coil.

In any of the preceding embodiments, at least one of the electrical components may comprise an integrated circuit implemented using subthreshold transistors.

In any of the preceding embodiments, the antenna may not be connected to a capacitor or inductor circuit element which is used to tune an operating frequency of the antenna.

In any of the preceding embodiments, the first row and the second row of turns of wire may be arranged such that electrical current travels through the first row and the second row in the same direction.

In any of the preceding embodiments, the intraocular implant may further comprise one or more additional rows of turns of wire radially beyond the first row and the second row.

In some embodiments, an intraocular implant may comprise: a tubular main body, the tubular main body including a first portion having a first diameter and a second portion having a second diameter which is larger than the first diameter; and an antenna at least partially located in the second portion of the tubular main body.

In any of the preceding embodiments, the antenna may be completely located in the second portion of the tubular main body.

In any of the preceding embodiments, the antenna may be a coil antenna.

In any of the preceding embodiments, the diameter of the coil antenna may be larger than the first diameter of the first portion of the tubular main body.

In any of the preceding embodiments, the tubular main body may be elongate.

In any of the preceding embodiments, the implant may be sized and shaped to be inserted into the suprachoroidal/supraciliary space of a patient's eye.

In any of the preceding embodiments, the intraocular implant may further comprise an intraocular pressure sensing module located in the second portion of the tubular main body.

In any of the preceding embodiments, the first portion and the second portion of the tubular main body may be joined by a shoulder.

In any of the preceding embodiments, the shoulder may be a step transition between the first portion and the second portion of the tubular main body.

In some embodiments, an intraocular implant may comprise: a first pressure sensing module; a separate second pressure sensing module; and at least one controller module configured to determine pressure measurements using each of the first and second pressure sensing modules.

In any of the preceding embodiments, either the first pressure sensing module or the second pressure sensing module may be provided in a housing with a measurement storage module, a controller module, or a transceiver module.

In any of the preceding embodiments, both the first pressure sensing module and the second pressure sensing module may be provided in one or more housings with a measurement storage module, a controller module, or a transceiver module.

In any of the preceding embodiments, the first pressure sensing module and the second pressure sensing module may be joined by a common housing.

In any of the preceding embodiments, the housing may comprise an elongate tube.

In any of the preceding embodiments, the first pressure sensing module and the second pressure sensing module may be joined by a tether.

In any of the preceding embodiments, the tether may comprise a communication cable to communicate pressure measurements between the first pressure sensing module and the second pressure sensing module.

In any of the preceding embodiments, the first pressure sensing module may be configured to be located in a first pressure-transmitting medium of a human eye and the second pressure sensing module may be configured to be located in a second pressure-transmitting medium of the eye.

In any of the preceding embodiments, the first pressure-transmitting medium may have a pressure that is correlated with intraocular pressure and the second pressure-transmitting medium may have a pressure that is correlated with atmospheric pressure.

In any of the preceding embodiments, the first pressure-transmitting medium may comprise aqueous humor of the eye.

In any of the preceding embodiments, the second pressure-transmitting medium may comprise fluid under the conjunctiva of the eye.

In any of the preceding embodiments, the controller may be configured to take pressure measurements from the first and second pressure sensing modules within ten minutes of one another.

In any of the preceding embodiments, the controller may be configured to take pressure measurements from the first and second pressure sensing modules within one minute of one another.

In any of the preceding embodiments, the controller may be configured to take pressure measurements from the first and second pressure sensing modules substantially concurrently.

In any of the preceding embodiments, the controller may be configured to subtract a first measurement taken using either the first or second pressure sensing modules from a second measurement taken using the other of the first and second pressure sensing modules.

In some embodiments, a method for inserting an intraocular implant may comprise: providing an intraocular implant with a first pressure sensing module, a separate second pressure sensing module, and at least one controller module configured to determine pressure measurements using each of the first and second pressure sensing modules; positioning the first pressure sensing module in a first pressure-transmitting medium of the eye; and positioning the second pressure sensing module in a second pressure-transmitting medium of the eye.

In any of the preceding embodiments, the method may further comprise inserting at least a portion of the intraocular implant through the sclera of the eye.

In any of the preceding embodiments, inserting at least a portion of the intraocular implant through the sclera of the eye may comprise using an ab interno technique.

In any of the preceding embodiments, inserting at least a portion of the intraocular implant through the sclera may comprise forming a tunnel through the sclera using a tool.

In any of the preceding embodiments, the tunnel through the sclera may be accessed through the suprachoroidal space of the eye.

In any of the preceding embodiments, the first pressure-transmitting medium may comprise aqueous humor of the eye.

In any of the preceding embodiments, the second pressure-transmitting medium may comprise fluid under the conjunctiva of the eye.

In some embodiments, an intraocular implant may comprise: a differential pressure sensing module; and at least one controller module configured to determine a pressure measurement using the differential pressure sensing module.

In any of the preceding embodiments, the differential pressure sensing module may comprise at least one flexible diaphragm.

In any of the preceding embodiments, the differential pressure sensor may be provided at least partially in a housing, and the at least one flexible diaphragm may have two sides, the sides being exposed to external pressure at different regions of the housing.

In any of the preceding embodiments, the at least one flexible diaphragm may be exposed to pressure via one or more channels.

In any of the preceding embodiments, the at least one flexible diaphragm may be exposed to pressure via one or more pressure-transmitting fluids sealed inside the housing.

In any of the preceding embodiments, the different locations may comprise different pressure-transmitting mediums of a human eye.

In some embodiments, a method for inserting an intraocular implant may comprise: providing an intraocular implant with a housing, a differential pressure sensing module at least partially provided in the housing, the differential pressure sensing module comprising at least one flexible diaphragm having two sides exposed to external pressure at first and second different regions of the housing, the intraocular implant further comprising at least one controller module configured to determine a pressure measurement using the differential pressure sensing module; positioning the first region of the housing in a first pressure-transmitting medium of the eye; and positioning the second region of the housing in a second pressure-transmitting medium of the eye.

In any of the preceding embodiments, the method may further comprise inserting at least a portion of the intraocular implant through the sclera of the eye.

In any of the preceding embodiments, inserting at least a portion of the intraocular implant through the sclera of the eye may comprise using an ab interno technique.

In any of the preceding embodiments, inserting at least a portion of the intraocular implant through the sclera may comprise forming a tunnel through the sclera using a tool.

In any of the preceding embodiments, the tunnel through the sclera may be accessed through the suprachoroidal space of the eye.

In any of the preceding embodiments, the first pressure-transmitting medium may comprise aqueous humor of the eye.

In any of the preceding embodiments, the second pressure-transmitting medium may comprise fluid under the conjunctiva of the eye.

Additional Considerations

Various embodiments of implantable physiological sensors, and associated methods, with a variety of features, have been described herein. Although not every embodiment has been illustrated with every feature, it should be understood that the features described herein can be freely combined with the various embodiments that are described and illustrated. The various physiological sensors described herein can also have any feature, characteristic, element, etc. that is disclosed in connection with the sensor devices described in the following U.S. patent documents, which are each hereby incorporated by reference in their entirety: U.S. Pat. Nos. 6,981,958; 7,678,065; U.S. Patent Publication 2010/0056979; and U.S. Patent Publication 2010/0106073. In addition, the various physiological sensors described herein can be used in, for example, any manner or application that is described in the foregoing patent documents.

The various illustrative devices, logical blocks, modules, circuits, and algorithm steps described in connection with the embodiments disclosed herein can be implemented as, for example, electronic hardware (e.g., analog and/or digital circuitry), computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Some of the various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein.

Embodiments have been described in connection with the accompanying drawings. However, it should be understood that the figures are not necessarily drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure. The scope of certain inventions disclosed herein is indicated by the appended claims rather than by the foregoing description. All changes which come within the meaning and range of equivalency of the claims are to be embraced within their scope.

What is claimed is:

1. An intraocular pressure (IOP) sensing system comprising:
    an intraocular pressure sensing implant to be implanted into an eye of a patient for capturing absolute intraocular pressure measurements, such that a proximal end of the intraocular pressure sensing implant is configured to be disposed in an anterior chamber of the eye and a distal end of the intraocular pressure sensing implant is configured to be disposed in a suprachoroidal space of the eye between a choroid of the eye and a sclera of the eye, wherein the intraocular pressure sensing implant comprises a sensing module configured to be disposed in the anterior chamber of the eye; and
    an external device for capturing atmospheric pressure measurements,
    wherein the intraocular pressure sensing implant comprises a first onboard timekeeping device, wherein the intraocular pressure sensing implant is configured to capture an absolute intraocular pressure measurement in the anterior chamber at an appointed time as indicated by the first onboard timekeeping device, wherein the external device comprises a second timekeeping device, wherein the external device is configured to capture a plurality of atmospheric pressure measurements around an appointed time as indicated by the second timekeeping device, wherein the external device is configured to download absolute intraocular pressure measurements from the intraocular pressure sensing implant, and wherein the external device is configured to calculate a gauge IOP value avoiding inaccuracies due to an offset between the appointed time as indicated by the first onboard timekeeping device and the appointed time as indicated by the second timekeeping device.

2. The IOP sensing system of claim 1, wherein the external device is configured to capture the plurality of atmospheric pressure measurements during a window of time which extends before and after the appointed time as indicated by the second timekeeping device.

3. The IOP sensing system of claim 1, wherein the external device comprises a processor configured to analyze the plurality of atmospheric pressure measurements to determine a measure of the variation between the plurality of atmospheric pressure measurements.

4. The IOP sensing system of claim 3, wherein the processor is configured to determine whether the variation is within a predetermined range.

5. The IOP sensing system of claim 4, wherein the processor is configured to correlate one or more of the plurality of atmospheric pressure measurements with an absolute intraocular pressure measurement if the variation is within the predetermined range.

6. The IOP sensing system of claim 5, wherein the processor is configured to calculate the gauge IOP value from the correlated atmospheric pressure and absolute intraocular pressure measurements.

7. The IOP sensing system of claim 1, wherein the external device is configured to execute a synchronization operation by wirelessly transmitting synchronization information to the intraocular pressure sensing implant to aid in correlating one or more atmospheric pressure measurements with one or more absolute intraocular pressure measurements.

8. The IOP sensing system of claim 7, wherein the synchronization information comprises a unique identification value or a timestamp.

9. The IOP sensing system of claim 7, wherein the external device initiates the synchronization operation automatically at a predetermined time or interval.

10. The IOP sensing system of claim 7, wherein the external device is configured to prompt the patient to initiate the synchronization operation.

11. The IOP sensing system of claim 10, wherein the prompt comprises an audible alarm.

12. The IOP sensing system of claim 10, wherein initiating the synchronization operation comprises positioning the external device within 12 inches of the patient's eye.

13. The IOP sensing system of claim 7, wherein the synchronization operation comprises synchronizing the first timekeeping device onboard the intraocular pressure sensing implant with the second timekeeping device onboard the external device.

14. The IOP sensing system of claim 1, wherein the external device is configured to be worn by the patient.

15. An intraocular pressure (IOP) sensing method comprising:
capturing an absolute intraocular pressure measurement from an intraocular pressure sensing implant implanted in an eye of a patient, wherein a proximal end of the intraocular pressure sensing implant is disposed in an anterior chamber of the eye and a distal end of the intraocular pressure sensing implant is disposed in a suprachoroidal space of the eye between a choroid of the eye and a sclera of the eye, wherein the intraocular pressure sensing implant comprises a sensing module disposed in the anterior chamber of the eye, and wherein the intraocular sensing implant further comprises a first onboard timekeeping device, the absolute intraocular pressure measurement having been captured in the anterior chamber at an appointed time as indicated by the first onboard timekeeping device;
capturing a plurality of atmospheric pressure measurements from an external device outside of the eye, wherein the external device comprises a second timekeeping device, the plurality of atmospheric pressure measurement having been captured around an appointed time as indicated by the second timekeeping device;
downloading, via the external device, absolute intraocular pressure measurements from the intraocular pressure sensing implant; and
calculating a gauge IOP value avoiding inaccuracies due to an offset between the appointed time as indicated by the first onboard timekeeping device and the appointed time as indicated by the second timekeeping device.

16. The IOP sensing method of claim 15, wherein the plurality of atmospheric pressure measurements are captured during a window of time which extends before and after the appointed time as indicated by the second timekeeping device.

17. The IOP sensing method of claim 15, further comprising analyzing the plurality of atmospheric pressure measurements to determine a measure of the variation between the plurality of atmospheric pressure measurements.

18. The IOP sensing method of claim 17, further comprising determining whether the variation is within a predetermined range.

19. The IOP sensing method of claim 18, further comprising correlating one or more of the plurality of atmospheric pressure measurements with the absolute intraocular pressure measurement if the variation is within the predetermined range.

20. The IOP sensing method of claim 19, wherein calculating the gauge IOP value comprises using the correlated atmospheric pressure and absolute intraocular pressure measurements.

21. The IOP sensing method of claim 17, further comprising analyzing the plurality of atmospheric pressure measurements using a processing device that is separate from the external device.

22. The IOP sensing method of claim 15, further comprising executing a synchronization operation by wirelessly transmitting synchronization information to the intraocular pressure sensing implant to aid in correlating one or more atmospheric pressure measurements with the absolute intraocular pressure measurement.

23. The IOP sensing method of claim 22, wherein the synchronization information comprises a unique identification value or a timestamp.

24. The IOP sensing method of claim 22, further comprising initiating the synchronization operation automatically at a predetermined time or interval.

25. The IOP sensing method of claim 22, further comprising prompting the patient to initiate the synchronization operation.

26. The IOP sensing method of claim 25, wherein the prompt comprises an audible alarm.

27. The IOP sensing method of claim 25, wherein initiating the synchronization operation comprises positioning the external device within 12 inches of the patient's eye.

28. The IOP sensing method of claim 22, wherein the synchronization operation comprises synchronizing the first timekeeping device onboard the intraocular pressure sensing implant with the second timekeeping device onboard the external device.

29. The IOP sensing method of claim 15, wherein the external device is configured to be worn by the patient.

* * * * *